(12) United States Patent
Barros Rodrigues et al.

(10) Patent No.: US 11,185,079 B2
(45) Date of Patent: Nov. 30, 2021

(54) CONTROL OF *COLEOPTERAN* INSECTS

(71) Applicant: GreenLight Biosciences, Inc., Medford, MA (US)

(72) Inventors: Thais Barros Rodrigues, Durham, NC (US); Suresh D. Desai, Apex, NC (US); Krishnakumar Sridharan, Cary, NC (US)

(73) Assignee: GreenLight Biosciences, Inc., Medford, MA (US)

( * ) Notice: Subject to any disclaimer, the term of this patent is extended or adjusted under 35 U.S.C. 154(b) by 0 days.

(21) Appl. No.: 16/583,863

(22) Filed: Sep. 26, 2019

(65) Prior Publication Data

US 2020/0093138 A1 Mar. 26, 2020

Related U.S. Application Data

(60) Provisional application No. 62/737,041, filed on Sep. 26, 2018.

(51) Int. Cl.
*A61K 48/00* (2006.01)
*C12N 15/11* (2006.01)
*C07H 21/02* (2006.01)
*C07H 21/04* (2006.01)
*A01N 63/00* (2020.01)
*A01N 25/04* (2006.01)
*C12N 15/82* (2006.01)

(52) U.S. Cl.
CPC ............ *A01N 63/00* (2013.01); *A01N 25/04* (2013.01); *C12N 15/8285* (2013.01)

(58) Field of Classification Search
CPC .. C12N 15/82; C12N 15/113; C12N 15/1135; C12N 15/8218; C12N 15/8286; C12N 2310/14; C12N 2310/531; A01N 63/02; C07K 14/32; C07K 14/195
See application file for complete search history.

(56) References Cited

U.S. PATENT DOCUMENTS

| 7,022,828 | B2 | 4/2006 | McSwiggen |
| 7,777,022 | B2 | 8/2010 | Bentwich et al. |
| 7,943,754 | B2 | 5/2011 | Bentwich et al. |
| 8,097,712 | B2 | 1/2012 | Paldi et al. |

(Continued)

FOREIGN PATENT DOCUMENTS

| EP | 2 438 813 A1 | 4/2012 |
| WO | WO 2006/126040 A1 | 11/2006 |

(Continued)

OTHER PUBLICATIONS

GenBank Accession No. XM_023166539, submitted to GenBank on Dec. 1, 2017, Predicted: Leptinotarsa decemlineata baculoviral IAP repeat-containing protein 2 (LOC111510616), transcript variant X2, mRNA.*

(Continued)

*Primary Examiner* — Terra C Gibbs
(74) *Attorney, Agent, or Firm* — Wolf, Greenfield & Sacks, P.C.

(57) ABSTRACT

Provided herein are methods for using RNAi molecules targeting an Inhibitor of Apoptosis (IAP) gene for controlling Coleopteran insects, methods for producing RNAi molecules targeting IAP, and compositions comprising RNAi molecules targeting IAP.

20 Claims, 11 Drawing Sheets
Specification includes a Sequence Listing.

(56) References Cited

U.S. PATENT DOCUMENTS

| | | | |
|---|---|---|---|
| 8,178,503 | B2 | 5/2012 | Rigoutsos et al. |
| 9,777,288 | B2 | 10/2017 | Beattie et al. |
| 9,850,496 | B2 | 12/2017 | Beattie et al. |
| 9,856,495 | B2 | 1/2018 | Beattie et al. |
| 10,059,941 | B2 | 8/2018 | Krieg et al. |
| 10,240,161 | B2 | 3/2019 | Avniel et al. |
| 10,240,162 | B2 | 3/2019 | Avniel et al. |
| 10,378,012 | B2 | 8/2019 | Crawford et al. |
| 10,597,676 | B2 | 3/2020 | Beattie et al. |
| 10,655,136 | B2 | 5/2020 | Huang et al. |
| 10,683,505 | B2 | 6/2020 | Avniel et al. |
| 10,883,103 | B2 | 1/2021 | Bennett et al. |
| 10,968,449 | B2 | 4/2021 | Beattie et al. |
| 10,975,387 | B2 | 4/2021 | Beattie et al. |
| 2007/0026394 | A1 | 2/2007 | Blatt et al. |
| 2012/0157512 | A1 | 6/2012 | Ben-Chanoch et al. |
| 2014/0230090 | A1 | 8/2014 | Avniel et al. |
| 2016/0230186 | A1 | 8/2016 | Baum et al. |
| 2017/0166912 | A1 | 6/2017 | Brower-Toland et al. |
| 2017/0183683 | A1 | 6/2017 | Baum et al. |
| 2018/0360030 | A1 | 12/2018 | Morgenstern et al. |
| 2019/0048337 | A1 | 2/2019 | Hsu et al. |
| 2019/0316130 | A1 | 10/2019 | Crawford et al. |

FOREIGN PATENT DOCUMENTS

| | | |
|---|---|---|
| WO | WO 2013/192256 A1 | 12/2013 |
| WO | WO 2017/176963 A1 | 10/2017 |
| WO | WO 2019/075167 A1 | 4/2019 |

OTHER PUBLICATIONS

Wikipedia (downloaded from Antisense RNA—Wikipedia on Mar. 8, 2021) https://en.wikipedia.org/wiki/Antisense_RNA.*

Arziman et al., E-RNAi: a web application to design optimized RNAi constructs. Nucleic Acids Research. Jul. 2005;33(Web Server issue):W582-8.

Bramsen et al., A large-scale chemical modification screen identifies design rules to generate siRNAs with high activity, high stability and low toxicity. Nucleic Acids Research. 2009;37(9):2867-81. Epub Mar. 12, 2009.

Bramsen et al., Development of therapeutic-grade small interfering RNAs by chemical engineering. Frontiers in Genetics. Aug. 2012;3:1-22.

Gasparis et al., Artificial MicroRNA-Based Specific Gene Silencing of Grain Hardness Genes in Polyploid Cereals Appeared to Be Not Stable Over Transgenic Plant Generations. Frontiers in Plant Science. Jan. 2017;7:1-13.

Pridgeon et al., Topically Applied AaeIAP1, Double-Stranded RNA Kills Female Adults of *Aedes aegypti*. J. Med. Entomol. May 2008;45(3):414-20.

Erratum for Pridgeon et al., Topically Applied AaeIAP1, Double-Stranded RNA Kills Female Adults of *Aedes aegypti*. J. Med. Entomol. 2016;53(2):484.

Puglise et al., Expression Profiles and RNAi Silencing of Inhibitor of Apoptosis Transcripts in *Aedes, Anopheles*, and *Culex* Mosquitoes (*Diptera: culicidae*). Journal of Medical Entomology. 2016;53(2):304-14. Epub Dec. 11, 2015.

International Search Report and Written Opinion for PCT/US2019/053129 dated Dec. 12, 2019.

Baum et al., Progress Towards RNAi-Mediated Insect Pest Management. Advances in Insect Physiology. Sep. 2014;47:249-95.

Cao et al., A Systematic Study of RNAi Effects and dsRNA Stability in *Tribolium castaneum* and *Acyrthosiphon pisum*, Following Injection and Ingestion of Analogous dsRNAs. International Journal of Molecular Sciences. Apr. 2018;19:1079. 18 pages.

Rodrigues et al., Development of RNAi method for screening candidate genes to control emerald ash borer, *Agrilus planipennis*. Sci Rep. Aug. 7, 2017;7(1):7379. 8 pages.

Rodrigues et al., RNA interference in the Asian Longhorned Beetle: Identification of Key RNAi Genes and Reference Genes for RT-qPCR. Sci Rep. Aug. 21, 2017;7(1):8913. 10 pages.

Yoon et al., Double-stranded RNA binding protein, Staufen, is required for the initiation of RNAi in coleopteran insects. PNAS. Aug. 2018;115(33):8334-9.

Yoon et al., RNA interference in the Colorado potato beetle, *Leptinotarsa decemlineata*: Identification of key contributors. Insect Biochemistry and Molecular Biology. 2016;78:78-88. Epub Sep. 26, 2016.

Knorr et al., Gene silencing in Tribolium castaneum as a tool for the targeted identification of candidate RNAi targets in crop pests. Scientific Reports. 2018;8:2061.

Rodrigues et al., Identification of highly effective target genes for RNAi-mediated control of emerald ash borer, Agrilus planipennis. Sci Rep. Mar. 22, 2018;8(1):5020. doi: 10.1038/s41598-018-23216-6. PMID: 29568083; PMCID: PMC5864839.

* cited by examiner

SEQUENCE LISTING

<160> NUMBER OF SEQ ID NOS: 54

<210> SEQ ID NO 1
<211> LENGTH: 1564
<212> TYPE: DNA
<213> ORGANISM: Artificial Sequence
<220> FEATURE:
<223> OTHER INFORMATION: Synthetic Polynucleotide

<400> SEQUENCE: 1

| | | | | | | |
|---|---|---|---|---|---|---|
| ctaatgcatt | gcgttgttca | gatacaaacg | tacgtgcagt | tcagttcagt | tcagttctcg | 60 |
| tatcgctagt | ttgtcggagc | aattggttca | cttggtattt | ggggcgattt | taacgtgttt | 120 |
| tttacgaagg | atcttataaa | aatcatgcag | tgttacagca | tcatatttt | tggtactgag | 180 |
| aaggcatgaa | aatgaatcaa | acatttccca | caatcagcag | ttactctgat | cagacagaca | 240 |
| ataacccaa | acataaaagt | ttttttgaag | taaacgtcaa | caattccgca | ttggaggcga | 300 |
| gactgagaac | atttgacaat | tggccaagca | cacaactatc | caaggaagcg | ctcgcgtctg | 360 |
| ccggttttga | atacactgga | caagatgaca | ttgttttgtg | tcgtttctgt | aagatagaag | 420 |
| gatacaattg | ggtatctgga | gatgatccaa | tggcagacca | tcgagaatgg | agtcctgact | 480 |
| gtcctttat | tagaactgta | gagaacggca | ggtctgggag | taatagaaac | gcagatactt | 540 |
| gtggactgta | cggcatagag | gttcttccaa | attccctccc | ggaggacagg | agatccattg | 600 |
| atttgcaaca | gttgggaatc | cacaaaggaa | gtggaccaca | caaccaggat | aaaataacgg | 660 |
| taaatagtcg | actagcaacg | ttcgaaaact | ggcccaagtc | catcaagcag | agacccgttg | 720 |
| atttggcaga | agcgggattt | tattataccg | gtgtgggaga | ccagacactt | tgtttctact | 780 |
| gtggtggtgg | tctaaaagac | tgggaagaat | ctgacgaacc | ttgggaacaa | cacgcccttt | 840 |
| ggttcagcaa | gtgtgttttt | ctaaatttga | aaaaggtaa | agactttgtc | gaaaaggtca | 900 |
| aacagagggc | agaccctctc | ttgtcgctcc | ccggaacaag | tcaagacaag | accaaagagc | 960 |
| tagaagaacc | taaagagccc | tgcagtagga | ctccagaaaa | ggctgaaaag | actactgaaa | 1020 |
| cggaagcaac | agagaagact | ttgtgtaaaa | tctgttataa | aaacgaactt | ggtgttgtat | 1080 |
| tcttgccttg | tggacatgtt | gttgcttgtg | tagattgtgc | ttctgctttg | aaaacttgtg | 1140 |
| ctgtctgtag | gaaaccttg | gaagcgacag | ttcgagcatt | tctctcataa | tttttccatt | 1200 |
| cttaatttt | cgtttctcag | atctagtcaa | tttgaatttg | attcttgaag | gtttattaaa | 1260 |
| aagttttgtc | aaaaattatt | cttttcttgt | tttaggatta | gaagtaaatc | tattttata | 1320 |
| caatctgagt | acaaattcca | catactttt | tagttataag | tttgaagcgc | ttatgaaaca | 1380 |
| tactttagt | tcattaatga | ctgcaaacca | tatctttcgt | acactaatac | ttattagtta | 1440 |
| tcaagctctc | gtgagtggaa | cttccttatt | agaacatttt | attataaaac | tgacacagag | 1500 |
| atatatctgt | atgtttgtgt | gtatgttcac | taagtatgct | aataatataa | taattatga | 1560 |
| aaaa | | | | | | 1564 |

<210> SEQ ID NO 2
<211> LENGTH: 1453
<212> TYPE: DNA
<213> ORGANISM: Artificial Sequence
<220> FEATURE:
<223> OTHER INFORMATION: Synthetic Polynucleotide

<400> SEQUENCE: 2

| | | | | | | |
|---|---|---|---|---|---|---|
| ctaatgcatt | gcgttgttca | gatacaaacg | tacgtgcagt | tcagttcagt | tcagttctcg | 60 |
| tatcgctagt | tggcatgaaa | atgaatcaaa | catttcccac | aatcagcagt | tactctgatc | 120 |

```
agacagacaa taaccccaaa cataaaagtt tttttgaagt aaacgtcaac aattccgcat      180
tggaggcgag actgagaaca tttgacaatt ggccaagcac acaactatcc aaggaagcgc      240
tcgcgtctgc cggttttgaa tacactggac aagatgacat tgttttgtgt cgtttctgta      300
agatagaagg atacaattgg gtatctggag atgatccaat ggcagaccat cgagaatgga      360
gtcctgactg tcctttattt agaactgtag agaacggcag gtctgggagt aatagaaacg      420
cagatacttg tggactgtac ggcatagagg ttcttccaaa ttccctcccg gaggacagga      480
gatccattga tttgcaacag ttgggaatcc acaaggaag tggaccacac aaccaggata       540
aaataacggt aaatagtcga ctagcaacgt tcgaaaactg gcccaagtcc atcaagcaga      600
gacccgttga tttggcagaa gcgggatttt attataccgg tgtgggagac cagacacttt      660
gtttctactg tggtggtggt ctaaaagact gggaagaatc tgacgaacct tgggaacaac      720 acgcccttg gttcagcaag tgtgtttttc taaatttgaa aaaggtaaa gactttgtcg         780 aaaaggtcaa acagagggca gaccctctct tgtcgctccc cggaacaagt caagacaaga      840
ccaaagagct agaagaacct aaagagcct gcagtaggac tccagaaaag ctgaaaaga        900 ctactgaaac ggaagcaaca gagaagactt tgtgtaaaat ctgttataaa aacgaacttg      960
gtgttgtatt cttgccttgt ggacatgttg ttgcttgtgt agattgtgct tctgctttga     1020
aaacttgtgc tgtctgtagg aaacctttgg aagcgacagt tcgagcattt ctctcataat     1080
ttttccattc tttaattttc gtttctcaga tctagtcaat ttgaatttga ttcttgaagg     1140
tttattaaaa agttttgtca aaattattc ttttcttgtt ttaggattag aagtaaatct       1200
atttttatac aatctgagta caaattccac atactttttt agttataagt ttgaagcgct     1260
tatgaaacat acttttagtt cattaatgac tgcaaaccat atctttcgta cactaatact     1320
tattagttat caagctctcg tgagtggaac ttccttatta gaacatttta ttataaaact     1380
gacacagaga tatatctgta tgtttgtgtg tatgttcact aagtatgcta ataatataat     1440
aatttatgaa aaa                                                        1453

<210> SEQ ID NO 3
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 3
ggtgtgggag accagacact tgtttctac tgtggtggtg gtctaaaaga ctgggaagaa        60
tctgacgaac cttgggaaca acacgcccctt tggttcagca agtgtgttttt tctaaatttg    120 aaaaaaggta aagactttgt cgaaaaggtc aaacagaggg cagaccctct cttgtcgctc      180
cccggaacaa gtcaagacaa gaccaaagag ctagaagaac ctaaagagcc ctgcagtagg      240
actccagaaa aggctgaaaa gactactgaa acggaagcaa cagagaagac tttgtgtaaa      300
atctgttata aaaacgaact tggtgttgta ttcttgcctt gtggacatgt tgttgcttgt      360
gtagattgtg cttctgcttt gaaaacttgt gctgtctgta ggaaaccttt ggaagcgaca      420
gttcgagcat tt                                                          432

<210> SEQ ID NO 4
<211> LENGTH: 524
<212> TYPE: DNA
<213> ORGANISM: Artificial Sequence
<220> FEATURE:
```

<223> OTHER INFORMATION: Synthetic Polynucleotide

<400> SEQUENCE: 4

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctacccga ccacatgaag      240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acgg                     524
```

<210> SEQ ID NO 5
<211> LENGTH: 521
<212> TYPE: DNA
<213> ORGANISM: Artificial Sequence
<220> FEATURE:
<223> OTHER INFORMATION: Synthetic Polynucleotide

<400> SEQUENCE: 5

```
ctaatgcatt gcgttgttca gatacaaacg tacgtgcagt tcagttcagt tcagttctcg      60
tatcgctagt ttgtcggagc aattggttca cttggtattt gggcgatttt aacgtgtttt     120
tttacgaagg atcttataaa aatcatgcag tgttacagca tcatattttt tggtactgag     180
aaggcatgaa atgaatcaaa catttcccca caatcagcag ttactctgat cagacagaca     240
ataccccaa acataaaagt ttttttgaag taaacgtcaa caattccgca ttggaggcga     300
gactgagaac atttgacaat tggccaagca cacaactatc caaggaagcg ctcgcgtctg     360
ccggttttga atacactgga caagatgaca ttgtttttgtg tcgtttctgt aagatagaag     420
gatacaattg ggtatctgga gatgatccaa tggcagacca tcgagaatgg agtcctgact     480
gtccttttat tagaactgta gagaacggca ggtctgggag t                        521
```

<210> SEQ ID NO 6
<211> LENGTH: 522
<212> TYPE: DNA
<213> ORGANISM: Artificial Sequence
<220> FEATURE:
<223> OTHER INFORMATION: Synthetic Polynucleotide

<400> SEQUENCE: 6

```
aatagaaacg cagatacttg tggactgtac ggcatagagg ttcttccaaa ttccctcccg      60
gaggacagga gatccattga tttgcaacag ttgggaatcc acaaaggaag tggaccacac     120
aaccaggata aaataacggt aaatagtcga ctagcaacgt tcgaaaactg gcccaagtcc     180
atcaagcaga gacccgttga tttggcagaa gcgggatttt attataccgg tgtgggagac     240
cagacactt gtttctactg tggtggtggt ctaaaagact gggaagaatc tgacgaacct     300
tgggaacaac acgcccttg gttcagcaag tgtgttttc taaatttgaa aaaaggtaaa     360
gactttgtcg aaaaggtcaa acagagggca gaccctctct tgtcgctccc cggaacaagt     420
caagacaaga ccaaagagct agaagaacct aaagagccct gcagtaggac tccagaaaag     480
gctgaaaaga ctactgaaac ggaagcaaca gagaagactt tg                       522
```

<210> SEQ ID NO 7
<211> LENGTH: 521
<212> TYPE: DNA
<213> ORGANISM: Artificial Sequence
<220> FEATURE:
<223> OTHER INFORMATION: Synthetic Polynucleotide

<400> SEQUENCE: 7

| | |
|---|---|
| tgtaaaatct gttataaaaa cgaacttggt gttgtattct tgccttgtgg acatgttgtt | 60 |
| gcttgtgtag attgtgcttc tgctttgaaa acttgtgctg tctgtaggaa acctttggaa | 120 |
| gcgacagttc gagcatttct ctcataattt ttccattctt taattttcgt ttctcagatc | 180 |
| tagtcaattt gaatttgatt cttgaaggtt tattaaaaag ttttgtcaaa aattattctt | 240 |
| ttcttgtttt aggattagaa gtaaatctat ttttatacaa tctgagtaca aattccacat | 300 |
| acttttttag ttataagttt gaagcgctta tgaaacatac ttttagttca ttaatgactg | 360 |
| caaaccatat ctttcgtaca ctaatactta ttagttatca agctctcgtg agtggaactt | 420 |
| ccttattaga acattttatt ataaaactga cacagagata tatctgtatg tttgtgtgta | 480 |
| tgttcactaa gtatgctaat aatataataa tttatgaaaa a | 521 |

<210> SEQ ID NO 8
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 8

| | |
|---|---|
| gatgagtgac tgcagaatct tgtttccgc tgaggttgtt ggcttgaaca ctaggaaaga | 60 |
| ggttatgaac cttggtaact acacaccatt tgatgcagca agcgtgatct tctaaattag | 120 |
| ttagcaatga aagcctttgt ctaaggggtg aaccagcgtg ccgagcctct ctagcccctc | 180 |
| tctgacacaa gtcaaaacat gatcattggg cttgtagagc ctcgagaggt ctgcagtaga | 240 |
| acaccagacc aggctggaaa gtctcctgaa acagatccac cagaggagac gtagttgaaa | 300 |
| atccgttata gaatcgaact tcgcgttgta ccacggcttt ataggcaacc agttacttgt | 360 |
| ctagattgtg cttcagctac tagaaattgt gctgaaagga ggaaaccact gcaagggctg | 420 |
| gaacggggat ta | 432 |

<210> SEQ ID NO 9
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 9

| | |
|---|---|
| agtgttttaa aaacgcccct ttttggctac tgtagttgta gtttcaaaaa ctgtgaagaa | 60 |
| tcggacgatc attgggaaca acacgcgctt tcgttcagca agtggacttc tagaactttg | 120 |
| aaaaaaggta atgacacagt tgaggaggtc aaactgaggg cacacgctct cttgtcgcag | 180 |
| ccgggaacaa gacaagacat gaccaataag atagaaggac atacaggctc attgagtagg | 240 |
| gctcgagaaa aaggtcaaaa gactactgat acggaaccc cacagcacac attgtctact | 300 |
| atctgaccta agatctgacc tggtgttata ttcttgacct gtggacctgt tgtggcttgc | 360 |
| ctagattgag ctactgacat gaaaatatct gatgtctgta ggaagcatac ggaagcgacg | 420 |
| gcatgcgcat tt | 432 |

<210> SEQ ID NO 10
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 10

| | | | | | |
|---|---|---|---|---|---|
| gttgtgggag | accagtctat | gtggtgcaac | tatactggtg | gtcataaaaa | ctgggacata | 60 |
| tcagacgtac | ctcgggtaga | acccgcgctt | gggttcagga | agtgtgtttt | gctaaaaatg | 120 |
| atataagctc | aagactttgt | cgaaaacgac | aaccagaggg | aagaacatct | cttgtcgctc | 180 |
| tccgaaacaa | ctcaaaacaa | gaccaaaaag | atagaggtat | cggaagagcc | cagcagtagg | 240 |
| agcctcgaac | aggctgaaga | gactactaag | agggacgcta | cagagcacac | tttgactaag | 300 |
| atctgttaaa | aagacgagct | tggtttagtt | ttcttacctg | gttgacttgt | tgttgcctgt | 360 |
| cgaaattgtg | cttctgcttt | gaaaacttgt | gctgtctgta | ggcaaccttt | ggaatcgaca | 420 |
| gttagcgcat | tc | | | | | 432 |

<210> SEQ ID NO 11
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 11

| | | | | | |
|---|---|---|---|---|---|
| ggtgtaggag | accagacact | ctgtttctac | tgaggtgctc | gtctaggaga | ccgtgtagaa | 60 |
| tctaacgaac | cttgggaaca | acacgcccttt | tgtttcagcc | agtgtgatttt | tcaaaatgtg | 120 |
| aaataaggtt | aagactttgt | cggcaaggtc | aaacagaggc | cagaccatct | cttgacgcgc | 180 |
| cccgtaacaa | gtcaagaaaa | taccaacgag | ctacaagaac | ataagagcg | ctgcagtagg | 240 |
| actccggaaa | aggttgagaa | gactactgaa | agggaagcaa | gaggtaaggc | tatgtgttaa | 300 |
| ttctttttata | aagactttct | tggtgtcgta | tatttgcctt | gtggccatgt | tgttgctcgt | 360 |
| gtaggttgtt | cttctgctta | agcaacttgt | gctgtatgta | gcaaacttttt | gccagcggca | 420 |
| gttcgagcat | tt | | | | | 432 |

<210> SEQ ID NO 12
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 12

| | | | | | |
|---|---|---|---|---|---|
| ggtgtgggag | agcagacact | tcgtttctac | agtggtggcg | gtctaaaaga | ctgggaagaa | 60 |
| tctgacgagc | cttgcgaaca | acaggcactt | gggttcagca | agtttgcttt | tctgaatttg | 120 |
| aaaaaatgtt | aagaccttgt | cggaaaggtc | aaacagaggc | cagaccctct | cttgtggcac | 180 |
| ccctgaacaa | gtcaagacaa | gaccacaggc | cgagaagaac | ctaaagagcc | ctgcagcagg | 240 |
| actccagaca | aggctgaaaa | gactactgca | acggaagcag | gagaaaaggc | tttgtgtaaa | 300 |
| atctgttcta | aaaacgaact | tggagttgta | ttctggcctt | gtggccatgt | tgttgcgggt | 360 |
| gtcgattgtg | cgtctgcttt | gaatacttgt | gctgtcctta | ggaaaccttt | ggaagcgaca | 420 |
| gttcgagcaa | tt | | | | | 432 |

<210> SEQ ID NO 13
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 13

```
ggtgtgggag accagacact tgtttctac tgtgatggtg gtctaaaaga ctgggaaaaa      60
tctgacgaac cttgggtaca acacggcctt tggttcagca agtgtgtctt tataaatttg    120
aaaaaaggta aagactttgg cgaaaaggtc aagcagaggg caatccctct cttgtcgcac    180
cccggaacaa gtcaagacaa gaccaaagag ctagacgaac ctaaagagcc ctgcagtagg    240
actccagaaa aggctgaaaa gactactgaa acggaagcca cagagaagac tttgtgtaaa    300
atctgttata aaaaccaact tgatgttgtt ttccttgccat gtggacattt tgttgcttgt    360
ggagcttgtg cttctgcttt gaaaacttgt gctgtctgta ggaaacccttt ggaagcgaca    420
gttcgagcat tc                                                        432
```

<210> SEQ ID NO 14
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 14

```
gcagaccctc tcttgtcgct ccccggaaca agtcaagaca agaccaaaga gctagaagaa     60
cctaaagagc cctgcagtag gactccagaa aaggctgaaa agactactga acggaagca    120
acagagaaga ctttgtgtaa aatctgttat aaaaacgaac ttggtgttgt attcttgcct    180
tgtggacatg ttgttgcttg                                                200
```

<210> SEQ ID NO 15
<211> LENGTH: 150
<212> TYPE: DNA
<213> ORGANISM: Artificial Sequence
<220> FEATURE:
<223> OTHER INFORMATION: Synthetic Polynucleotide

<400> SEQUENCE: 15

```
gaacaagtca agacaagacc aaagagctag aagaacctaa agagccctgc agtaggactc     60
cagaaaaggc tgaaaagact actgaaacgg aagcaacaga gaagactttg tgtaaaatct    120
gttataaaaa cgaacttggt gttgtattct                                     150
```

<210> SEQ ID NO 16
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 16

```
gctagaagaa cctaaagagc cctgcagtag gactccagaa aaggctgaaa agactactga     60
aacggaagca acagagaaga ctttgtgtaa aatctgttat                          100
```

<210> SEQ ID NO 17
<211> LENGTH: 124
<212> TYPE: DNA
<213> ORGANISM: Artificial Sequence
<220> FEATURE:

<223> OTHER INFORMATION: Synthetic Polynucleotide

<400> SEQUENCE: 17

```
agtaggactc cagaaaaggc tgaaaagact actgaaacgg aagcaacaga gggagaagat    60
ctagtaggac tccagaaaag gctgaaaaga ctactgaaac ggaagcaaca gaggtacctc   120
tccc                                                                124
```

<210> SEQ ID NO 18
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 18

```
gaaaaggctg aaaagactac tgaaagggag aagatctgaa aaggctgaaa agactactga    60
aaggtacctc tccc                                                      74
```

<210> SEQ ID NO 19
<211> LENGTH: 1564
<212> TYPE: RNA
<213> ORGANISM: Artificial Sequence
<220> FEATURE:
<223> OTHER INFORMATION: Synthetic Polynucleotide

<400> SEQUENCE: 19

```
cuaaugcauu gcguuguuca gaucaaacg uacgugcagu ucaguucagu ucaguucucg      60
uaucgcuagu uugucggagc aauugguuca cuugguauuu ggggcgauuu uaacguguuu    120
uuuacgaagg aucuuauaaa aaucaugcag uuuacagca ucauauuuuu ugguacugag     180
aaggcaugaa aaugaaucaa acauuuccca caaucagcag uuacucugau cagacagaca    240
auaaccccaa acauaaaagu uuuuugaag uaaacgucaa caauuccgca uuggaggcga     300
gacugagaac auuugacaau uggccaagca cacaacuauc caaggaagcg cucgcgucug    360
ccgguuuuga auacacugga caagaugaca uuguuugug ucguuucugu aagauagaag     420
gauacaauug gguaucugga gaugauccaa uggcagacca ucgagaaugg aguccugacu    480
guccuuuuau uagaacugua gagaacggca ggucuggag uaauagaaac gcagauacuu     540
guggacugua cggcauagag guucuuccaa auucccuccc ggaggacagg agauccauug    600
auuugcaaca guugggaauc cacaaaggaa guggaccaca caaccaggau aaaauaacgg    660
uaaauagucg acuagcaacg uucgaaaacu ggcccaaguc caucaagcag agacccguug    720
auuuggcaga agcgggauuu uauuauaccg guguggagaa ccagacacuu uguuucuacu    780
guguguggugg ucuaaaagac ugggaagaau cugacgaacc uugggaacaa cacgcccuuu    840
gguucagcaa guguguuuu cuaaauuuga aaaaggtaa agacuuuguc gaaaagguca     900
aacagagggc agacccucuc uugucgcucc ccggaacaag ucaagacaag accaaagagc    960
uagaagaacc uaaagagccc ugcaguagga cuccagaaaa ggcugaaaag acuacugaaa   1020
cggaagcaac agagaagacu uguguaaaa ucuguauaa aaacgaacuu ggugguauu      1080
ucuugccuug uggacauguu guugcuugug uagauugug cuucugcuuug aaacuugug    1140
cugucuguag gaaaccuuug gaagcgacag uucgagcauu ucucucauaa uuuuccauu    1200
cuuuaauuuu cguuucucag aucuagucaa uuugaauuug auucugaag guuuauaaa    1260
aaguuuuguc aaaaauuauu cuuuucugu uuaggauua gaaguaaauc uauuuuaua     1320
caaucugagu acaaauucca cauacuuuuu uaguuauaag uuugaagcgc uuaugaaaca   1380
```

```
uacuuuuagu ucauuaauga cugcaaacca uaucuuucgu acacuaauac uuauuaguua    1440
ucaagcucuc gugaguggaa cuuccuuauu agaacauuuu auuauaaaac ugacacagag    1500
auauaucugu auguuugugu uauguucac uaaguaugcu aauaauauaa uaauuuauga    1560
aaaa                                                                 1564

<210> SEQ ID NO 20
<211> LENGTH: 1453
<212> TYPE: RNA
<213> ORGANISM: Artificial Sequence
<220> FEATURE:
<223> OTHER INFORMATION: Synthetic Polynucleotide

<400> SEQUENCE: 20
cuaaugcauu gcguuguuca gauacaaacg uacgugcagu ucaguucagu ucaguucucg      60
uaucgcuagu uggcaugaaa augaaucaaa cauuucccac aaucagcagu uacucugauc     120
agacagacaa uaaccccaaa cauaaaaguu uuuugaagu aaacgucaac aauuccgcau      180
uggaggcgag acugagaaca uuugacaauu ggccaagcac acaacuaucc aaggaagcgc     240
ucgcgucugc cgguuuugaa uacacuggac aagaugacau uguuuugugu cguuucugua     300
agauagaagg auacaauugg guaucuggag augauccaau ggcagaccau cgagaaugga     360
guccugacug uccuuuuauu agaacuguag agaacggcag gucugggagu aauagaaacg     420
cagauacuug uggacuguac ggcauagagg uucuuccaaa uccccucccg gaggacagga     480
gauccauuga uuugcaacag uugggaaucc acaaaggaag uggaccacac aaccaggaua     540
aaauaacggu aaauagucga cuagcaacgu ucgaaaacug gcccaaguuc aucaagcaga     600
gacccguuga uuuggcagaa gcgggauuuu auuauaccgg uguggagac cagacacuuu      660 guuucuacug uggugguggu cuaaaagacu gggaagaauc ugacgaaccu ugggaacaac     720
acgcccuuug guucagcaag uguguuuuc uaaauugaa aaaaguaaa gacuuugucg        780 aaaaggucaa acagagggca gacccucucu ugucgcuccc cggaacaagu caagacaaga     840
ccaaagagcu agaagaaccu aaagagcccu gcaguaggac uccagaaaag gcugaaaaga     900
cuacugaaac ggaagcaaca gagaagacuu uguguaaaau cuguuauaaa aacgaacuug     960
guguuguauu cuugccuugu ggacauguug uugcuugugu agauugugcu ucugcuuuga    1020
aaacuugugc ugucuguagg aaaccuuugg aagcgcacagu ucgagcauuu cucucauaau   1080
uuuuccauuc uuuaauuuuc guuucucaga ucuagucaau uugaauuuga uucuugaagg    1140
uuuauuaaaa aguuugugua aaauuauuc uuuucuguu uaggauuag aaguaaaaucu      1200 auuuuauac aaucugagua caaauuccac auacuuuuuu aguuauaagu ugaagcgcu      1260 uaugaaacau acuuuaguu cauuaaugac ugcaaaccau aucuuucgua cacuaauacu     1320
uauuaguuau caagcucucg ugagggaac uuccuuauua gaacauuuua uuauaaaacu     1380
gacacagaga uauaucugua uguuugugug uauguucacu aaguaugcua auaauauaau    1440
aauuuaugaa aaa                                                       1453

<210> SEQ ID NO 21
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 21
```

| | |
|---|---|
| ggugugggag accagacacu uuguuucuac ugugguggug gucuaaaaga cuggaagaa | 60 |
| ucugacgaac cuugggaaca acacgcccuu ugguucagca agugyguuuu ucuaaauuug | 120 |
| aaaaaaggua aagacuuugu cgaaaagguc aaacagaggg cagacccucu cuugucgcuc | 180 |
| cccggaacaa gucaagacaa gaccaaagag cuagaagaac cuaaagagcc ugcaguagg | 240 |
| acuccagaaa aggcugaaaa gacuacugaa acggaagcaa cagagaagac uugugyuaaa | 300 |
| aucuguuaua aaaacgaacu ugguguugua uucuugccuu uggacaugu uguugcuugu | 360 |
| guagauugug cuucugcuuu gaaaacuugu gcugucugua ggaaaccuuu ggaagcgaca | 420 |
| guucgagcau uu | 432 |

<210> SEQ ID NO 22
<211> LENGTH: 524
<212> TYPE: RNA
<213> ORGANISM: Artificial Sequence
<220> FEATURE:
<223> OTHER INFORMATION: Synthetic Polynucleotide

<400> SEQUENCE: 22

| | |
|---|---|
| auggugagca agggcgagga gcuguucacc ggggugguc ccauccuggu cgagcuggac | 60 |
| ggcgacguaa acgccacaa guucagcgug uccggcgagg gcgagggcga ugccaccuac | 120 |
| ggcaagcuga cccugaaguu caucugcacc accggcaagc ugcccgugcc cuggcccacc | 180 |
| cucgugacca cccugaccua cggcgugcag ugcuucagcc gcuaccccga ccacaugaag | 240 |
| cagcacgacu ucuucaaguc cgccaugccc gaaggcuacg uccaggagcg caccaucuuc | 300 |
| uucaaggacg acggcaacua caagacccgc gccgagguga aguucgaggg cgacacccug | 360 |
| gugaaccgca ucgagcugaa gggcaucgac uucaaggagg acggcaacau ccuggggcac | 420 |
| aagcuggagu acaacuacaa cagccacaac gucauauaca uggccgacaa gcagaagaac | 480 |
| ggcaucaagg ugaacuucaa gauccgccac aacaucgagg acgg | 524 |

<210> SEQ ID NO 23
<211> LENGTH: 521
<212> TYPE: RNA
<213> ORGANISM: Artificial Sequence
<220> FEATURE:
<223> OTHER INFORMATION: Synthetic Polynucleotide

<400> SEQUENCE: 23

| | |
|---|---|
| cuaaugcauu gcguuguuca gauacaaacg uacgugcagu ucaguucagu ucaguucucg | 60 |
| uaucgcuagu uugucggagc aauugguuca cuugguauuu ggggcgauuu uaacguguuu | 120 |
| uuuacgaagg aucuuauaaa aaucaugcag uguuacagca ucauauuuuu ugguacugag | 180 |
| aaggcaugaa aaugaaucaa acauuuccca caaucagcag uuacucugau cagacagaca | 240 |
| auaaccccaa acauaaaagu uuuuugaag uaaacgucaa caauuccgca uuggaggcga | 300 |
| gacuagaaac auuugacaau uggccaagca cacaacuauc caaggaagcg cucgcgucug | 360 |
| ccgguuuuga auacacugga caagaugaca uuguuugug ucguuucugu aagauagaag | 420 |
| gauacaauug gguaucugga gaugauccaa uggcagacca ucgagaaugg agccugacu | 480 |
| guccuuuuau uagaacugua gagaacggca ggucugggag u | 521 |

<210> SEQ ID NO 24
<211> LENGTH: 522
<212> TYPE: RNA
<213> ORGANISM: Artificial Sequence
<220> FEATURE:
<223> OTHER INFORMATION: Synthetic Polynucleotide

<400> SEQUENCE: 24

```
aauagaaacg cagauacuug uggacuguac ggcauagagg uucuuccaaa uucccucccg      60
gaggacagga gauccauuga uuugcaacag uugggaaucc acaaaggaag uggaccacac     120
aaccaggaua aaauaacggu aaauagucga cuagcaacgu ucgaaaacug gcccaagucc     180
aucaagcaga acccguuga uuuggcagaa gcgggauuuu auuauaccgg uguggagac       240 cagacacuuu guuucuacug uggugguggu cuaaaagacu gggaagaauc ugacgaaccu     300
ugggaacaac acgcccuuug guucagcaag uguguuuuc uaaauuugaa aaaagguaaa     360
gacuuugucg aaaaggucaa acagagggca gacccucucu ugucgcuccc cggaacaagu     420
caagacaaga ccaaagagcu agaagaaccu aaagagcccu gcaguaggac uccagaaaag     480
gcugaaaaga cuacugaaac ggaagcaaca gagaagacuu ug                       522
```

<210> SEQ ID NO 25
<211> LENGTH: 521
<212> TYPE: RNA
<213> ORGANISM: Artificial Sequence
<220> FEATURE:
<223> OTHER INFORMATION: Synthetic Polynucleotide

<400> SEQUENCE: 25

```
uguaaaaucu guuauaaaaa cgaacuuggu guuguauucu ugccuugugg acauguuguu      60
gcuuguguag auugugcuuc ugcuuugaaa acuugugcug ucguaggaa accuuuggaa      120 gcgacaguuc gagcauuucu cucauaauuu uuccauucuu uaauuuucgu uucucagauc     180
uagucaauuu gaauuugauu cuugaagguu uauuaaaaag uuuugucaaa aauuauucuu     240
uucuuguuuu aggauuagaa guaaaucuau uuuuauacaa ucugaguaca aauuccacau     300
acuuuuuuag uuauaaguuu gaagcgcuua ugaaacauac uuuuaguuca uuaaugacug     360
caaaccauau cuuucguaca cuaauacuua uuaguuauca agcucucgug aguggaacuu     420
ccuuauuaga acauuuuauu auaaaacuga cacagagaua uaucuguaug uuugugugua     480
uguucacuaa guaugcuaau aauauaauaa uuuaugaaaa a                        521
```

<210> SEQ ID NO 26
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 26

```
gaugagugac ugcagaaucu uuguuccgc ugagguuguu ggcuugaaca cuaggaaaga      60
gguuaugaac cuugguaacu acacaccauu ugaugcagca agcgugaucu ucuaaauuag    120
uuagcaauga aagccuuugu cuaaggggug aaccagcgug ccgagccucu cuagccccuc    180
ucugacacaa gucaaaacau gaucauuggg cuuguagagc cucgagggu cugcaguaga     240 acaccagacc aggcuggaaa gucuccugaa acagauccac cagaggagac guaguugaaa    300
auccguuaua gaaucgaacu ucgcguugua ccacggcuuu auaggcaacc aguuacuugu    360
cuagauugug cuucagcuac uagaaauugu gcugaaagga ggaaaccacu gcaagggcug    420
gaacggggau ua                                                        432
```

<210> SEQ ID NO 27
<211> LENGTH: 432
<212> TYPE: RNA

<213> ORGANISM: Artificial Sequence
<220> FEATURE:
<223> OTHER INFORMATION: Synthetic Polynucleotide

<400> SEQUENCE: 27

| aguguuuuaa | aaacgcsccu | uuuuggcuac | uguaguugua | guucaaaaa | cugugaagaa | 60 |
| ucggacgauc | auugggaaca | acacgcgcuu | ucguucagca | aguggacuuc | uagaacuuug | 120 |
| aaaaaaggua | augacacagu | ugaggagguc | aaacugaggg | cacacgcucu | cuugucgcag | 180 |
| ccgggaacaa | gacaagacau | gaccaauaag | auagaaggac | auacaggcuc | auugaguagg | 240 |
| gcucagaaaa | aaggucaaaa | gacuacugau | acggaaccc | cacagcacac | auugucuacu | 300 |
| aucgaccua | agaucugacc | uggaguuaua | uucuugaccu | guggaccugu | uguggcuugc | 360 |
| cuagauugag | cuacugacau | gaaaauaucu | gaugucugua | ggaagcauac | ggaagcgacg | 420 |
| gcaugcgcau | uu | | | | | 432 |

<210> SEQ ID NO 28
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 28

| guugugggag | accagucuau | guggugcaac | uauacuggug | gucauaaaaa | cuggacaua | 60 |
| ucagacguac | cucggguaga | acccgcgcuu | gggucagga | agugguuuu | gcuaaaaaug | 120 |
| auauaagcuc | aagacuuugu | cgaaaacgac | aaccagaggg | aagaacaucu | cuugucgcuc | 180 |
| uccgaaacaa | cucaaaacaa | gaccaaaaag | auagagguau | cggaagagcc | cagcaguagg | 240 |
| agccucgaac | aggcugaaga | gacuacuaag | agggacgcua | cagagcacac | uuugacuaag | 300 |
| aucuguuaaa | aagacgagcu | ugguuuaguu | uucuuaccug | guugacuugu | uguugccugu | 360 |
| cgaaaugug | cuucugcuuu | gaaaacuugu | gcugucugua | ggcaaccuuu | ggaaucgaca | 420 |
| guuagcgcau | uc | | | | | 432 |

<210> SEQ ID NO 29
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 29

| gguguaggag | accagacacu | cuguuucuac | ugaggugcuc | gucuaggaga | ccguguagaa | 60 |
| ucuaacgaac | cuugggaaca | acacgcccuu | uguuucagcc | agugugauuu | ucaaaugug | 120 |
| aaauaagguu | aagacuuugu | cggcaagguc | aaacagaggc | cagaccaucu | cuugacgcgc | 180 |
| cccguaacaa | gucaagaaaa | uaccaacgag | cuacaagaac | auaaagagcg | cugcaguagg | 240 |
| acuccgaaaa | agguugagaa | gacuacugaa | agggaagcaa | gagguaaggc | uauguguuaa | 300 |
| uucuuuuaua | aagacuuucu | ugguugcgua | uauuugccuu | guggccaugu | uguugcucgu | 360 |
| guaagguuguu | cuucugcuua | agcaacuugu | gcuguaugua | gcaaacuuuu | gccagcggca | 420 |
| guucgagcau | uu | | | | | 432 |

<210> SEQ ID NO 30
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 30

| | |
|---|---|
| ggugugggag agcagacacu ucguuucuac aguggugcg gucuaaaaga cugggaagaa | 60 |
| ucugacgagc cuugcgaaca acaggcacuu ggguucagca aguuugcuuu ucugaauuug | 120 |
| aaaaaauguu aagaccuugu cggaaagguc aaacagaggc cagacccucu cuuguggcac | 180 |
| cccugaacaa gucaagacaa gaccacaggc cgagaagaac cuaaagagcc cugcagcagg | 240 |
| acuccagaca aggcugaaaa gacuacugca acggaagcag gagaaaaggc uuuguguaaa | 300 |
| aucuguucua aaaacgaacu uggaguugua uucggccuu guggccaugu uguugcgggu | 360 |
| gucgauugug cgucugcuuu gaauacuugu gcuguccuua ggaaaccuuu ggaagcgaca | 420 |
| guucgagcaa uu | 432 |

<210> SEQ ID NO 31
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 31

| | |
|---|---|
| ggugugggag accagacacu uuguuucuac ugugauggug gucuaaaaga cugggaaaaa | 60 |
| ucugacgaac cuugggauaca acacggccuu gguucagca agugugucuu uauaaauuug | 120 |
| aaaaaaggua aagacuuugg cgaaaagguc aagcagaggg caaucccucu cuugucgcac | 180 |
| cccggaacaa gucaagacaa gaccaaagag cuagacgaac cuaaagagcc cugcaguagg | 240 |
| acuccagaaa aggcugaaaa gacuacugaa acggaagcca cagagaagac uuuguguaaa | 300 |
| aucuguuaua aaaccaacu ugauguuguu uucuugccau gggacauuu uguugcuugu | 360 |
| ggagcuugug cuucugcuuu gaaaacuugu gcugucugua ggaaaccuuu ggaagcgaca | 420 |
| guucgagcau uc | 432 |

<210> SEQ ID NO 32
<211> LENGTH: 200
<212> TYPE: RNA
<213> ORGANISM: Artificial Sequence
<220> FEATURE:
<223> OTHER INFORMATION: Synthetic Polynucleotide

<400> SEQUENCE: 32

| | |
|---|---|
| gcagacccuc ucuugucgcu ccccggaaca agucaagaca agaccaaaga gcuagaagaa | 60 |
| ccuaaagagc ccugcaguag gacuccagaa aaggcugaaa agacuacuga acggaagca | 120 |
| acagagaaga cuuuguguaa aaucuguuau aaaaacgaac uggguguugu auucuugccu | 180 |
| guggacaug uuguugcuug | 200 |

<210> SEQ ID NO 33
<211> LENGTH: 150
<212> TYPE: RNA
<213> ORGANISM: Artificial Sequence
<220> FEATURE:
<223> OTHER INFORMATION: Synthetic Polynucleotide

<400> SEQUENCE: 33

| | |
|---|---|
| gaacaaguca agacaagacc aaagagcuag aagaaccuaa agagcccugc aguaggacuc | 60 |
| cagaaaaggc ugaaaagacu acugaaacgg aagcaacaga gaagacuuug uguaaaaucu | 120 | guuauaaaaa cgaacuuggu guuguauucu 150

<210> SEQ ID NO 34
<211> LENGTH: 100
<212> TYPE: RNA
<213> ORGANISM: Artificial Sequence
<220> FEATURE:
<223> OTHER INFORMATION: Synthetic Polynucleotide

<400> SEQUENCE: 34
gcuagaagaa ccuaaagagc ccugcaguag gacuccagaa aaggcugaaa agacuacuga 60
aacggaagca acagagaaga cuuuguguaa aaucuguuau 100

<210> SEQ ID NO 35
<211> LENGTH: 50
<212> TYPE: RNA
<213> ORGANISM: Artificial Sequence
<220> FEATURE:
<223> OTHER INFORMATION: Synthetic Polynucleotide

<400> SEQUENCE: 35
aguaggacuc cagaaaaggc ugaaaagacu acugaaacgg aagcaacaga 50

<210> SEQ ID NO 36
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 36
gaaaaggcug aaaagacuac ugaaa 25

<210> SEQ ID NO 37
<211> LENGTH: 1564
<212> TYPE: RNA
<213> ORGANISM: Artificial Sequence
<220> FEATURE:
<223> OTHER INFORMATION: Synthetic Polynucleotide

<400> SEQUENCE: 37
uuuuucauaa auuauuauau uauuagcaua cuuagugaac auacacacaa acauacagau 60
auaucucugu gucaguuuua uaauaaaaug uucuaauaag gaaguccac ucacgagagc 120 uugauaacua auaaguauua guguacgaaa gauaugguuu gcagcauua augaacuaaa 180 aguauguuuc auaagcgcuu caaacuuaua acuaaaaaag uauguggaau uuguacucag 240
auuguauaaa aauagauuua cuucuaaucc uaaaacaaga aaagaauaau uuugacaaa 300 acuuuuuaau aaaccuucaa gaaucaaauu caaauugacu agaucugaga acgaaaauu 360 aaagaaugga aaauuauga gagaaaugcu cgaacugucg cuuccaaagg uuccuacag 420 acagcacaag uuuucaaagc agaagcacaa ucuacacaag caacaacaug uccacaaggc 480
aagaauacaa caccaaguuc guuuuuauaa cagauuuuac acaaagucuu cucuguugcu 540
uccguuucag uagucuuuuc agccuuuucu ggaguccuac ugcagggcuc uuuagguucu 600
ucuagcucuu uggucuuguc uugacuuguu ccggggagcg acaagagagg gucugcccuc 660
uguuugaccu uuucgacaaa gucuuuaccu uuuucaaau uuagaaaaac acacuugcug 720
aaccaaaggg cguguuguuc ccaagguucg ucagauucuu cccagucuuu uagaccacca 780
ccacaguaga aacaaaugu cuggucuccc acaccgguau aauaaaaucc cgcuucugcc 840
aaaucaacgg gucucugcuu gaugggacuug ggccaguuuu cgaacguugc uagucgacua 900

| | |
|---|---|
| uuuaccguua uuuuauccug guugugugu ccacuuccuu uguggauucc caacuguugc | 960 |
| aaaucaaugg aucuccuguc cuccgggagg gaauuuggaa gaaccucuau gccguacagu | 1020 |
| ccacaaguau cugcguuucu auuacuccca gaccugccgu ucucuacagu ucuaauaaaa | 1080 |
| ggacagucag gacuccauuc ucgauggucu gccauuggau caucuccaga uacccaauug | 1140 |
| uauccuucua ucuuacagaa acgacacaaa acaaugucau cuugccagu guauucaaaa | 1200 |
| ccggcagacg cgagcgcuuc cuuggauagu uguguggcuug gccaauuguc aaauguucuc | 1260 |
| agucucgccu ccaaugcgga auuguugacg uuuacuucaa aaaaacuuuu auguuugggg | 1320 |
| uuauugucuc ucugaucaga guaacugcug auugugggaa auguuugauu cauuuucaug | 1380 |
| ccuucucagu accaaaaaau augaugcugu aacacugcau gauuuuauaa agauccuucg | 1440 |
| uaaaaaacac guuaaaaucg cccccaaauac caagugaacc aauugcuccg acaaacuagc | 1500 |
| gauacgagaa cugaacugaa cugaacugca cguacguuug uaucugaaca acgcaaugca | 1560 |
| uuag | 1564 |

<210> SEQ ID NO 38
<211> LENGTH: 1453
<212> TYPE: RNA
<213> ORGANISM: Artificial Sequence
<220> FEATURE:
<223> OTHER INFORMATION: Synthetic Polynucleotide

<400> SEQUENCE: 38

| | |
|---|---|
| uuuuucauaa auuauuauau uauuagcaua cuuagugaac auacacacaa acauacagau | 60 |
| auaucucugu gucaguuuua uaauaaaaug uucuaauaag gaaguuccac ucacgagagc | 120 |
| uugauaacua auaaguauua guguacgaaa gauauggguuu gcagucauua augaacuaaa | 180 |
| aguauguuuc auaagcgcuu caaacuuaua acuaaaaaag uauguggaau uuguacucag | 240 |
| auuguauaaa aauagauuua cuucaauucc uaaaacaaga aaagaauaau uuuugacaaa | 300 |
| acuuuuuaau aaaccuucaa gaaucaaauu caaauugacu agaucugaga acgaaaauu | 360 |
| aaagaaugga aaaauuauga gagaaaugcu cgaacugucg cuuccaaagg uuuccuacag | 420 |
| acagcacaag uuucaaagc agaagcacaa ucuacacaag caacaacaug uccacaaggc | 480 |
| aagaauacaa caccaaguuc guuuuuauaa cagauuuuac acaaagucuu cucuguugcu | 540 |
| uccguuucag uagcuuuuc agccuuuucu ggaguccuac ugcagggcuc uuuagguucu | 600 |
| ucuagcucuu uggucuuguc uugacuuguu ccggggagcg acaagagagg gucugccuc | 660 |
| uguuugaccu uuucgacaaa gucuuuaccu uuuuucaaau uuagaaaaac acacuugcug | 720 |
| aaccaaaggg cguuguuc ccaagguucg ucagauucuu cccagucuuu uagaccacca | 780 |
| ccacaguaga aacaaagugu cugguucuccc acaccgguau aauaaaaucc cgcuucugcc | 840 |
| aaaucaacgg gucucugcuu gauggacuug ggccaguuuu cgaacguugc uagucgacua | 900 |
| uuuaccguua uuuuauccug guugugugu ccacuuccuu uguggauucc caacuguugc | 960 |
| aaaucaaugg aucuccuguc cuccgggagg gaauuuggaa gaaccucuau gccguacagu | 1020 |
| ccacaaguau cugcguuucu auuacuccca gaccugccgu ucucuacagu ucuaauaaaa | 1080 |
| ggacagucag gacuccauuc ucgauggucu gccauuggau caucuccaga uacccaauug | 1140 |
| uauccuucua ucuuacagaa acgacacaaa acaaugucau cuugccagu guauucaaaa | 1200 |
| ccggcagacg cgagcgcuuc cuuggauagu uguguggcuug gccaauuguc aaauguucuc | 1260 |
| agucucgccu ccaaugcgga auuguugacg uuuacuucaa aaaaacuuuu auguuugggg | 1320 |

| | |
|---|---|
| uuauugucug ucugaucaga guaacugcug auugugggaa auguuugauu cauuuucaug | 1380 |
| ccaacuagcg auacgagaac ugaacugaac ugaacugcac guacguuugu aucugaacaa | 1440 |
| cgcaaugcau uag | 1453 |

<210> SEQ ID NO 39
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 39

| | |
|---|---|
| aaaugcucga acugucgcuu ccaaagguuu ccuacagaca gcacaaguuu ucaaagcaga | 60 |
| agcacaaucu acacaagcaa caacauqucc acaaggcaag aauacaacac caaguucguu | 120 |
| uuuauaacag auuuuacaca aagucuucuc uguugcuucc guucaguag ucuuuucagc | 180 |
| cuuuucugga guccuacugc agggcucuuu agguucuucu agcucuuugg ucuugucuuu | 240 |
| acuuguuccg gggagcgaca agagagqquc ugcccucugu uugaccuuuu cgacaaaguc | 300 |
| uuuaccuuuu uucaaauuua gaaaaacaca cuugcugaac caaagggcgu guuguuccca | 360 |
| agguucguca gauucuuccc agucuuuuag accaccacca caguagaaac aaagugucug | 420 |
| gucucccaca cc | 432 |

<210> SEQ ID NO 40
<211> LENGTH: 524
<212> TYPE: RNA
<213> ORGANISM: Artificial Sequence
<220> FEATURE:
<223> OTHER INFORMATION: Synthetic Polynucleotide

<400> SEQUENCE: 40

| | |
|---|---|
| ccguccucga uguuguggcg gaucuugaag uucaccuuga ugccguucuu cugcuugucg | 60 |
| gccaugauau agacguugug gcuguuguag uuguaccca gcuugugccc caggauguuu | 120 |
| ccguccuccu ugaagucgau gcccuucagc ucgaugcggu ucaccagggu gucgcccucg | 180 |
| aacuucaccu cggcgcgggu cuuguaguug ccgucguccu ugaagaagau ggugcgcucc | 240 |
| uggacguagc cuucgggcau ggcggacuug aagaagucgu gcugcuucau guggucgggg | 300 |
| uagcggcuga agcacugcac gccguagguc agggguguca cgaggguggg ccagggcacg | 360 |
| ggcagcuugc cgguggugca gaugaacuuc aggqucagcu ugccguaggu ggcaucgccc | 420 |
| ucgcccucgc cggacacgcu gaacuugugg ccguuuacgu cgccguccag cucgaccagg | 480 |
| augggcacca ccccggugaa cagcucccug cccuugcuca ccau | 524 |

<210> SEQ ID NO 41
<211> LENGTH: 521
<212> TYPE: RNA
<213> ORGANISM: Artificial Sequence
<220> FEATURE:
<223> OTHER INFORMATION: Synthetic Polynucleotide

<400> SEQUENCE: 41

| | |
|---|---|
| acucccagac cugccguucu cuacaguucu aauaaaagga cagucaggac uccauucucg | 60 |
| auggucugcc auuggaucau cuccagauac ccaauuguau ccuucuaucu uacagaaacg | 120 |
| acacaaaaca auqucaucuu guccagugua uucaaaaccg gcagcgcga gcgcuuccuu | 180 |
| ggauaguugu gugcuuggcc aauugucaaa uqucucagu cucgccccca augcggaauu | 240 |
| guugacguuu acuucaaaaa aacuuuuaug uuuggggüua uugucugucu gaucagagua | 300 |

```
acugcugauu gugggaaaug uuugauucau uuucaugccu ucucaguacc aaaaaauaug    360
augcuguaac acugcaugau uuuuauaaga uccuucguaa aaaacacguu aaaaucgccc    420
caaauaccaa gugaaccaau ugcuccgaca aacuagcgau acgagaacug aacugaacug    480
aacugcacgu acguuuguau cugaacaacg caaugcauua g                        521
```

```
<210> SEQ ID NO 42
<211> LENGTH: 522
<212> TYPE: RNA
<213> ORGANISM: Artificial Sequence
<220> FEATURE:
<223> OTHER INFORMATION: Synthetic Polynucleotide

<400> SEQUENCE: 42
caaagucuuc ucuguugcuu ccguuucagu agucuuuuca gccuuuucug gaguccuacu     60
gcagggcucu uuagguucuu cuagcucuuu ggucuugucu ugacuuguuc cggggagcga    120
caagagaggg ucugcccucu guugaccuu uucgacaaag ucuuuaccuu uuucaaauu     180 uagaaaaaca cacuugcuga accaaagggc guguuguucc caagguucgu cagauucuuc    240
ccagucuuuu agaccaccac cacaguagaa acaaagguguc uggucuccca caccgguaua    300
auaaaauccc gcuucugcca aaucaacggg ucucugcuug auggacuugg ccaguuuuc    360 gaacguugcu agcgacuau uuaccguuau uuuauccugg uugugugguc cacuuccuuu    420
guggauuccc aacuguugca aaucaaugga ucuccuguc uccgggaggg aauuuggaag    480
aaccucuaug ccguacaguc cacaaguauc ugcguuuca uu                       522
```

```
<210> SEQ ID NO 43
<211> LENGTH: 521
<212> TYPE: RNA
<213> ORGANISM: Artificial Sequence
<220> FEATURE:
<223> OTHER INFORMATION: Synthetic Polynucleotide

<400> SEQUENCE: 43
uuuuucauaa auuauuauau uauuagcaua cuuagugaac auacacacaa acauacagau     60
auaucucugu gucaguuuua uaauaaaaug uucuaauaag gaaguccac ucacgagagc    120 uugauaacua auaaguauua guguacgaaa gauaugguuu gcagucauua augaacuaaa    180
aguauguuuc uaaagcgcuu caaacuuaua acuaaaaaag uauguggaau uguacucag    240 auuguauaaa aauagauuua cuucuaaucc uaaaacaaga aagaauaau uuugacaaa    300 acuuuuuaau aaaccuucaa gaaucaaauu caaauugacu agaucugaga acgaaaauu    360 aaagaaugga aaauuauga gagaaaugcu cgaacugucg cuuccaaagg uuccuacag    420 acagcacaag uuucaaagc agaagcacaa ucuacacaag caacaacaug uccacaaggc    480
aagaauacaa caccaaguuc guuuuauaa cagauuuuac a                        521
```

```
<210> SEQ ID NO 44
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 44 uaaucccgu uccagcccuu gcaguggguuu ccuccuuuca gcacaauuuc uaguagcuga     60
agcacaaucu agacaaguaa cugguugccu auaaagccgu gguacaacgc gaaguucgau    120
```

| | |
|---|---|
| ucuauaacgg auuuucaacu acgucuccuc uggugaucu guuucaggag acuuccagc | 180 |
| cuggucuggu guucuacugc agaccucucg aggcucuaca agcccaauga ucauguuuug | 240 |
| acuuguguca gagaggggcu agagaggcuc ggcacgcugg uucaccccuu agacaaaggc | 300 |
| uuucauugcu aacuaauuua gaagaucacg cuugcugcau caaauggugu guaguuacca | 360 |
| agguucauaa ccucuuuccu aguguucaag ccaacaaccu cagcggaaac aaagauucug | 420 |
| cagucacuca uc | 432 |

<210> SEQ ID NO 45
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 45

| | |
|---|---|
| aaaugcgcau gccgucgcuu ccguaugcuu ccuacagaca ucagauauuu ucaugucagu | 60 |
| agcucaaucu aggcaagcca caacaggucc acaggucaag aauauaacac caggucagau | 120 |
| cuuaggucag auaguagaca augugugcug uggggguucc guaucaguag ucuuuugacc | 180 |
| uuuuucucga gcccuacuca augagccugu auguccuucu aucuuauugg ucaugucuug | 240 |
| ucuuguuccc ggcugcgaca agagagcgug ugcccucagu ugaccuccu caacugugu | 300 |
| auuaccuuuu uucaaaguuc uagaaguccc cuugcugaac gaaagcgcgu guuguuccca | 360 |
| augaucgucc gauucuucac aguuuugaa acuacaacua caguagccaa aaggggcgu | 420 |
| uuuuaaaaca cu | 432 |

<210> SEQ ID NO 46
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 46

| | |
|---|---|
| gaaugcgcua acugucgauu ccaaagguug ccuacagaca gcacaaguuu ucaaagcaga | 60 |
| agcacaauuu cgacaggcaa caacaaguca accagguaag aaaacuaaac caagcucguc | 120 |
| uuuuuaacag aucuuagcua aagugugcuc uguagcgucc cucuaguag ucucuucagc | 180 |
| cuguucgagg cuccuacugc uggcucuuc cgauaccucu aucuuuugg ucuuguuug | 240 |
| aguuguuucg gagagcgaca agagauguuc uuccccucgg uugucguuuu cgacaaaguc | 300 |
| uugagcuuau aucauuuuua gcaaaacaca cuuccugaac ccaagcgcgg guucuacccg | 360 |
| agguacgucu gauaugccc aguuuuuaug accaccagua uaguugcacc acauagacug | 420 |
| gucucccaca ac | 432 |

<210> SEQ ID NO 47
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 47

| | |
|---|---|
| aaaugcucga acugccgcug gcaaaaguuu gcuacauaca gcacaaguug cuuaagcaga | 60 |
| agaacaaccu acacgagcaa caacauggcc acaaggcaaa uauacgacac caagaaaguc | 120 |
| uuuauaaaag aauuaacaca uagccuuacc ucuugcuucc cuuucaguag ucuucucaac | 180 |

| | |
|---|---|
| cuuuuccgga guccuacugc agcgcucuuu auguucuugu agcucguugg uauuuucuug | 240 |
| acuuguuacg gggcgcguca agagaugguc uggccucugu ugaccuugc cgacaaaguc | 300 |
| uuaaccuuau uucacauuuu gaaaaucaca cuggcugaaa caaagggcgu guuguuccca | 360 |
| agguucguua gauucuacac ggucuccuag acgagcaccu caguagaaac agagugucug | 420 |
| gucuccuaca cc | 432 |

```
<210> SEQ ID NO 48
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 48
```

| | |
|---|---|
| aauugcucga acugucgcuu ccaaagguuu ccuaaggaca gcacaaguau ucaaagcaga | 60 |
| cgcacaaucg acaccccgcaa caacauggcc acaaggccag aauacaacuc caaguucguu | 120 |
| uuuagaacag auuuuacaca aagccuuuuc ccugcuucc guugcaguag ucuuuucagc | 180 |
| cuugucugga guccugcugc agggcucuuu agguucuucu cggccugugg ucuugucuug | 240 |
| acuuguucag gggugccaca agagagqquc uggccucugu ugaccuuuc cgacaagguc | 300 |
| uuaacauuuu uucaaauuca gaaaagcaaa cuugcugaac ccaagugccu guuguucgca | 360 |
| aggcucguca gauucuuccc agucuuuuag accgccacca cuguagaaac gaagugucug | 420 |
| cucucccaca cc | 432 |

```
<210> SEQ ID NO 49
<211> LENGTH: 432
<212> TYPE: RNA
<213> ORGANISM: Artificial Sequence
<220> FEATURE:
<223> OTHER INFORMATION: Synthetic Polynucleotide

<400> SEQUENCE: 49
```

| | |
|---|---|
| gaaugcucga acugucgcuu ccaaagguuu ccuacagaca gcacaaguuu ucaaagcaga | 60 |
| agcacaagcu ccacaagcaa caaaaugucc acauggcaag aaaacaacau caaguugguu | 120 |
| uuuauaacag auuuuacaca aagucuucuc uguggcuucc guucaguag ucuuuucagc | 180 |
| cuuuucgga guccuacugc agggcucuuu agguucgucu agcucuuugg ucuugucuug | 240 |
| acuuguuccg gggugcgaca agagagggau ugcccucugc ugaccuuuu cgccaaaguc | 300 |
| uuuaccuuuu uucaaauuua uaaagacaca cuugcugaac caaaggccgu guguaccca | 360 |
| agguucguca gauuuuuccc agucuuuuag accaccauca caguagaaac aaaguguucug | 420 |
| gucucccaca cc | 432 |

```
<210> SEQ ID NO 50
<211> LENGTH: 200
<212> TYPE: RNA
<213> ORGANISM: Artificial Sequence
<220> FEATURE:
<223> OTHER INFORMATION: Synthetic Polynucleotide

<400> SEQUENCE: 50
```

| | |
|---|---|
| caagcaacaa cauguccaca aggcaagaau acaacaccaa guucguuuuu auaacagauu | 60 |
| uuacacaaag ucuucucugu ugcuuccguu ucaguagcu uucagccuu uucuggaguc | 120 |
| cuacugcagg gcucuuuagg uucuucagc ucuuuggucu ugcuugacu uguuccgggg | 180 |

```
agcgacaaga gagggucugc                                              200

<210> SEQ ID NO 51
<211> LENGTH: 150
<212> TYPE: RNA
<213> ORGANISM: Artificial Sequence
<220> FEATURE:
<223> OTHER INFORMATION: Synthetic Polynucleotide

<400> SEQUENCE: 51
agaauacaac accaaguucg uuuuuauaac agauuuuaca caaagucuuc ucuguugcuu    60
ccguuucagu agucuuuuca gccuuuucug gaguccuacu gcagggcucu uuagguucuu   120
cuagcucuuu ggucuugucu ugacuuguuc                                   150

<210> SEQ ID NO 52
<211> LENGTH: 100
<212> TYPE: RNA
<213> ORGANISM: Artificial Sequence
<220> FEATURE:
<223> OTHER INFORMATION: Synthetic Polynucleotide

<400> SEQUENCE: 52
auaacagauu uuacacaaag ucuucucugu ugcuuccguu ucaguagucu uuucagccuu    60
uucuggaguc cuacugcagg gcucuuuagg uucuucuagc                        100

<210> SEQ ID NO 53
<211> LENGTH: 50
<212> TYPE: RNA
<213> ORGANISM: Artificial Sequence
<220> FEATURE:
<223> OTHER INFORMATION: Synthetic Polynucleotide

<400> SEQUENCE: 53
ucuguugcuu ccguuucagu agucuuuuca gccuuuucug gaguccuacu              50

<210> SEQ ID NO 54
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 54
uuucaguagu cuuuucagcc uuuuc                                         25
```

CONTROL OF COLEOPTERAN INSECTS

RELATED APPLICATION

This application claims the benefit under 35 U.S.C. § 119(e) of U.S. Provisional Application No. 62/737,041, filed Sep. 26, 2018, the content of which is incorporated herein by reference in its entirety.

BACKGROUND

The Colorado potato beetle (*Leptinotarsa decemlineata*) is a major pest of the potato crop. The annual costs of controlling the Colorado potato beetle are estimated to be in the tens of millions of dollars, with projected annual costs of crop loss reaching billions of dollars if the Colorado potato beetle is left uncontrolled. Moreover, controlling the Colorado potato beetle is complicated by its resistance to numerous chemicals and insecticides. Accordingly, new ways of controlling the Colorado potato beetle are needed.

SUMMARY

The present disclosure provides, in some aspects, compositions, genetic constructs, and methods for controlling Colorado potato beetle infestation. To reduce our dependence on broad-spectrum chemical insecticides and their related problems, reduced-risk pesticides are required. A new technology that offers the promise of a reduced risk approach to insect pest control is RNA interference (RNAi). In some embodiments, the present disclosure provides RNAi-based technologies that can mitigate Colorado potato beetle damage by delivering ribonucleic acid (RNA) interference (RNAi) molecules that target (e.g., bind to) and interfere with the messenger RNA (mRNA) of a Colorado potato beetle Inhibitor of Apoptosis (IAP) gene.

Apoptosis is an evolutionarily conserved pathway of cell suicide that is critical for normal cell development and homeostasis. The key regulators of apoptosis are IAPs. IAPs were discovered in insect baculoviruses (Cydia pomonella granulosis virus and Orgyia pseudotsugata nuclear polyhedrosis virus) and have since been identified in many other organisms, such as mosquito iridescent viruses, insects, yeast, and human. Many IAPs block apoptosis when they are overexpressed in cells of other species. Knockdown expression of IAPs through RNA interference typically induces apoptosis. See, e.g., Pridgeon J W et al. *J Med Entomol* 2008; 45(3): 414-420.

Laboratory studies have confirmed that oral delivery of RNA molecules whose mode of action is through the RNAi process (e.g., double-stranded RNA (dsRNA)) are effective for many insect species and hence, topical dsRNA is considered a suitable form of delivery. However, spray-on dsRNA insect pest control technology does not exist today. The cost of production of dsRNA at relatively low price is a major challenge for the Ag-Bio industry. For agricultural pests, transgenic plants that can express insecticidal dsRNA may protect the plants from insect herbivory. However, not all countries are receptive to genetically-modified crops, and spray-on application of dsRNA is being considered as an alternative delivery method of protection.

To identify targets for RNAi knockdown, whole genome information was used to identify the appropriate gene sequence for IAP in the target species (*Leptinotarsa decemlineata*), which when silenced selectively, controls these key pests, without adversely affecting non-target species in the potato agriculture ecosystem. Given a DNA sequence of interest and a rule set of design criteria for the output sequences, a propriety computational algorithm was combined with publicly available RNAi design tools, to create output sequences that meet these criteria. The original/initial region selected to design the dsRNA was identified by searching comprehensive sequence databases for *Tribolium* and *Drosophila* genomes (e.g., Flybase, SnapDragon, Beetlebase, etc.). The publicly available E-RNAi tool, that can be used to design dsRNA using a predicted siRNA-based approach, was combined with proprietary algorithms to create the design workflow. This design workflow was then used to create specific long dsRNA sequences of a (a) desired length (b) desired percent identity to original sequence (by introducing random mutations), and (c) by sectioning the initial IAP gene sequence into multiple fragments.

In some embodiments, the RNAi molecules comprise single-stranded RNA (ssRNA), and in some embodiments, the RNAi molecules comprise double-stranded RNA (dsRNA) or partially dsRNA. In still other embodiments, the RNAi molecules may be single-stranded RNA molecules with secondary structure containing significant double-stranded character, such as, but not limited to, hairpin RNA. The present disclosure provides RNA, for example single stranded RNA (ssRNA), small interfering (siRNA), micro RNA (miRNA), messenger RNA (mRNA), short hairpin (shRNA) or double stranded RNA (dsRNA) for targeting IAP mRNA.

IAP RNA, in some embodiments, is effective for reducing IAP expression in an insect, stunting of larvae, inhibiting growth, reproduction (e.g., fertility and/or fecundity) and/or repair of the insect, killing of the larvae or the insect, and decreasing feeding of the insect. Accordingly, one aspect of the present disclosure provides a method for controlling an insect comprising delivering (e.g., contacting) an effective amount of an IAP-targeting RNA with a plant and/or an insect. IAP RNA is particularly useful for controlling a Coleopteran insect (e.g., Colorado potato beetle), thereby reducing and/or preventing infestation of certain plants (e.g., a potato) that are a major food source for humans.

Some aspects of the present disclosure also provide cell-free methods of producing IAP-targeting RNA, the method comprising: (a) incubating in a reaction mixture cellular RNA, and a ribonuclease under conditions appropriate for the production of 5' nucleoside monophosphates (5' NMPs); (b) eliminating the ribonuclease; and (c) incubating the reaction mixture, or in a second reaction mixture, the 5' NMPs, a polyphophospate kinase, a polyphosphate, a polymerase, and a DNA (also referred to a DNA template) under conditions appropriate for the production of the IAP-targeting RNA from the DNA.

Also provided herein are compositions comprising an IAP-targeting RNA. In some embodiments, the composition comprising an IAP-targeting RNA further comprises an additive, for example, a chemical, a pesticide, a surfactant, a biological, or other non-pesticidal ingredient. In some embodiments, IAP-targeting RNA is provided in an expression vector. In some embodiments, an IAP-targeting RNA is provided in a plant or a plant cell.

It should be understood that an "RNAi molecule targeting IAP" encompasses "RNAi molecules targeting mRNA encoded by IAP." A RNAi molecule is considered to target a gene of interest if the RNAi molecule binds to (e.g., transiently binds to) and inhibits (reduces or blocks) translation of the mRNA, e.g., due to the mRNA being degraded. In some embodiments, if there are epigenetic changes, a RNAi molecule may inhibit expression of the mRNA encoded by the gene of interest. It should also be understood that in some embodiments, the polynucleotide is a double-stranded RNA (e.g., dsRNA GS3) that inhibits expression of a coding region of the gene (e.g., IAP). In other embodiments, the polynucleotide is a DNA sequence that encodes a dsRNA. In yet other embodiments, the polynucleotide is an antisense RNA. It should be understood that the sequences disclosed herein as DNA sequences can be converted from a DNA sequence to an RNA sequence by replacing each thymidine with a uracil.

DETAILED DESCRIPTION

Figure 1A:
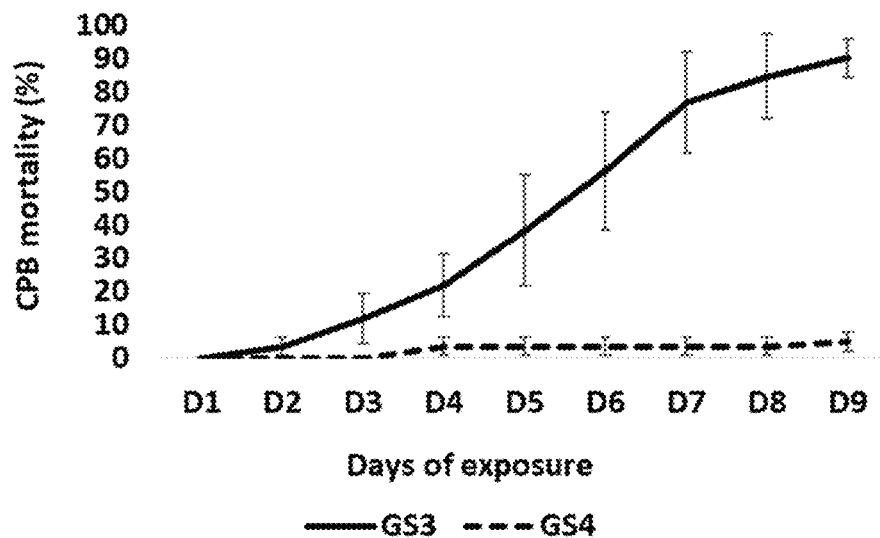
FIGS. 1A-1B include graphs showing the percent mortality of Colorado potato beetles (CPBs) (FIG. 1A) and percent leaf disc consumption by CPBs (FIG. 1B) following a nine-day exposure of the CPBs to either an IAPRNAi (GS3) composition of the present disclosure (containing a double-stranded RNA (dsRNA) targeting IAP mRNA) or to a control RNAi (GS4) composition (10 μg/cm² concentration of RNAi).

According to some aspects of the present disclosure, RNAi molecules (e.g., dsRNAs) targeting IAP are effective at interfering with the mRNA encoded by an IAP gene in Coleopteran insect cells, thereby reducing or eliminating translation of the mRNA (e.g., into its corresponding protein). Accordingly, in some aspects, the present disclosure provides compositions and methods for controlling Coleopteran infestations by contacting any portion of a plant (e.g., roots, tubers, stem, branches, leaves, flower, etc.), ground (e.g., soil, dirt, grass, etc.), Coleopteran insect and/or diet (e.g., food and/or water ingested by) of the insect with an RNAi molecule as provided herein. Also provided herein are cell-free methods of synthesizing RNAi molecules that target IAP gene products (mRNA).

A Coleopteran insect, as used herein, refers to a Coleopteran insect in any stage of development. In some embodiments, the Coleopteran insect is an insect egg. In some embodiments, the Coleopteran insect is an insect larva. In some embodiments, the Coleopteran insect is an insect pupa. In some embodiments, the Coleopteran insect is an adult insect.

A Coleopteran insect may be any Coleopteran insect of order Coleoptera. Examples of insects of the order Coleoptera include, but are not limited to, *Chrysomelidae* (leaf beetle), *Curculionidae* (snout beetle), *Meloidae* (blister beetle), *Tenebrionidae* (darkling beetle), *Scarabaeidae* (scarab beetle), *Cerambycidae* (Japanese pine sawyer), *Curculionidae* (Chinese white pine beetle), *Nitidulidae* (small hive beetle), *Chrysomelidae* (broad-shouldered leaf beetle), *Cerambycidae* (mulberry longhorn beetle), *Phyllotreta* (flea beetle), *Diabrotica* (corn rootworm) *Chrysomela* (cottonwood leaf beetle), *Hypothenemus* (coffee berry borer), *Sitophilus* (maize weevil), *Epitrix* (tobacco flea beetle), *E. cucumeris* (potato flea beetle), *P. pusilla* (western black flea beetle); *Anthonomus* (pepper weevil), *Hemicrepidus* (wireworms), *Melanotus* (wireworm), *Ceutorhychus* (cabbage seedpod weevil), *Aeolus* (wireworm), *Horistonotus* (sand wireworm), *Sphenophorus* (maize billbug), *S. zea* (timothy billbug), *S. parvulus* (bluegrass billbug), *S. callosus* (southern corn billbug); *Phyllophaga* (white grubs), *Chaetocnema* (corn flea beetle), *Popillia* (Japanese beetle), *Epilachna* (Mexican bean beetle), *Cerotoma* (bean leaf beetle), *Epicauta* (blister beetle), *Chrysomelidae* (alligator weed flea beetle) and any combination thereof.

Further, the Coleopteran insect may be any species of *Leptinotarsa*. *Leptinotarsa* species include, but are not limited to, *Leptinotarsa decemlineata* (Colorado potato beetle), *Leptinotarsa behrensi*, *Leptinotarsa collinsi*, *Leptinotarsa defecta*, *Leptinotarsa haldemani* (Haldeman's green potato beetle), *Leptinotarsa heydeni*, *Leptinotarsa juncta* (false potato beetle), *Leptinotarsa lineolata* (burrobrush leaf beetle), *Leptinotarsa peninsularis*, *Leptinotarsa rubiginosa*, *Leptinotarsa texana*, *Leptinotarsa tlascalana*, *Leptinotarsa tumamoca*, and *Leptinotarsa typographica*.

RNAi Molecule Targeting Inhibitor of Apoptosis (IAP)

RNAi molecules targeting IAP have been identified through examination of IAP mRNA and in vivo (e.g., plant/field) testing. Such RNAi molecules targeting IAP are useful for controlling Coleopteran insects (e.g., Colorado potato beetles), for example, by inhibiting or reducing expression of IAP, and consequently, by increasing insect mortality, as well as decreasing growth, reproduction (e.g., fertility and/or fecundity), and/or feeding (e.g., eating and/or drinking) of Coleopteran insects.

Expression of a gene in a cell (e.g., insect cell), for example, is considered to be inhibited or reduced through contact with an RNAi molecule if the level of mRNA and/or protein encoded by the gene is reduced in the cell by at least 10% relative to a control cell that has not been contacted with the RNAi molecule. For example, delivering to a cell (e.g., contacting a cell) with an RNAi molecule (e.g., dsRNA) targeting IAP may result in a reduction (e.g., by at least 10%) in the amount of RNA transcript and/or protein (e.g., encoded by the IAP gene) compared to a cell that is not contacted with RNAi molecular targeting IAP.

In some embodiments, RNAi molecules of the present disclosure specifically inhibit expression of an IAP gene without biologically relevant or biologically significant off-target effects (no relevant or significant change in the expression of non-IAP genes). In some embodiments, an RNAi molecule specifically inhibits (reduces or blocks) translation of an IAP protein by specifically inhibiting expression of (e.g., degrading) an IAP mRNA (e.g., IAP mRNA of SEQ ID NO: 19) that encodes the IAP protein. Specific inhibition of an IAP gene includes a measurable reduction in IAP gene expression (e.g., IAP mRNA expression, and/or IAP protein expression) or a complete lack of detectable gene expression (e.g., IAP mRNA expression, and/or IAP protein expression).

In some embodiments, RNAi molecules of the present disclosure specifically inhibit expression of an IAP gene without biologically relevant or biologically significant off-target effects (no relevant or significant change in the expression of non-IAP genes). In some embodiments, an RNAi molecule specifically inhibits the expression of an IAP protein by specifically inhibiting an mRNA that encodes an IAP protein (e.g., IAP mRNA of SEQ ID NO: 19). Specific inhibition of an IAP gene involves a measurable reduction in IAP gene expression (e.g., IAP mRNA expression, and/or IAP protein expression) or a complete lack of detectable gene expression (e.g., IAP mRNA expression, and/or IAP protein expression).

RNAi molecules targeting IAP provided herein, in some embodiments, are designed to have complementarity to IAP mRNA of a Coleopteran insect, e.g., a Colorado potato beetle. An example of a DNA sequence encoding Colorado potato beetle IAP is provided in the sequence of SEQ ID NO: 1. An example of an mRNA sequence encoding Colorado potato beetle IAP is provided in the sequence of SEQ ID NO: 19. Examples of Colorado potato beetle IAP mRNA sequences targeted by an RNAi molecule of the present disclosure encoding are provided in the sequences of SEQ ID NO: 19-21 and 23-36. Examples of a RNA molecules targeting IAP are provided in the sequences of SEQ ID NO: 37-39 and 41-54.

In some embodiments, the RNAi molecule targeting IAP provided herein is designed to have complementarity to IAP mRNA of a Coleopteran insect, e.g., a *Chrysomelidae* (a leaf beetle), a *Curculionidae* (a snout beetle), a *Meloidae* (a blister beetle), *Tenebrionidae* (a darkling beetle), a *Scarabaeidae* (a scarab beetle), a *Cerambycidae* (a japanese pine sawyer), a *Curculionidae* (a Chinese white pine beetle), a *Nitidulidae* (a small hive beetle), a *Chrysomelidae* (a broad-shouldered leaf beetle), a *Cerambycidae* (a mulberry longhorn beetle), *C. scripta* (cottonwood leaf beetle), *H. hampei* (coffee berry borer), *S. Zeamais* (maize weevil), f. *hirtipennis* (tobacco flea beetle), *F. cucumeris* (potato flea beetle), *P. cruciferae* (crucifer flea beetle) and *P. pusilla* (western black flea beetle), *A. eugenii* (pepper weevil), *H. memnonius* (wireworms), *M. communis* (wireworm), *C. assimilis* (cabbage seedpod weevil), *P. striolata* (striped flea beetle), *A. mellillus* (wireworm), *A. mancus* (wheat wireworm), *H. uhlerii* (sand wireworm), *S. maidis* (maize billbug), *S. zeae* (timothy billbug), *S. parvulus* (bluegrass billbug), and *S. callosus* (southern corn billbug), *Phyllophaga* spp. (White grubs), *C. pulicaria* (corn flea beetle), *P. japonica* (Japanese beetle), *F. varivestis* (Mexican bean beetle), *C. trifurcate* (Bean leaf beetle), *F. pestifera* and *F. lemniscata* (Blister beetles), *Oulema melanapus* (Cereal leaf beetle), *Hypera postica* (Alfalfa weevil), *Dendroctonus* (Mountain Pine beetle), *Agrilus* (Emarald Ash Borer), *Hylurgopinus* (native elm bark beetle), *Scolytus* (European elm bark beetle) and/or a *Chrysomelidae* (an alligator weed flea beetle).

In some embodiments, the RNAi molecule targeting IAP provided herein is designed to have complementarity to IAP mRNA of a *Leptinotarsa* insect, e.g., a *Leptinotarsa decemlineata* (a Colorado potato beetle), a *Leptinotarsa behrensi*, a *Leptinotarsa collinsi*, a *Leptinotarsa defecta*, a *Leptinotarsa haldemani* (a Haldeman's green potato beetle), a *Leptinotarsa heydeni*, a *Leptinotarsa juncta* (a false potato beetle), a *Leptinotarsa lineolata* (a burrobrush leaf beetle), a *Leptinotarsa peninsularis*, a *Leptinotarsa rubiginosa*, a *Leptinotarsa texana*, a *Leptinotarsa tlascalana*, a *Leptinotarsa tumamoca*, and/or a *Leptinotarsa typographica.*

A double-stranded RNA (dsRNA) of the present disclosure, in some embodiments, comprises a first strand that binds to (e.g., is at least partially complementary to or is wholly complementary to) a messenger RNA (mRNA) encoded by a Coleopteran IAP gene, and a second strand that is complementary to the first strand.

dsRNA may comprise RNA strands that are the same length or different lengths. In some embodiments, a dsRNA comprises a first strand (e.g., an antisense strand) that is the same length as a second strand (e.g., a sense strand). In some embodiments, a dsRNA comprises a first strand (e.g., an antisense strand) that is a different length than a second strand (e.g., a sense strand). A first strand may be about 1%, 2%, 3%, 4%, 5%, 10%, 15%, 20%, or more than 20% longer than a second strand. A first strand may be 1-5, 2-5, 2-10, 5-10, 5-15, 10-20, 15-20, or more than 20 nucleotides longer than a second strand.

dsRNA molecules can also be assembled from a single oligonucleotide in a stem-loop structure, wherein self-complementary sense and antisense regions of the RNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active RNAi molecule capable of mediating RNAi. An RNAi molecule may comprise a 3' overhang at one end of the molecule, The other end may be blunt-ended or have also an overhang (5' or 3'). When the RNAi molecule comprises an overhang at both ends of the molecule, the length of the overhangs may be the same or different.

A single-stranded RNA of the present disclosure, in some embodiments, comprises a strand that binds to a mRNA encoded by a Coleopteran IAP gene.

RNAi molecules targeting IAP as provided herein may vary in length. It should be understood that, in some embodiments, while a long RNA (e.g., dsRNA or ssRNA) molecule is applied (e.g., to a plant) as the insecticide, after entering cells this dsRNA is cleaved by the Dicer enzyme into shorter double-stranded RNA fragments having a length of, for example, 15 to 25 nucleotides. Thus, RNAi molecules of the present disclosure may be delivered as 15 to 25 nucleotide fragments, for example, or they may be delivered as longer double-stranded nucleic acids (e.g., at least 100 nucleotides).

Thus, in some embodiments, RNAi molecules targeting IAP comprise 15-1564 nucleotides (ssRNA) or nucleotide base pairs (dsRNA). For example, an RNAi molecule of the present disclosure may comprise 15-1000, 15-950, 15-900, 15-850, 15-800, 15-750, 15-700, 15-650, 15-600, 15-500, 15-450, 15-400, 15-350, 15-300, 15-250, 15-200, 15-150, 15-100, 15-50, 19-1000, 18-950, 18-900, 18-850, 18-800, 18-750, 18-700, 18-650, 18-600, 18-500, 18-450, 18-400, 18-350, 18-300, 18-250, 18-200, 18-180, 18-100, 18-50, 19-1000, 19-950, 19-900, 19-850, 19-800, 19-750, 19-700, 19-650, 19-600, 19-500, 19-450, 19-400, 19-350, 19-300, 19-250, 19-200, 19-190, 19-100, 19-50, 20-1000, 20-950, 20-900, 20-850, 20-800, 20-750, 20-700, 20-650, 20-600, 20-500, 20-450, 20-400, 20-350, 20-300, 20-250, 20-200, 20-200, 20-100, 20-50, 15211000, 21-950, 21-900, 21-850, 21-800, 21-750, 21-700, 21-650, 21-600, 21-500, 21-450, 21-400, 21-350, 21-300, 21-250, 21-210, 21-210, 21-100, 21-50, 22-1000, 22-950, 22-900, 22-850, 22-800, 22-750, 22-700, 22-650, 22-600, 22-500, 22-450, 22-400, 22-350, 22-300, 22-250, 22-220, 22-220, 22-100, 22-50, 23-1000, 23-950, 23-900, 23-850, 23-800, 23-750, 23-700, 23-650, 23-600, 23-500, 23-450, 23-400, 23-350, 23-300, 23-250, 23-230, 23-230, 23-100, 23-50, 24-1000, 24-950, 24-900, 24-850, 24-800, 24-750, 24-700, 24-650, 24-600, 24-500, 24-450, 24-400, 24-350, 24-300, 24-250, 24-240, 24-240, 24-100, 24-50, 25-1000, 25-950, 25-900, 25-850, 25-800, 25-750, 25-700, 25-650, 25-600, 25-500, 25-450, 25-400, 25-350, 25-300, 25-250, 25-250, 25-250, 25-100, or 25-50 nucleotides or nucleotide base pairs. In some embodiments, RNAi molecules targeting IAP comprise or consist of at least 15, at least 16, at least 17, at least 18, at least 19, at least 20, at least 25, at least 50, at least 200, at least 300, at least 400, at least 500, at least 600, at least 700, at least 800, at least 900, or at least 1000 nucleotides or nucleotide base pairs.

In some embodiments, an RNAi molecule targeting IAP comprises or consists of a sequence that is complementary to an mRNA or a segment of an mRNA encoded by a Coleopteran IAP gene. In some embodiments, an RNAi molecule targeting IAP comprises or consists of a sequence that is complementary to an mRNA or a segment of an mRNA encoded by a DNA sequence of any one of SEQ ID NOS: 1-3 or 5-18. In some embodiments, an RNAi molecule targeting IAP comprises or consists of a sequence that is complementary to an mRNA encoded by a DNA sequence of SEQ ID NO: 1.

In some embodiments, an RNAi molecule targeting IAP comprises or consists of a sequence that is complementary to an mRNA encoded by a region or segment of a Coleopteran IAP DNA. In some embodiments, an RNAi molecule targets an mRNA encoded by a 5' region or segment of a Coleopteran IAP DNA. A 5' region of a Coleopteran IAP DNA may comprise or consist of any sequence encompassed by nucleotides 1 to 600, nucleotides 10 to 600, nucleotides 25 to 600, nucleotides 50 to 600, nucleotides 100 to 600, nucleotides 150 to 600, nucleotides 200 to 600, nucleotides 250 to 600, nucleotides 300 to 600, nucleotides 350 to 600, nucleotides 400 to 600, nucleotides 450 to 600, or nucleotides 500 to 600 of the IAP DNA (e.g., nucleotides 1-600 of SEQ ID NO: 1). In some embodiments, an RNAi molecule targets an mRNA encoded by a central region or segment of a Coleopteran IAP DNA. A central region of a Coleopteran IAP DNA may comprise or consist of any sequence encompassed by nucleotides 400 to 1200, nucleotides 450 to 1200, nucleotides 500 to 1200, nucleotides 550 to 1200, nucleotides 600 to 1200, nucleotides 650 to 1200, nucleotides 700 to 1200, nucleotides 850 to 1200, nucleotides 900 to 1200, nucleotides 950 to 1200, nucleotides 1000 to 1200, nucleotides 1050 to 1200, or nucleotides 1100 to 1200 of the IAP DNA (e.g., nucleotides 400-1200 of SEQ ID NO: 1). In some embodiments, an RNAi molecule targets an mRNA encoded by a 3' region or segment of a Coleopteran IAP DNA. A 3' region of a Coleopteran IAP DNA may comprise or consist of any sequence encompassed by nucleotides 1000 to 1564, nucleotides 1050 to 1564, nucleotides 1100 to 1564, nucleotides 1150 to 1564, nucleotides 1200 to 1564, nucleotides 1250 to 1564, nucleotides 1300 to 1564, nucleotides 1350 to 1564, nucleotides 1400 to 1564, nucleotides 1450 to 1564, or nucleotides 1500 to 1564, of the IAP DNA (e.g., nucleotides 1000-1564 of SEQ ID NO: 1).

It should be understood that the term gene encompasses coding and non-coding nucleic acid. Thus, in some embodiments, an IAP gene encodes an mRNA that comprises a 5' untranslated region, an open reading frame, and a 3' untranslated region. Thus, an RNAi molecule herein, in some embodiments, binds to a 5' untranslated region, an open reading frame, and/or a 3' untranslated region of an mRNA.

In some embodiments, an RNAi molecule targeting IAP comprises or consists of an RNA sequence of any one of SEQ ID NOS: 37-39 or 41-54. In some embodiments, an RNAi molecule targeting IAP comprises or consists of an RNA sequence of SEQ ID NO: 37.

In some embodiments, an RNAi molecule targeting IAP comprises or consists of a sequence that is complementary to a RNA sequence of any one of SEQ ID NOS: 19-21 or 23-36. In some embodiments, an RNAi molecule targeting IAP comprises or consists of a sequence that is complementary to a RNA sequence of SEQ ID NO: 19.

In some embodiments, RNAi molecules targeting IAP comprise or consist of a (at least one) contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence encoded by a Coleopteran IAP gene. In some embodiments, the IAP gene comprises a DNA sequence of SEQ ID NO: 1. In some embodiments, RNAi molecules targeting IAP comprise or consist of a (at least one) contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence encoded by a DNA sequence of any one of SEQ ID NOS: 1-3 or 5-18.

In some embodiments, RNAi molecules targeting IAP comprise or consist of a (at least one) contiguous sequence that is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence encoded by a Coleopteran IAP gene. In some embodiments, the IAP gene comprises a DNA sequence of SEQ ID NO: 1. In some embodiments, RNAi molecules targeting IAP comprise or consist of a (at least one) contiguous sequence that is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence encoded by a DNA sequence of any one of SEQ ID NOS: 1-3 or 5-18.

In some embodiments, RNAi molecules targeting IAP comprise or consist of a (at least one) contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence of any one of SEQ ID NOS: 37-39 or 41-54. In some embodiments, RNAi molecules targeting IAP comprise or consist of a contiguous sequence that has 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence of SEQ ID NO: 37.

In some embodiments, RNAi molecules targeting IAP comprise or consist of a (at least one) contiguous sequence is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence of any one of SEQ ID NOS: 19-21 or 23-36. In some embodiments, RNAi molecules targeting IAP comprise or consist of a contiguous sequence is 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence of SEQ ID NO: 19.

In some embodiments, RNAi molecules targeting IAP comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of any one of SEQ ID NOS: 37-39 or 41-54. In some embodiments, RNAi molecules targeting IAP comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of SEQ ID NO: 37.

In some embodiments, RNAi molecules targeting IAP comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of any one of SEQ ID NOS: 19-21 or 23-36. In some embodiments, RNAi molecules targeting IAP comprise or consist of at least 15, at least 16, at least 17, at least 18, at least 19, at least 20, at least 25, at least 50, at least 75, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides or nucleotide base pairs having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of SEQ ID NO: 19.

In some embodiments, RNAi molecules targeting IAP comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of any one of SEQ ID NOS: 37-39 or 41-54. In some embodiments, RNAi molecules targeting IAP comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% identity (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% identity) to an RNA sequence or segment of an RNA sequence of SEQ ID NO: 37.

In some embodiments, RNAi molecules targeting IAP comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of any one of SEQ ID NOS: 19-21 or 23-36. In some embodiments, RNAi molecules targeting IAP comprise or consist of 10 to 25, 10 to 24, 10 to 23, 10 to 22, 10 to 21, 10 to 20, 11 to 25, 11 to 24, 11 to 23, 11 to 22, 11 to 21, 11 to 20, 12 to 25, 12 to 24, 12 to 23, 12 to 22, 12 to 21, 12 to 20, 13 to 25, 13 to 24, 13 to 23, 13 to 22, 13 to 21, 13 to 20, 14 to 25, 14 to 24, 14 to 23, 14 to 22, 14 to 21, 14 to 20, 15 to 25, 15 to 24, 15 to 23, 15 to 22, 15 to 21, 15 to 20, 16 to 25, 16 to 24, 16 to 23, 16 to 22, 16 to 21, 16 to 20, 17 to 25, 17 to 24, 17 to 23, 17 to 22, 17 to 21, 17 to 20, 18 to 25, 18 to 24, 18 to 23, 18 to 22, 18 to 21, or 18 to 20 contiguous nucleotides having 70% to 100% complementary (e.g., 70% to 100%, 75% to 100%, 80% to 100%, 85% to 100%, 90% to 100%, 95% to 100%, 96% to 100%, 97% to 100%, 98% to 100%, 99% to 100%, 80%, 85%, 90%, 95%, 96%, 97%, 98%, 99%, or 100% complementary) to an RNA sequence or segment of an RNA sequence of SEQ ID NO: 19.

The "percent identity" of two nucleic acid sequences (e.g., RNAi molecules targeting IAP provided herein and any one of, for example, SEQ ID NOS: 1, 19, or 37) may be determined by any method known in the art. The variants provided herein, in some embodiments, contain randomly placed mutations with the four nucleotides (A, U, G, C) selected at an approximately equal probability for a given mutation. In some embodiments, these mutations might be distributed either over a small region of the sequence, or widely distributed across the length of the sequence. In some embodiments, the percent identity of two nucleic acid sequences is determined using the algorithm of Karlin and Altschul, *Proc. Natl. Acad. Sci. USA* 87:2264-68, 1990, modified as in Karlin and Altschul, *Proc. Natl. Acad. Sci. USA* 90:5873-77, 1993. Such an algorithm is incorporated into the NBLAST and XBLAST programs (version 2.0) of Altschul et al. J. Mol. Biol. 215:403-10, 1990. BLAST nucleotide searches can be performed with the NBLAST program, score=100, wordlength-12 to obtain guide sequences homologous to a target nucleic acid. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NB LAST) can be used.

The polynucleotides provided herein, such as RNAi molecules targeting IAP, in some embodiments, are designed to have at least one silencing element complementary (e.g., wholly (100%) or partially (less than 100%, e.g., 90% to 99%) complementary) to a segment of a sequence of IAP mRNA of a Coleopteran insect, e.g., a Colorado potato beetle. In some embodiments, polynucleotides comprise at least one silencing element that is essentially identical or essentially complementary to IAP mRNA of a Coleopteran insect. In some embodiments, the polynucleotides comprise 2 to 5, to 10, 2 to 20, 2 to 20, 2 to 40, or 2 to 50 silencing elements. In some embodiments, the polynucleotides comprise at least 2, at least 3, at least 4, at least 5, at least 6, at least 7, at least 8, at least 9, at least 10, at least 15, at least 20, at least 25, at least 30, at least 35, at least 40, at least 45 or at least 50 silencing elements.

RNAi molecules targeting IAP provided herein may be of any form of RNA, including single-stranded RNA (ssRNA) and double-stranded RNA (dsRNA). Non-limiting examples of single-stranded RNA include mRNA, micro RNA (miRNA) (e.g., artificial miRNA (amiRNA)), small interfering RNA (siRNA), piwi-interacting RNA (piRNA), and antisense RNA. Double-stranded RNA includes wholly double-stranded molecules that do not contain a single-stranded region (e.g., a loop or overhang), as well as partially double-stranded molecules that contain a double-stranded region and a single-stranded region (e.g., a loop or overhang). Further, the RNAi molecules may be single-stranded RNA molecules with secondary structure containing significant double-stranded character, such as, but not limited to, hairpin RNA. Thus, RNAi molecules targeting IAP, in some embodiments, may be short hairpin RNA (shRNA).

In some embodiments, RNAi molecules targeting IAP comprise dsRNA, ssRNA, siRNA, miRNA (e.g., amirRNA), piRNA, mRNA, or shRNA. In some embodiments, RNAi molecules targeting IAP comprise more than one form of RNA. For example, the RNAi molecules targeting IAP may comprise ssRNA and dsRNA. In some embodiments, RNAi molecules targeting IAP comprise a hybrid with RNA and DNA. In some embodiments, RNAi molecules targeting IAP comprise amiRNAs processed from a long precursor transcript of nonprotein-coding RNA, that is partially self-complementary to mediate silencing of target mRNAs. amiRNAs are designed, in some embodiments, by replacing the mature 21 nucleotide miRNA sequences within pre-miRNA with 21 nucleotide long fragments derived from the target gene (*Frontiers in Plant Science*, Sebastian et al., 2017). An amiRNA may have a length of, for example, at least 18 to 500 nucleotides, at least 21 to 500 nucleotides, at least 50 to 500 nucleotides, at least 100 to 500 nucleotides, or at least 200 to 500 nucleotides.

RNAi molecules targeting IAP may be provided as a mixture of RNAi molecules targeting IAP, for example, a mixture of RNAi molecules targeting IAP having different sequences. Any number of distinct RNAi molecules targeting IAP may be provided in a mixture of RNAi molecules targeting IAP. In some embodiments, the mixture of RNAi molecules targeting IAP comprises at least 2, at least 3, at least 4, at least 5, at least 6, at least 7, at least 8, at least 9, or at least 10 distinct (having different sequences/nucleotide compositions) RNAi molecules targeting IAP.

In some embodiment, RNAi molecules targeting IAP are provided as a mixture of RNAi molecules that are complementary (wholly or partially) to different segments of an mRNA encoded by an IAP gene (e.g., comprising a sequence of SEQ ID NO: 1). In some embodiment, RNAi molecules targeting IAP are provided as a mixture of RNAi molecules that are complementary (wholly or partially) to different segments of an RNA sequence of SEQ ID NO: 19. Any number of RNAi molecules targeting IAP that are complementary to different segments of an mRNA (e.g., comprising a sequence of SEQ ID NO: 19) encoded by an IAP gene (e.g., comprising a sequence of SEQ ID NO: 1) may be provided in a mixture of RNAi molecules targeting IAP. In some embodiments, the mixture of RNAi molecules targeting IAP comprises at least 2, at least 3, at least 4, at least 5, at least 6, at least 7, at least 8, at least 9, or at least 10 RNAi molecules targeting IAP. In some embodiments, the mixture of RNAi molecules targeting IAP comprises 2 to 5, or 2 to 10 RNAi molecules targeting IAP.

In some embodiments, RNAi molecules targeting IAP provided herein may have one or more mismatches compared with the corresponding sequence of IAP mRNA (e.g., SEQ ID NO: 19). A region of complementarity on RNAi molecule targeting IAP may have up to 1, up to 2, up to 3, up to 4, etc. mismatches provided that it maintains the ability to form complementary base pairs with IAP mRNA under appropriate hybridization conditions. Alternatively, a region of complementarity on RNAi molecules targeting IAP may have no more than 1, no more than 2, no more than 3, or no more than 4 mismatches provided that it maintains the ability to form complementary base pairs with IAP mRNA under appropriate hybridization conditions. In some embodiments, if there is more than one mismatch in a region of complementarity, they may be positioned consecutively (e.g., 2, 3, 4, or more in a row), or interspersed throughout the region of complementarity provided that the RNAi molecule targeting IAP maintains the ability to form complementary base pairs with IAP mRNA under appropriate hybridization conditions.

RNAi molecules targeting IAP may be modified in various ways to improve or control specificity, stability, delivery, bioavailability, degradation, resistance to nuclease degradation, base-pairing properties, RNA distribution, and cellular uptake, and other features relevant to its use. See, e.g., Bramsen et al., *Nucleic Acids Res.*, 2009, 37, 2867-2881; Bramsen and Kjems, *Frontiers in Genetics*, 3 (2012): 1-22. Accordingly, in some embodiments, RNAi molecules targeting IAP may include one or more (at least one) suitable modifications. In some embodiments, a modified RNAi molecule targeting IAP has a modification in its base, sugar (e.g., ribose, deoxyribose), or phosphate group.

RNAi molecules targeting IAP produced by the methods provided herein may be modified as described herein. In some embodiments, RNAi molecules targeting IAP is produced according to a method described herein and subsequently modified. In some embodiments, RNAi molecules targeting IAP are produced according to a method described herein using a modified starting material. In some embodiments, the modified starting material is a modified nucleobase. In some embodiments, the modified starting material is a modified nucleoside. In some embodiments, the modified starting material is a modified nucleotide.

In some embodiments, modified RNAi molecules targeting IAP comprise a backbone modification. In some embodiments, backbone modification results in a longer half-life for the RNA due to reduced degradation (e.g., nuclease-mediated degradation). This in turn results in a longer half-life. Examples of suitable backbone modifications include, but are not limited to, phosphorothioate modifications, phosphorodithioate modifications, p-ethoxy modifications, methylphosphonate modifications, methylphosphorothioate modifications, alkyl- and aryl-phosphates (in which the charged phosphonate oxygen is replaced by an alkyl or aryl group), alkylphosphotriesters (in which the charged oxygen moiety is alkylated), peptide nucleic acid (PNA) backbone modifications, and locked nucleic acid (LNA) backbone modifications. These modifications may be used in combination with each other and/or in combination with phosphodiester backbone linkages.

Alternatively or additionally, RNAi molecules targeting IAP may comprise other modifications, including modifications at the base or sugar moiety. Examples include RNA having sugars that are covalently attached to low molecular weight organic groups other than a hydroxyl group at the 3' position and other than a phosphate group at the 5' position (e.g., a 2'-O-alkylated ribose), or RNA having sugars such as arabinose instead of ribose. RNA also embraces substituted purines and pyrimidines such as C-5 propyne modified bases (Wagner et al., *Nature Biotechnology* 14:840-844, 1996). Other purines and pyrimidines include, but are not limited to, 5-methylcytosine, 2-aminopurine, 2-amino-6-chloropurine, 2,6-diaminopurine, and hypoxanthine. Other such modifications are well known to those of skill in the art.

RNAi molecules that comprise a nucleotide sequence complementary to all or a segment of the target sequence can be designed and prepared using any suitable methods. In some embodiments, an RNAi molecule may be designed with assistance from comprehensive sequence databases, such as those known for *Tribolium* and *Drosophila* genetics (e.g., Flybase, SnapDragon, Beetlebase, etc.). In some embodiments, a sequence database is utilized to determine off-target effects of a designed RNAi molecule (e.g., as in Arziman, Z., Horn, T., & Boutros, M. (2005). E-RNAi: a web application to design optimized RNAi constructs. *Nucleic Acids Research*, 33 (Web Server issue), W582-W588. doi:10.1093/nar/gki468.)

Methods of Use

Aspects of the present disclosure, in some embodiments, provide methods for controlling a Coleopteran insect infestation comprising delivering to a plant or Coleopteran insect (e.g., Colorado potato beetle) an effective amount of an RNAi molecule targeting IAP (or a composition comprising an RNAi molecule targeting IAP). In some embodiments, the method of delivery comprises applying to a surface of a plant or Coleopteran insect, a composition comprising the RNAi molecule. In some embodiments, a composition comprising an RNAi molecule targeting IAP is a solid or liquid (e.g., solution, suspension, or emulsions). Non limiting examples include emulsifiable concentrates, concentrate solutions, low concentrate solutions, ultra-low volume concentrate solutions, water soluble concentrate solutions, water soluble liquid solutions, baits (paste, gel, liquid, solid or injectable), smoke, fog, invert emulsions, flowables, aerosols, homogenous and non-homogenous mixtures, suspensions (water and oil based), dust, powders (wettable or soluble), granules (water-dispersible or dry flowables), pellets, capsules, fumigants, encapsulated or micro-encapsulation formulations, or any combinations thereof.

In some embodiments, a compositing comprising an RNAi molecule targeting IAP may be applied as a concentrate, spray (after dilution or concentrate), fog, in furrow, seed treatment, drench, drip, insect diet, bait, or any other forms suited for applying to a furrow. The RNAi molecule targeting IAP described herein may be delivered to any portion of a plant, including, but are not limited to, leaf, stem, flower, fruit, shoot, root, seed, tuber, anther, stamen, and/or pollen. In some embodiments, RNAi is delivered mechanically, through high pressure spray or sand blasting. In some embodiments, a composition comprises an RNAi molecules and at least one additive selected from adjuvants, attractants, sterilizing agents, growth-regulating substances, carriers or diluents, stabilizers, and/or pesticidal agent(s)

(e.g., insecticides, fungicides, and/or herbicides). Pesticidal agents include, for example, other dsRNA targeting genes distinct from IAP, patatins, plant lectins, phytoecdysteroids, cry proteins, vegetative insecticidal proteins (vip), cytolytic proteins (cyt), biotin-binding proteins, protease inhibitors, chitinases, organic compounds, or any combination thereof. Non-pesticidal agents may also be used (e.g. adjuvants, such as antifoaming agents, buffers, compatibility agents, drift control additives, emulsifiers, extenders, invert emulsifiers, plant penetrants, safeners, spreaders, stickers, surfactants, thickeners, and wetting agents).

A composition, in some embodiments, include a mixture of an RNAi molecule targeting IAP and at least one of a variety of agricultural chemicals, insecticides, miticides, fungicides, pesticidal agents and/or biopesticidal (e.g., microbial, PIP, and/or biochemical) agents, such as Spiromesifen, Spirodiclofen, Spirotetramat, Pyridaben, Tebufenpyrad, Tolfenpyrad, Fenpyroximate, Flufenerim, Pyrimidifen, Fenazaquin, Rotenone, Cyenopyrafen, Hydramethylnon, Acequinocyl, Fluacrypyrim, Aluminium phosphide, Calcium phosphide, Phosphine, Zinc phosphide, Cyanide, Diafenthiuron, Azocyclotin, Cyhexatin, Fenbutatin oxide, Propargite, Tetradifon, Bensultap, Thiocyclam, Thiosultap-sodium, Flonicamid, Etoxazole, Clofentezine, Diflovidazin, Hexythiazox, Chlorfluazuron, Bistrifluron, Diflubenzuron, Flucycloxuron, Flufenoxuron, Hexaflumuron, Lufenuron, Novaluron, Noviflumuron, Teflubenzuron, Triflumuron, Buprofezin, Cyromazine, Hydroprene, Kinoprene, Methoprene, Fenoxycarb, Pyriproxyfen, Pymetrozine, Pyrifluquinazon, Chlorfenapyr, Tralopyril, methyl bromide and/or other alkyl halides, Chloropicrin, Sulfuryl fluoride, Benclothiaz, Chinomethionat, Cryolite, Methylneodecanamide, Benzoximate, Cymiazole, Fluensulfone, Azadirachtin, Bifenazate, Amidoflumet, Dicofol, Plifenate, Cyflumetofen, Pyridalyl, *Beauveria* bassiana GHA, Sulfoxaflor, Spinetoram, Spinosad, Spinosad, Emamectin benzoate, Lepimectin, Milbemectin, Abamectin, Methoxyfenozide, Chromafenozide, Halofenozide, Tebufenozide, Amitraz, Chlorantraniliprole, Cyantraniliprole, Flubendiamide, alpha-endosulfan, Chlordane, Endosulfan, Fipronil, Acetoprole, Ethiprole, Pyrafluprole, Pyriprole, Indoxacarb, Metaflumizone, Acrinathrin, Allethrin, Allethrin-cis-trans, Allethrin-trans, beta-Cyfluthrin, beta-Cypermethrin, Bifenthrin, Bioallethrin, Bioallethrin S-cyclopentenyl, Bioresmethrin, Cycloprothrin, Cyfluthrin, Cyhalothrin, Cypermethrin, Cyphenothrin [(1R)-trans-isomers], Dimefluthrin, Empenthrin [(EZ)-(1R)-isomers], Esfenvalerate, Etofenprox, Fenpropathrin, Fenvalerate, Flucythrinate, Flumethrin, Gamma-cyhalothryn, lambda-Cyhalothrin, Meperfluthrin, Metofluthrin, Permethrin, Phenothrin [(1R)-trans-isomer], Prallethrin, Profluthrin, Protrifenbute, Resmethrin, Silafluofen, tau-Fluvalinate, Tefluthrin, Tetramethrin, Tetramethrin [(1R)-isomers], Tetramethylfluthrin, theta-Cypermethrin, Tralomethrin, Transfluthrin, zeta-Cypermethrin, alpha-Cypermethrin, Deltamethrin, DDT, Methoxychlor, Thiodicarb, Alanycarb, Aldicarb, Bendiocarb, Benfuracarb, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiofanox, Triazamate, Trimethacarb, XMC, Xylylcarb, Chlorpyrifos, Malathion, Acephate, Azamethiphos, Azinphos-ethyl, Azinphos-methyl, Cadusafos, Chlorethoxyfos, Chlorfenvinphos, Chlormephos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fonofos, Fosthiazate, Imicyafos, Isofenphos-methyl, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-ethyl, Profenofos, Propaphos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, Vamidothion Imidacloprid, Thiamethoxam, Acetamiprid, Clothianidin, Dinotefuran, Nitenpyram, Nithiozine, Nicotine, Thiacloprid, cyantraniliprole, carbamates, organophosphates, cyclodiene organochlorines, phenylpyrazoles (fiproles), pyrethroids, pyrethins, DDT Methoxychlor, Neonicotinoids, Nicotine, Sulfoximines, Butenolides, Mesoionics, Spinosyns, Avermectins, Milbemycins, Juvenile hormone analogues, Fenoxycarb, Pyriproxyfen, Alkyl halides, Chloropicrin, Fluorides, Borates, Tarter emetic, Methyl isothiocyanate generators, Pyridine azomethine derivatives, Pyropenes, Clofentezine, Diflovidazin, Hexythiazox, Etoxazole, Diafenthiuron, Organotin miticides, Propargite, Tetradifon, Pyrroles, Dinitrophenols, Sulfuramid, Nereistoxin analogues, Benzoylureas, Buprofezin, Cyromazine, Diacylhydrazines, Amitraz, Hydramethylnon, Acequinocyl, Fluacrypyrim, Bifenazate, METI acaricides and insecticides, Rotenone, Oxadiazines, Semicarbazones, Tetronic and Tetramic acid derivatives, Phosphides, Cyanides, Beta-ketonitrile derivatives, Carboxanilides, Diamides, Flonicamid, Meta-diamides Isoxazolines, Granuloviruses (GVs), Nucleopolyhedroviruses (NPVs), GS-omega/kappa HXTX-Hv1a peptide, Azadirachtin, Benzoximate, Bromopropylate, Chinomethionat, Dicofol, Lime sulfur, Mancozeb, Pyridalyl, Sulfur, Benzimidazoles, Dicarboximides, Pyridines, Pyrimidines, Triazoles, Acylalanines, Pyridine carboxamides, Anilino-pyrimidines, Quinone outside Inhibitors (QoI-fungicides), Phenylpyrroles, Quinolines, Hydroxyanilides, Toluamides, Cyanoacetamide-oximes, Dinitrophenyl crotonates, Phosphonates, Carboxylic Acid Amides (CAA-fungicides), M1 inorganic, M2 inorganic, M3 dithiocarbamates, M4 phthalimides, paraffinic oil, petroleum-based horticultural oils, palmitic oil, steric oil, linoleic oil, oleic oils, canola oil, soybean oil, oregano oil, tagetes oil, balsam fir oil, thyme oil, black pepper oil, mint oil, cedarwood oil, fish oil, jojoba oil, lavadin oil, castor oil, eucalyptus oil, ocimum oil, patchouli oil, citrus oil, artemisia oil, camphor oil, wintergreen oil, methyl eugenol oil, thymol oil, geranium oil, sesame oil, linseed oil, cottonseed oil, lemongrass oil, bergamot oil, mustard oil, orange oil, citronella oil, tea tree oil, neem oil, garlic oil, *Bacillus sphaericus*, *Bacillus thuringiensis* (e.g., *Bacillus thuringiensis* var. *aizawai*, *Bacillus thuringiensis* var. *israelensis*, *Bacillus thuringiensis* var. *kurstaki*, *Bacillus thuringiensis* var. *sphaericus*, *Bacillus thuringiensis* var. *tenebrionensis*) and the insecticidal proteins they produce (e.g., Cry1Ab, Cry1Ac, Cry1Fa, Cry1A.105, Cry2Ab, Vip3A, mCry3A, Cry3Ab, Cry3Bb, Cry34Ab1/Cr35Ab1), *Paenibacillus popilliae*, *Serratia entomophila*, nuclear polyhedrosis viruses, granulosis viruses, non-occluded baculoviruses, *Beauveria* spp, *Metarhizium*, *Entomophaga*, *Zoopthora*, *Paecilomyces fumosoroseus*, *Normuraea*, *Lecanicillium lecanii*, *Nosema*, *Thelohania*, *Vairimorpha*, *Steinernema* spp, *Heterorhabditis* spp or any combination thereof, which may further comprise an active ingredient selected from the group consisting of azinphos-methyl, acephate, isoxathion, isofenphos, ethion, etrimfos, oxydemeton-methyl, oxydeprofos, quinalphos, chlorpyrifos, chlorpyrifos-methyl, chlorfenvin phos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridafen thion, pirimiphos-methyl, fenitrothion, fenthion, phenthoate, flupyrazophos, prothiofos, propaphos, profenofos, phoxime, phosalone, phosmet, formothion, phorate, malathion, mecarbam, mesulfenfos, methamidophos, methidathion, parathion, methyl parathion, monocrotophos, trichlorphon, EPN, isazophos, isamidofos, cadusafos, diamidaphos, dichlofenthion, thionazin, fenamiphos, fosthiazate, fosthietan, phosphocarb, DSP, ethoprophos, alanycarb, aldicarb, isoprocarb, ethiofen carb, carbaryl, carbosulfan, xylylcarb, thiodicarb, pirimicarb, fenobucarb, furathiocarb, propoxur, ben diocarb, benfuracarb, methomyl, metolcarb, XMC, carbofuran, aldoxycarb, oxamyl, acrin athrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cyper-methrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox, cartap, thiocyclam, bensultap, acetamiprid, imidacloprid, clothianidin, dinotefuran, thiacloprid, thiamethoxam, nitenpyram, chlorfluazuron, difluben zuron, teflubenzuron, triflumuron, novaluron, noviflumuron, bistrifluoron, fluazuron, flucy-cloxuron, flufenoxuron, hexaflumuron, lufenuron, chromafen ozide, tebufenozide, halofen ozide, methoxyfen ozide, diofen olan, cyromazine, pyriproxyfen, buprofezin, methop-rene, hydroprene, kinoprene, triazamate, endosulfan, chlorfenson, chlorobenzilate, dicofol, bromopropylate, acetoprole, flpronil, ethiprole, pyrethrin, rotenone, nicotinesulphate, spinosad, finpronil, spirotetramat abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pyrimidifen, fenazaquin, fenothiocarb, fenpyroximate, fluacrypyrim, flu-azinam, flufenzin, hexythiazox, propargite, polynactin complex, milbemectin, lufenuron, mecarbam, methiocarb, mevinphos, halfenprox, azadirachtin, diafenthiuron, indoxacarb, emamectin benzoate, potassium oleate, sodium oleate, chlorfenapyr, tolfenpyrad, pymetrozine, fenoxycarb, hydramethylnon, hydroxy propyl starch, pyridalyl, flufenerim, flubendiamide, flonicamid, metaflumizole, lepimectin, TPIC, albendazole, oxibendazole, oxfendazole, trichlamide, fensulfothion, fenbendazole, levamisole hydrochloride, morantel tartrate, dazomet, metam-sodium, tri-adimefon, hexaconazole, propiconazole, ipconazole, prochloraz, triflumizole, tebuconazole, epoxiconazole, difenoconazole, flusilazole, triadimenol, cyproconazole, metconazole, fluquinconazole, bitertanol, tetraconazole, triti-conazole, flutriafol, penconazole, diniconazole, fenbuconazole, bromuconazole, imibenconazole, simeconazole, myclobutanil, hymexazole, imazalil, furametpyr, thifluzamide, etridiazole, oxpoconazole, oxpoconazole fumarate, pefurazoate, prothioconazole, pyrifenox, fenarimol, nuari-mol, bupirimate, mepanipyrim, cyprodinil, pyrimethanil, metalaxyl, mefenoxam, oxadixyl, benalaxyl, thiophanate, thiophanate-methyl, benomyl, carbendazim, fuberidazole, thiabendazole, manzeb, propineb, zineb, metiram, maneb, ziram, thiuram, chlorothalonil, ethaboxam, oxycarboxin, carboxin, flutolanil, silthiofam, mepronil, dimethomorph, fenpropidin, fenpropimorph, spiroxamine, tridemorph, dodemorph, flumorph, azoxystrobin, kresoximmethyl, metominostrobin, orysastrobin, fluoxastrobin, trifloxystrobin, dimoxystrobin, pyraclostrobin, picoxystrobin, iprodione, procymidone, vinclozolin, chlozolinate, flusulf- amide, dazomet, methyl isothiocyanate, chloropicrin, methasulfocarb, hydroxyisoxazole, potassium hydroxyisoxazole, echlomezol, D-D, carbam, basic copper chloride, basic copper sulfate, copper nonylphenolsulfonate, oxine copper, DBEDC, anhydrous copper sulfate, copper sulfate pentahydrate, cupric hydroxide, inorganic sulfur, wettable sulfur, lime sulfur, zinc sulfate, fentin, sodium hydrogen carbonate, potassium hydrogen carbonate, sodium hypochlorite, silver, edifenphos, tolclofos-methyl, fosetyl, iprobenfos, dinocap, pyrazophos, carpropamid, fthalide, tricyclazole, pyroquilon, diclocymet, fenoxanil, kasugamycin, validamycin, polyoxins, blasticiden S, oxytetracycline, mildiomycin, streptomycin, rape seed oil, machine oil, benthiavalicarbisopropyl, iprovalicarb, propamocarb, diethofencarb, fluoroimide, fludioxanil, fenpiclonil, quinoxyfen, oxolinic acid, chlorothalonil, captan, folpet, probenazole, acibenzolar-S-methyl, tia-dinil, cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichlofluanide, triforine, isoprothiolane, ferimzone, diclomezine, tecloftalam, pencycuron, chinomethionat, iminoctadine acetate, iminoctadine albesilate, ambam, polycarbamate, thiadiazine, chloroneb, nickel dimethyldithiocarbamate, guazatine, dodecylguanidine acetate, quintozene, tolylfluanid, anilazine, nitrothal-isopropyl, fenitropan, dimethirimol, benthiazole, flumetover, mandipropamide, and penthiopyrad, or any combinations thereof.

In some embodiments, an RNAi molecule targeting IAP is supplied in the diet of a Coleopteran insect. For example, an RNAi molecule targeting IAP may be applied topically to a plant, or seeds (e.g. via soaking, coating, dusting or spraying), or cells of a plant may be engineered to express the RNAi molecule. RNAi molecules may also be supplied in another food or water source.

The plant may be any plant that is subject to infestation by a Coleopteran insect. In some embodiments, the plant is a Solanaceous plant (e.g., family Solanaceae). Examples of Solanaceous plants include, but are not limited to, potato plants (*Solanum tuberosum*), buffalo bur plants (*Solanum rostratum*), eggplant plants (*Solanum melongena*), tomato plants (*Solanum lycopersicum*), tobacco plants (*Nicotiana tabacum*), pepper plants (*Capsicum annum*) and woody nightshade plants (*Solanum dulcamara*).

Thus, in some embodiments, the methods comprise delivering to a plant (e.g., a potato plant) with an RNAi molecule targeting IAP, for example, in an effective amount to suppress infestation of the plant by a Coleopteran insect (e.g., Colorado potato beetle). In other embodiments, the methods comprise delivering to a buffalo bur plant with an RNAi molecule targeting IAP, for example, in an effective amount to suppress infestation of the plant by a Coleopteran insect (e.g., Colorado potato beetle). In yet other embodiments, the methods comprise delivering to an eggplant plant with an RNAi molecule targeting IAP, for example, in an effective amount to suppress infestation of the plant by a Coleopteran insect (e.g., Colorado potato beetle). In still other embodiments, the methods comprise delivering to a tomato plant with an RNAi molecule targeting IAP, for example, in an effective amount to suppress infestation of the plant by a Coleopteran insect (e.g., Colorado potato beetle). In further embodiments, the methods comprise delivering to a tobacco plant with an RNAi molecule targeting IAP, for example, in an effective amount to suppress infestation of the plant by a Coleopteran insect (e.g., Colorado potato beetle). In additional embodiments, the methods comprise delivering to a pepper plant with an RNAi molecule targeting IAP, for example, in an effective amount to suppress infestation of the plant by a Coleopteran insect (e.g., Colorado potato beetle).

Delivering to a plant (e.g., a part of a plant) and/or Coleopteran insect an RNAi molecule targeting IAP may include, for example, applying (e.g., soaking, coating, or dusting) the RNAi molecule or a composition comprising the RNAi molecule topically to any portion of a plant (e.g., roots, tubers, stem, branches, leaves, flower, etc), ground (e.g., soil, dirt, grass, etc.), insect and/or diet of the insect. A delivering step may also include genetically engineering cells of a plant to express the RNAi molecule. A delivering step may also include exposing a plant or Coleopteran insect to an organism (e.g., virus, bacteria, fungus, etc.) that has been genetically engineered to express and/or deliver the RNAi molecule to the plant or Coleopteran insect.

An effective amount is the amount of an RNAi molecule targeting IAP required to confer a beneficial effect on infestation (e.g. death, cessation of feeding, inhibition of growth, development or reproduction) by a Coleopteran insect, either alone or in combination with one or more other additives. Beneficial effects include a reduction in infestation, for example, by at least 10%, at least 20%, at least 30%, at least 40%, at least 50%, at least 60%, at least 70%, at least 80%, or at least 90%, relative to a control. In some embodiments, the control is the absence of an insecticide and/or pesticide. In some embodiments, an effective amount of an RNAi molecule targeting IAP completely eliminates Coleopteran insect (e.g., Colorado potato beetle) infestation of a plant.

Effective amounts vary, as recognized by those skilled in the art, depending on the particular plant, the severity of the infestation, the duration of the infestation, previous exposure to insecticides and like factors within the knowledge and expertise of a practitioner. These factors are well known to those of ordinary skill in that art and can be addressed with no more than routine experimentation. It is generally preferred that lower effective concentrations be used, that is, the lowest concentration that provides control of an insect, to increase efficiency and decrease cost.

An effective amount of an RNAi molecule targeting IAP may also vary depending on the method of delivery.

In some embodiments, an effective amount of an RNAi molecule targeting IAP is expressed as micrograms (µg) of RNAi molecule targeting IAP per centimeter squared ($cm^2$) of a surface of a plant or ground (e.g., soil, dirt, grass, etc.), i.e., $\mu g/cm^2$. Thus, in some embodiments, an effective amount of an RNAi molecule targeting IAP comprises 0.001 $\mu g/cm^2$ to 10 $\mu g/cm^2$. In some embodiments, an effective amount of an RNAi molecule targeting IAP comprises 0.001 $\mu g/cm^2$ to 9 $\mu g/cm^2$, 0.001 $\mu g/cm^2$ to 8 $\mu g/cm^2$, 0.001 $\mu g/cm^2$ to 7 $\mu g/cm^2$, 0.001 $\mu g/cm^2$ to 6 $g/cm^2$, 0.001 $\mu g/cm^2$ to 5 $\mu g/cm^2$, 0.001 $\mu g/cm^2$ to 4 $\mu g/cm^2$, 0.001 $\mu g/cm^2$ to 3 $\mu g/cm^2$, 0.001 $\mu g/cm^2$ to 2 $\mu g/cm^2$, 0.001 $\mu g/cm^2$ to 1 $\mu g/cm^2$, 0.001 $\mu g/cm^2$ to 0.1 $\mu g/cm^2$, or 0.001 $\mu g/cm^2$ to 0.01 $\mu g/cm^2$. In some embodiments, an effective amount of an RNAi molecule targeting IAP comprises 0.01 $\mu g/cm^2$ to 10 $\mu g/cm^2$, 0.1 $\mu g/cm^2$ to 10 $\mu g/cm^2$, 1 $\mu g/cm^2$ to 10 $\mu g/cm^2$, 2 $\mu g/cm^2$ to 10 $\mu g/cm^2$, 3 $\mu g/cm^2$ to 10 $\mu g/cm^2$, 4 $\mu g/cm^2$ to 10 $\mu g/cm^2$, 5 $\mu g/cm^2$ to 10 $\mu g/cm^2$, 6 $\mu g/cm^2$ to 10 $\mu g/cm^2$, 7 $\mu g/cm^2$ to 10 $\mu g/cm^2$, 8 $\mu g/cm^2$ to 10 $\mu g/cm^2$, or 9 $\mu g/cm^2$ to 10 $\mu g/cm^2$.

In some embodiments, an effective amount of an RNAi molecule targeting IAP is expressed as grams (g) of RNAi molecule targeting IAP per acre (ac.) of a surface of a plant or ground (e.g., soil, dirt, grass, etc.), i.e., g/ac. Thus, in some embodiments, an effective amount of an RNAi molecule targeting IAP comprises 0.01 g/ac. to 100 g/ac. In some embodiments, an effective amount of an RNAi molecule targeting IAP comprises 0.01 g/ac. to 90 g/ac., 0.01 g/ac. to 80 g/ac., 0.01 g/ac. to 70 g/ac., 0.01 g/ac. to 60 g/ac., 0.01 g/ac. to 50 g/ac., 0.01 g/ac. to 40 g/ac., 0.01 g/ac. to 30 g/ac., 0.01 g/ac. to 20 g/ac., 0.01 g/ac. to 10 g/ac., 0.01 g/ac. to 1 g/ac., or 0.01 g/ac. to 0.1 g/ac. In some embodiments, an effective amount of an RNAi molecule targeting IAP comprises 0.1 g/ac. to 100 g/ac., 1 g/ac. to 100 g/ac., 10 g/ac. to 100 g/ac., 20 g/ac. to 100 g/ac., 30 g/ac. to 100 g/ac., 40 g/ac. to 100 g/ac., 50 g/ac. to 100 g/ac., 60 g/ac. to 100 g/ac., 70 g/ac. to 100 g/ac., 80 g/ac. to 100 g/ac., or 90 g/ac. to 100 g/ac.

In some embodiments, the effectiveness of an RNAi molecule to control Coleopteran insects can be determined using the ability of the RNAi molecule to kill or cause death of an insect or population of insects. The rate of death in a population of insects may be determined by percent mortality (e.g., percent mortality over time). Generally, percent mortality of a population of insects reflects the percentage of insects in said population that have died as a result of the RNAi molecule (e.g., 75% mortality indicates that an RNAi molecule has killed 75% of the total insect population). In some embodiments, percent mortality is measured over time (e.g., over the course of a multi-day exposure of insects to an RNAi molecule). In some embodiments, percent mortality is measured after at least 3, 4, 5, 6, 7, 8, 9, 10, 15, or 20 days of exposure. In some embodiments, an RNAi molecule causes a percent mortality of at least 30%, 40%, 50%, 60%, 70%, 80%, 90%, 95%, 98%, or 100% of a Coleopteran insect population. In some embodiments, at least 30%, 40%, 50%, 60%, 70%, 80%, 90%, 95%, 98%, or 100% of a Coleopteran insect population are killed by an RNAi molecule that targets IAP. In some embodiments, percent mortality of an RNAi molecule is compared to a control (e.g., a control molecule or untreated conditions). In some embodiments, percent mortality of an RNAi molecule is at least 30%, 40%, 50%, 60%, 70%, 80%, 90%, 100%, 120%, 150%, or 200% higher than a control (e.g., a control molecule or untreated conditions).

In some embodiments, the effectiveness of an RNAi molecule to control Coleopteran insects can be determined using the ability of the RNAi molecule to limit the leaf disc consumption of a Coleopteran insect or an insect population. Leaf disc consumption refers to the amount (e.g., percentage) of plant material (e.g., an eggplant leaf) that is consumed or eaten by an insect or population of insects. In some embodiments, an RNAi molecule causes at least a 10%, 20%, 30%, 40%, 50%, 60%, 70%, 80%, 90%, 95%, 98%, or 100% decrease in the leaf disc consumption by an insect or population of insects. In some embodiments, the ability of an RNAi molecule to decrease leaf disc consumption is compared relative to a control (e.g., a control molecule or untreated conditions). In some embodiments, leaf disc consumption is measured over time (e.g., over the course of a multi-day exposure of insects to an RNAi molecule). In some embodiments, leaf disc consumption is measured after 3, 4, 5, 6, 7, 8, 9, 10, or more days of exposure.

In some embodiments, the effectiveness of an RNAi molecule to control Coleopteran insects can be determined using the ability of the RNAi molecule to decrease percent plant defoliation by a Coleopteran insect or an insect population. Percent plant defoliation refers to the percentage of plant material (e.g., an eggplant leaf) that is destroyed (e.g., consumed) by an insect or population of insects. In some embodiments, an RNAi molecule causes at least a 10%, 20%, 30%, 40%, 50%, 60%, 70%, 80%, 90%, 95%, 98%, or 100% decrease in the percent plant defoliation by an insect or population of insects. In some embodiments, an RNAi molecule causes percent plant defoliation to decrease below 40%, 30, 25%, 20%, 15%, 10%, 5%, 3%, or 1%. In some embodiments, percent plant defoliation remains below 40%, 30, 25%, 20%, 15%, 10%, 5%, 3%, or 1% for at least 5, 6, 7, 8, 9, 10, 15, or 20 days following exposure of insects to an RNAi molecule. In some embodiments, the ability of an RNAi molecule to decrease percent plant defoliation is compared relative to a control (e.g., a control molecule or untreated conditions). In some embodiments, percent plant defoliation is measured over time (e.g., over the course of a multi-day exposure of insects to an RNAi molecule). In some embodiments, percent plant defoliation is measured after 3, 4, 5, 6, 7, 8, 9, 10, or more days of exposure.

In some embodiments, an RNAi molecule targeting IAP may be formulated in a solution (e.g., that is applied to a surface of the Coleopteran insect and/or diet (e.g., food and/or water ingested), a plant or ground (e.g., soil, dirt, grass, etc.)). In some embodiments, the effective amount of the RNAi molecule targeting IAP in the solution is expressed as nanograms (ng) or micrograms (μg) of RNAi molecule targeting IAP per milliliter (ml) of the solution, i.e., ng/ml. Thus, in some embodiments, a solution comprises an RNAi molecule targeting IAP at a concentration of 10 ng/ml to 100 μg/ml. In some embodiments, a solution comprises an RNAi molecule targeting IAP at a concentration of 10 ng/ml to 100 μg/ml, 100 ng/ml to 100 μg/ml, 250 ng/ml to 100 μg/ml, 750 ng/ml to 100 μg/ml, 1000 ng/ml to 100 μg/ml, 10 μg/ml to 100 μg/ml, 25 μg/ml to 100 μg/ml, 50 μg/ml to 100 μg/ml, or 75 μg/ml to 100 μg/ml. In some embodiments, a solution comprises an RNAi molecule targeting IAP at a concentration of 10 ng/ml to 100 μg/ml, 10 ng/ml to 75 μg/ml, 10 ng/ml to 50 μg/ml, 10 ng/ml to 25 μg/ml, 10 ng/ml to 10 μg/ml, 10 ng/ml to 1000 ng/ml, 10 ng/ml to 1000 ng/ml, 10 ng/ml to 750 ng/ml, 10 ng/ml to 500 ng/ml, 10 ng/ml to 250 ng/ml, 10 ng/ml to 100 ng/ml, 10 ng/ml to 75 ng/ml, 10 ng/ml to 50 ng/ml, or 10 ng/ml to 25 ng/ml.

A solution, in some embodiments, comprises an RNAi molecule targeting IAP and at least one additional additive (e.g., a pesticide, surfactant or other non-pesticidal agent). In some embodiments, such a mixture comprises an RNAi molecule targeting IAP at a concentration of 0.0001 μg/ml to 10 μg/ml (e.g., that is applied to a surface of a plant and/or ground (e.g., soil, dirt, grass, etc.)). In some embodiments, such a mixture comprises an RNAi molecule targeting IAP at a concentration of 0.001 μg/ml to 10 μg/ml, 0.01 μg/ml to 10 μg/ml, 0.1 μg/ml to 10 μg/ml, 1 μg/ml to 10 μg/ml, 2 μg/ml to 10 μg/ml, 3 μg/ml to 10 μg/ml, 4 μg/ml to 10 μg/ml, 5 μg/ml to 10 μg/ml, 6 μg/ml to 10 μg/ml, 7 μg/ml to 10 μg/ml, 8 μg/ml to 10 μg/ml, or 9 μg/ml to 10 μg/ml. In some embodiments, such a mixture comprises an RNAi molecule targeting IAP at a concentration of 0.0001 μg/ml to 9 μg/ml, 0.0001 μg/ml to 8 μg/ml, 0.0001 μg/ml to 7 μg/ml, 0.0001 μg/ml to 6 μg/ml, 0.0001 μg/ml to 5 μg/ml, 0.0001 μg/ml to 4 μg/ml, 0.0001 μg/ml to 3 μg/ml, 0.0001 μg/ml to 2 μg/ml, 0.0001 μg/ml to 1 μg/ml, 0.0001 μg/ml to 0.1 μg/ml, 0.0001 μg/ml to 0.01 μg/ml, or 0.0001 μg/ml to 0.001 μg/ml.

In some embodiments, an RNAi molecule targeting IAP is provided in a diet of an insect. Thus, in some embodiments, an effective amount of an RNAi molecule targeting IAP is expressed as micrograms (μg) of RNAi molecule targeting IAP per milliliter (ml) of the diet of the insect, i.e., μg/ml. In some embodiments, the diet of an insect comprises an RNAi molecule targeting IAP at a concentration of 0.001 μg/ml to 10 μg/ml. In some embodiments, the diet of an insect comprises an RNAi molecule targeting IAP at a concentration of 0.001 μg/ml to 9 μg/ml, 0.001 μg/ml to 8 μg/ml, 0.001 μg/ml to 7 μg/ml, 0.001 μg/ml to 6 μg/ml, 0.001 μg/ml to 5 μg/ml, 0.001 μg/ml to 4 μg/ml, 0.001 μg/ml to 3 μg/ml, 0.001 μg/ml to 2 μg/ml, 0.001 μg/ml to 1 μg/ml, 0.001 μg/ml to 0.1 μg/ml, or 0.001 μg/ml to 0.01 μg/ml. In some embodiments, the diet of an insect comprises an RNAi molecule targeting IAP at a concentration of 0.01 μg/ml to 10 μg/ml, 0.1 μg/ml to 10 μg/ml, 1 μg/ml to 10 μg/ml, 2 μg/ml to 10 μg/ml, 3 μg/ml to 10 μg/ml, 4 μg/ml to 10 μg/ml, 5 μg/ml to 10 μg/ml, 6 μg/ml to 10 μg/ml, 7 μg/ml to 10 μg/ml, 8 μg/ml to 10 μg/ml, or 9 μg/ml to 10 μg/ml.

The step of delivering to any portion of a plant (e.g., roots, tubers, stem, branches, leaves, flower, etc), ground (e.g., soil, dirt, grass, etc.), insect and/or diet of the insect with an RNAi molecule targeting IAP may include a single application (single contact) or multiple applications (multiple contacts) of the RNAi molecule targeting IAP to the plant, ground (e.g., soil, dirt, grass, etc.), insect and/or diet of the insect. Delivery to a portion of a plant, insect and/or diet of the insect may be in the form of a spray (e.g., pressurized/aerosolized spray, pump) solid, (e.g. powder, pellet, bait), or liquid (e.g., homogeneous mixtures such as solutions and non-homogeneous mixtures such as suspensions (water and oil based), colloids, micelles, and emulsions). The period of time of contact may vary. In some embodiments, delivering comprises an exposure of an RNAi molecule targeting IAP with a portion of a plant and/or Coleopteran insect for a suitable period sufficient for reduction of growth, reproduction (e.g., fertility and/or fecundity), and/or feeding of the Coleopteran insect and/or death of the Coleopteran insect, if any.

In some embodiments, delivery of an RNAi molecule targeting IAP with a plant and/or Coleopteran insect is followed by ingestion and/or absorption of the RNAi molecule targeting IAP by the plant and/or Coleopteran insect. In some embodiments, ingestion of the RNAi molecule targeting IAP by the Coleopteran insect alters a biological function of the Coleopteran insect, thereby controlling infestation by the Coleopteran insect. Examples of altered biological function of the Coleopteran insect include, but are not limited to, reduced growth, reduced reproduction (e.g., fertility and/or fecundity), reduced feeding, decreased movement, decreased development, decreased cellular repair, and/or increased mortality.

In some embodiments, delivering comprises applying an RNAi molecule targeting IAP to a portion of the surface of a plant and/or a surface contacted by a Coleopteran insect (e.g., ground (e.g., soil, dirt, grass, etc.)). In some embodiments, applying an RNAi molecule targeting IAP to a portion of a surface comprises spraying, coating, and/or dusting the surface or portion thereof. In some embodiments, applying an RNAi molecule targeting IAP RNA to a portion of a surface comprises ground drenching or applying the RNAi molecule as a granulated or powdered formulation to the soil adjacent to the roots of the plant.

A RNAi molecule targeting IAP may be applied to any portion of a plant (e.g., roots, tubers, stem, branches, leaves, flower, etc). In some embodiments, the RNAi molecule targeting IAP is contacted with an above-ground portion of a plant (e.g., a leaf) and/or with a below-ground portion of a plant (e.g., a root), which may include at least one in furrow formulation selected from the group consisting of a powder, granule, pellet, capsule, soluble liquid concentrate, spray(after dilution or concentrate), fog, in furrow, seed treatment, insect diet, bait, drench, drip irrigation, or any other forms suited for applying to a furrow. Portions of a plant that may be contacted with the RNAi molecule targeting IAP described herein include, but are not limited to, leaf, stem, flower, fruit, shoot, root, seed, tuber, anther, stamen, or pollen. In some embodiments, RNAi is delivered mechanically, through high pressure spray or sand blasting.

In some embodiments, delivering comprises providing an RNAi molecule targeting IAP for dietary uptake by the Coleopteran insect. In some embodiments, contacting comprises providing an RNAi molecule targeting IAP that can be ingested or otherwise absorbed internally by the Coleopteran insect. In some embodiments, the RNAi molecule targeting IAP is provided in a diet for dietary uptake by the Coleopteran insect. In some embodiments, the RNAi molecule targeting IAP is provided in/on a plant or plant part, or topically applied to a plant or plant part (e.g., soaking, coating, dusting). In some embodiments, the RNAi molecule targeting IAP is expressed in a plant or plant part.

In some embodiments, delivering an RNAi molecule targeting IAP to a Coleopteran insect inhibits expression of (reduces or inhibits expression of) an endogenous complementary nucleotide sequence (e.g., RNA sequence) in the Coleopteran insect. In some embodiments, the endogenous complementary nucleotide sequence is an endogenous IAP sequence.

Consequences of inhibition can be confirmed by any appropriate assay to evaluate one or more properties of an insect, or by biochemical techniques that evaluate molecules indicative of IAP expression (e.g., RNA, protein). In some embodiments, the extent to which an RNAi molecule targeting IAP provided herein reduces levels of expression of IAP is evaluated by comparing expression levels (e.g., mRNA or protein levels of IAP to an appropriate control (e.g., a level of IAP expression in a cell or population of cells to which an RNAi molecule targeting IAP has not been delivered or to which a negative control has been delivered). In some embodiments, an appropriate control level of IAP expression may be a predetermined level or value, such that a control level need not be measured every time. The predetermined level or value can take a variety of forms. In some embodiments, a predetermined level or value can be single cut-off value, such as a median or mean.

In some embodiments, delivering an RNAi molecule targeting IAP as described herein results in a reduction in the level of IAP expression in a cell of an insect. In some embodiments, the reduction in levels of IAP expression may be a reduction by at least 10%, at least 20%, at least 30%, at least 40%, at least 50%, at least 60%, at least 70%, at least 80%, at least 90%, at least 95%, at least 98%, at least 99%, or 100% relative to a control level. In some embodiments, the control level is a level of IAP expression in a similar insect cell (or average level among a population of cells) not contacted with the RNAi molecule. In some embodiments, the control level is a level of IAP expression in a similar insect cell (or average level among a population of cells) contacted with an RNAi molecule targeting a gene not expressed by the insect cell, e.g., green fluorescent protein (GFP).

In some embodiments, the effect of delivering to a cell or insect an RNAi molecule targeting IAP is assessed after a finite period of time. For example, levels of IAP may be determined in a cell or insect at least 4 hours, 8 hours, 12 hours, 18 hours, 24 hours; or at least one, two, three, four, five, six, seven, or fourteen days after delivering to the cell or insect the RNAi molecule targeting IAP.

In some embodiments, delivery of an RNAi molecule targeting IAP as described herein results in a reduction in the level of growth, reproduction (e.g., fertility and/or fecundity), and/or feeding of an insect. In some embodiments, the reduction in levels of growth, reproduction (e.g., fertility and/or fecundity), and/or feeding may be a reduction by at least 10%, at least 20%, at least 30%, at least 40%, at least 50%, at least 60%, at least 70%, at least 80%, at least 90%, at least 95%, at least 98%, at least 99%, or 100% relative to a control level. In some embodiments, the control level is a level of growth, reproduction (e.g., fertility and/or fecundity), and/or feeding of a similar insect not contacted with the RNAi molecule. In some embodiments, the control level is a level of growth, reproduction (e.g., fertility and/or fecundity), and/or feeding of a similar insect contacted with an RNAi molecule targeting a gene not expressed by the insect cell, e.g., green fluorescent protein (GFP).

In some embodiments, delivery of an RNAi molecule targeting IAP as described herein results in an increase in mortality among a population of insects. In some embodiments, the increase in level of mortality may be an increase by at least 10%, at least 20%, at least 30%, at least 40%, at least 50%, at least 60%, at least 70%, at least 80%, at least 90%, at least 95%, at least 98%, at least 99%, or 100% relative to a control. In some embodiments, the control is mortality among a population of insects not contacted with the RNAi molecule. In some embodiments, the control is among a population of insects contacted with an RNAi molecule targeting a gene not expressed by the insect cell, e.g., green fluorescent protein (GFP).

Aspects of the present disclosure provide plants that expresses an RNAi molecule targeting IAP as described herein. In some embodiments, DNA encoding an RNAi molecule targeting IAP provided herein is provided to a plant (seed or cells of a plant) such that the plant expresses the RNAi molecule targeting IAP. In some embodiments, DNA encoding an RNAi molecule targeting IAP is expressed in a plant by transgenic expression, e.g., by stably integrating DNA encoding an RNAi molecule targeting IAP into a genome of a plant such that the plant expresses the RNAi molecule targeting IAP.

Methods of Producing RNAi Molecules Targeting IAP

RNAi molecules targeting IAP as provided herein may be produced by any suitable method known in the art. Examples of methods for producing an RNAi molecule targeting IAP include, but are not limited to, in vitro transcription (IVT), chemical synthesis, expression in an organism (e.g., a plant), or expression in cell culture (e.g., a plant cell culture), and microbial fermentation.

RNAi molecules targeting IAP may be produced, in some embodiments, according to cell-free production methods described in International Application Publication WO 2017/176963 A1, published Oct. 12, 2017, entitled "Cell-Free Production of Ribonucleic Acid"; U.S. Provisional Application U.S. Ser. No. 62/571,071 filed Oct. 11, 2017, entitled "Methods and Compositions for Nucleoside Triphosphate and Ribonucleic Acid Production"; and International Application Publication WO 2019/075167 A1, published Apr. 18, 2019, entitled "Methods and Compositions for Nucleoside Triphosphate and Ribonucleic Acid Production"; each of which is incorporated herein by reference.

Any suitable DNA encoding RNAi molecules targeting IAP described herein may be used in the methods described herein. A DNA may be a single-stranded DNA (ssDNA) or a double-stranded DNA (dsDNA). In some embodiments, a DNA comprises one or more DNA expression cassette(s) that when transcribed produces a single-stranded RNA (ssRNA) molecule (e.g., that remains single stranded or folds into an RNA hairpin) or complementary ssRNA molecules that anneal to produce the double-stranded RNA (dsRNA) molecule.

In some embodiments, a DNA comprises a promoter (e.g., an inducible promoter) operably linked to a nucleotide sequence encoding RNA that is complementary to a segment of IAP, and optionally a terminator. In other embodiments, a DNA comprises a first promoter (e.g., an inducible promoter) operably linked to a nucleotide sequence encoding RNA that is complementary to a segment of IAP, and optionally a terminator, and a second promoter (e.g., an inducible promoter) operably linked to a nucleotide sequence encoding a second RNA that is complementary to the first RNA, and optionally a terminator. In yet other embodiments, a DNA comprises a promoter (e.g., an inducible promoter) operably linked to a nucleotide sequence encoding a first region of an RNA, followed by one or more nucleotides of a loop region, followed by a second region of the RNA, and optionally followed by a terminator, wherein the first region of the RNA is complementary to a segment of IAP and the second region is complementary to the first region. In still other embodiments, a DNA comprises a first strand comprising a first promoter (e.g., an inducible promoter) operably linked to a nucleotide sequence encoding a first RNA that is complementary to a segment of IAP, and optionally a terminator, and a second strand comprising a second promoter (e.g., an inducible promoter) operably linked to a nucleotide sequence encoding a second RNA that is complementary to the first RNA, and optionally a terminator wherein the first and second promoters are operably linked to the nucleotide sequence encoding a desired IAP-targeting RNA and wherein the bidirectional transcription of the nucleotide sequence encoding the desired IAP-targeting RNA results in complementary RNA molecules which anneal to form the dsRNA molecule.

A DNA is typically provided on a vector, such as a plasmid, although other template formats may be used (e.g., linear DNA generated by polymerase chain reaction (PCR), chemical synthesis, or other means known in the art). In some embodiments, more than one DNA is used in a reaction mixture. In some embodiments, 2, 3, 4, 5, or more different DNAs are used in a reaction mixture.

A promoter or terminator may be a naturally-occurring sequence or an engineered (e.g., synthetic) sequence. In some embodiments, an engineered sequence is modified to enhance transcriptional activity. In some embodiments, the promoter is a naturally-occurring sequence. In other embodiments, the promoter is an engineered sequence. In some embodiments, the terminator is a naturally-occurring sequence. In other embodiments, the terminator is an engineered sequence.

EXAMPLES

In order that the invention described herein may be more fully understood, the following examples are set forth. The Examples described in this Application are offered to illustrate the methods, compositions, and systems provided herein and are not to be construed in any way as limiting their scope.

The double-stranded RNA (dsRNA) molecules used in the Examples below are as follows, the sequences of which are presented in Table 8.

GS3: one RNA strand consisting of the sequence of SEQ ID NO: 21 bound to another RNA strand consisting of the sequence of SEQ ID NO: 39. GS3 targets mRNA encoded by nucleotides 750-1181 of the DNA sequence of SEQ ID NO: 1.

GS4: one RNA strand consisting of the sequence of SEQ ID NO: 22 bound to another RNA strand consisting of the sequence of SEQ ID NO: 40. GS4 targets mRNA encoded by gfp.

GS167: one RNA strand consisting of the sequence of SEQ ID NO: 23 bound to another RNA strand consisting of the sequence of SEQ ID NO: 41. GS167 targets mRNA encoded by nucleotides 1-521 of the DNA sequence of SEQ ID NO: 1.

GS168: one RNA strand consisting of the sequence of SEQ ID NO: 24 bound to another RNA strand consisting of the sequence of SEQ ID NO: 42. GS168 targets mRNA encoded by nucleotides 522-1044 of the DNA sequence of SEQ ID NO: 1.

GS169: one RNA strand consisting of the sequence of SEQ ID NO: 25 bound to another RNA strand consisting of the sequence of SEQ ID NO: 43. GS169 targets mRNA encoded by nucleotides 1045-1564 of the DNA sequence of SEQ ID NO: 1.

GS170: one RNA strand consisting of the sequence of SEQ ID NO: 26 bound to another RNA strand consisting of the sequence of SEQ ID NO: 44. GS170 has 70% sequence identity to GS3, which targets mRNA encoded by nucleotides 750-1181 of the DNA sequence of SEQ ID NO: 1.

GS171: one RNA strand consisting of the sequence of SEQ ID NO: 27 bound to another RNA strand consisting of the sequence of SEQ ID NO: 45. GS171 has 75% sequence identity to GS3, which targets mRNA encoded by nucleotides 750-1181 of the DNA sequence of SEQ ID NO: 1.

GS172: one RNA strand consisting of the sequence of SEQ ID NO: 28 bound to another RNA strand consisting of the sequence of SEQ ID NO: 46. GS172 has 80% sequence identity to GS3, which targets mRNA encoded by nucleotides 750-1181 of the DNA sequence of SEQ ID NO: 1.

GS173: one RNA strand consisting of the sequence of SEQ ID NO: 29 bound to another RNA strand consisting of the sequence of SEQ ID NO: 47. GS173 has 85% sequence identity to GS3, which targets mRNA encoded by nucleotides 750-1181 of the DNA sequence of SEQ ID NO: 1.

GS174: one RNA strand consisting of the sequence of SEQ ID NO: 30 bound to another RNA strand consisting of the sequence of SEQ ID NO: 48. GS174 has 90% sequence identity to GS3, which targets mRNA encoded by nucleotides 750-1181 of the DNA sequence of SEQ ID NO: 1.

GS175: one RNA strand consisting of the sequence of SEQ ID NO: 31 bound to another RNA strand consisting of the sequence of SEQ ID NO: 49. GS175 has 95% sequence identity to GS3, which targets mRNA encoded by nucleotides 750-1181 of the DNA sequence of SEQ ID NO: 1.

GS176: one RNA strand consisting of the sequence of SEQ ID NO: 32 bound to another RNA strand consisting of the sequence of SEQ ID NO: 50. GS176 targets mRNA encoded by nucleotides 909-1108 of the DNA sequence of SEQ ID NO: 1.

GS177: one RNA strand consisting of the sequence of SEQ ID NO: 33 bound to another RNA strand consisting of the sequence of SEQ ID NO: 51. GS177 targets mRNA encoded by nucleotides 934-1083 of the DNA sequence of SEQ ID NO: 1.

GS178: one RNA strand consisting of the sequence of SEQ ID NO: 34 bound to another RNA strand consisting of the sequence of SEQ ID NO: 52. GS178 targets mRNA encoded by nucleotides 959-1058 of the DNA sequence of SEQ ID NO: 1.

GS179: one RNA strand consisting of the sequence of SEQ ID NO: 35 bound to another RNA strand consisting of the sequence of SEQ ID NO: 53. GS179 targets mRNA encoded by nucleotides 984-1033 of the DNA sequence of SEQ ID NO: 1.

GS180: one RNA strand consisting of the sequence of SEQ ID NO: 36 bound to another RNA strand consisting of the sequence of SEQ ID NO: 54. GS180 targets mRNA encoded by nucleotides 996-1020 of the DNA sequence of SEQ ID NO: 1.

Example 1: IAP RNAi Composition Kills Colorado Potato Beetles

Figure 1B:
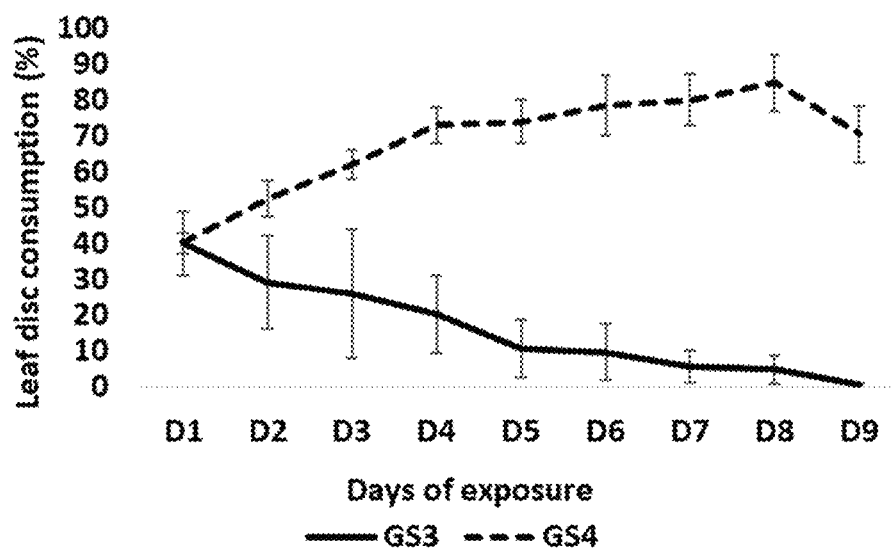

To evaluate the effect of the IAP RNAi polynucleotide (SEQ ID NOS: 21 and 39) on Colorado potato beetles (CPBs), a composition (e.g., comprising water) comprising a IAP RNAi polynucleotide (hereafter, "G53") was treated (at a concentration of 10 µg/cm$^2$) onto the leaves of potato plants. Up to 90% of CPBs died following a 9-day exposure to the GS3-covered potato plant leaves, compared with less than 10% of CPBs that die following exposure to the negative control (GS4) leaves (FIG. 1A). This increased mortality in response to exposure to GS3 also results in a decrease of potato leaf consumption to nearly 0% (FIG. 1B). Percent potato leaf consumption refers to the percentage of potato leaf discs (punched out of potato leaves) following treatment of the discs with the RNAi composition and subsequent exposure of the discs to Colorado potato beetle, for example.

Figure 2A:
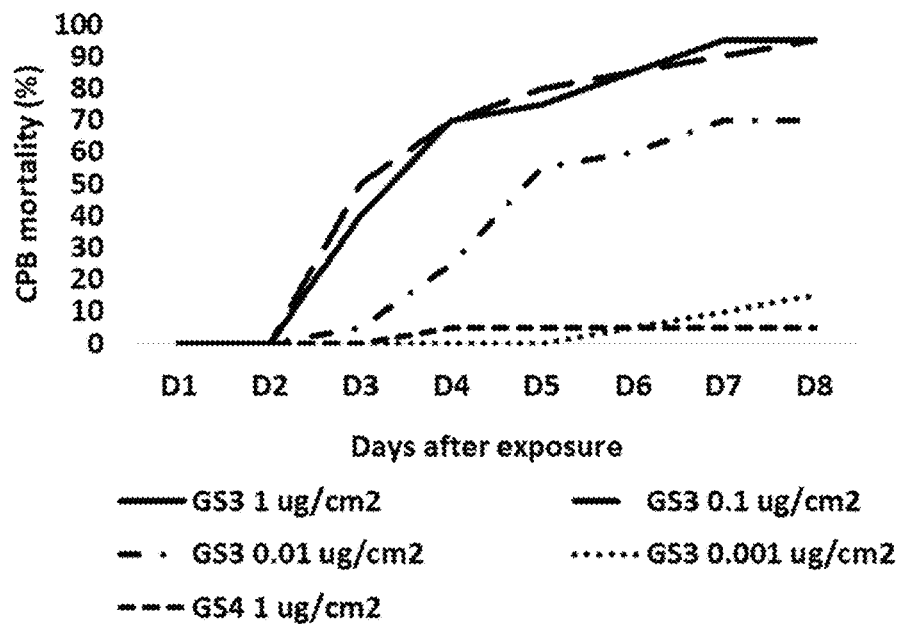
FIGS. 2A-2B include graphs showing the percent mortality of Colorado potato beetles (CPBs) (FIG. 2A) and percent leaf disc consumption by CPBs (FIG. 2B) following an eight-day dose-trial time course in CPBs exposed for the first three (3) days to either an IAP RNAi composition of the present disclosure (GS3 at 1.0 μg/cm², 0.1 μg/cm², 0.01 μg/cm², or 0.001 μg/cm²) or a control RNAi composition (GS4 at 1.0 μg/cm²).
Figure 2B:
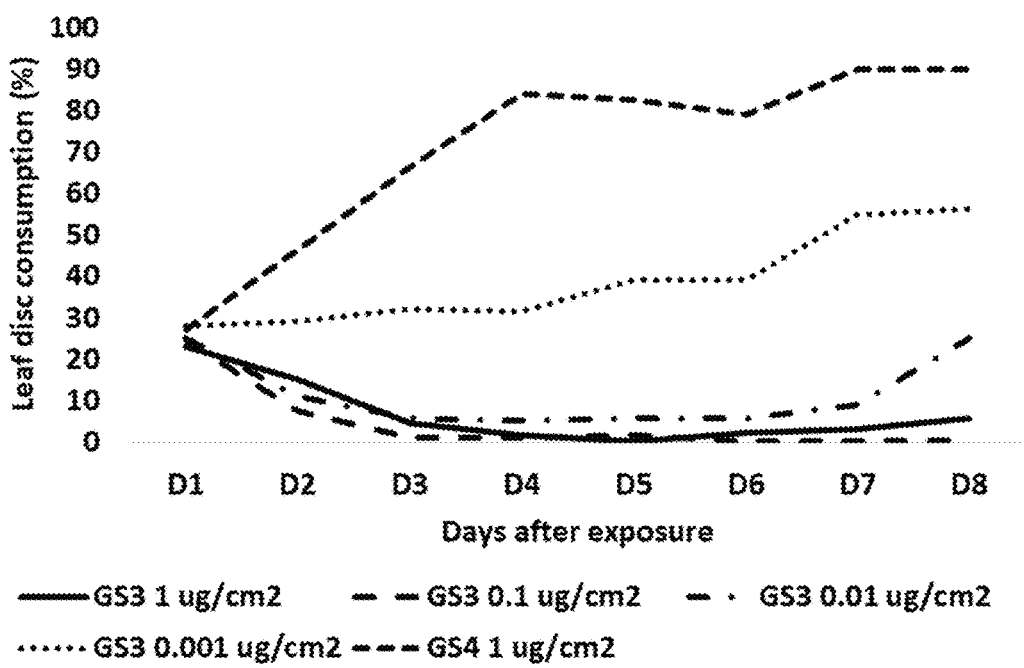

A dose-titration of the GS3 composition was also performed to determine if a lower concentration of the IAP RNAi polynucleotide is equally effective in controlling CPBs. Up to 90% of CPBs died following a three-day exposure to GS3 at 1.0 µg/cm$^2$ and 0.1 µg/cm$^2$, about 70% of CPBs died following a three-day exposure to GS3 at 0.01 µg/cm$^2$, and about 15% of CPBs died following a three-day exposure to GS3 at 0.001 µg/cm$^2$ compared to a control (GS4) composition at 1.0 µg/cm$^2$ (FIG. 2A). Potato leaf consumption also decreased to nearly 0% when CPBs were exposure to GS3 at 1.0 µg/cm$^2$ and 0.1 µg/cm$^2$, while CPBs exposed to GS3 at 0.01 µg/cm$^2$ only consumed about 20% of potato leaves, and CPBs exposed to GS3 at 0.001 µg/cm$^2$ consumed about 60% of potato leaves (FIG. 2B).

Exposure of CPBs to the IAP RNAi polynucleotide administered to potato leaves at a concentration of as low as 0.1 µg/cm$^2$ results in a 90% mortality and a 95% decreased potato leaf consumption compared to CPBs exposed to a control.

Figure 3A:
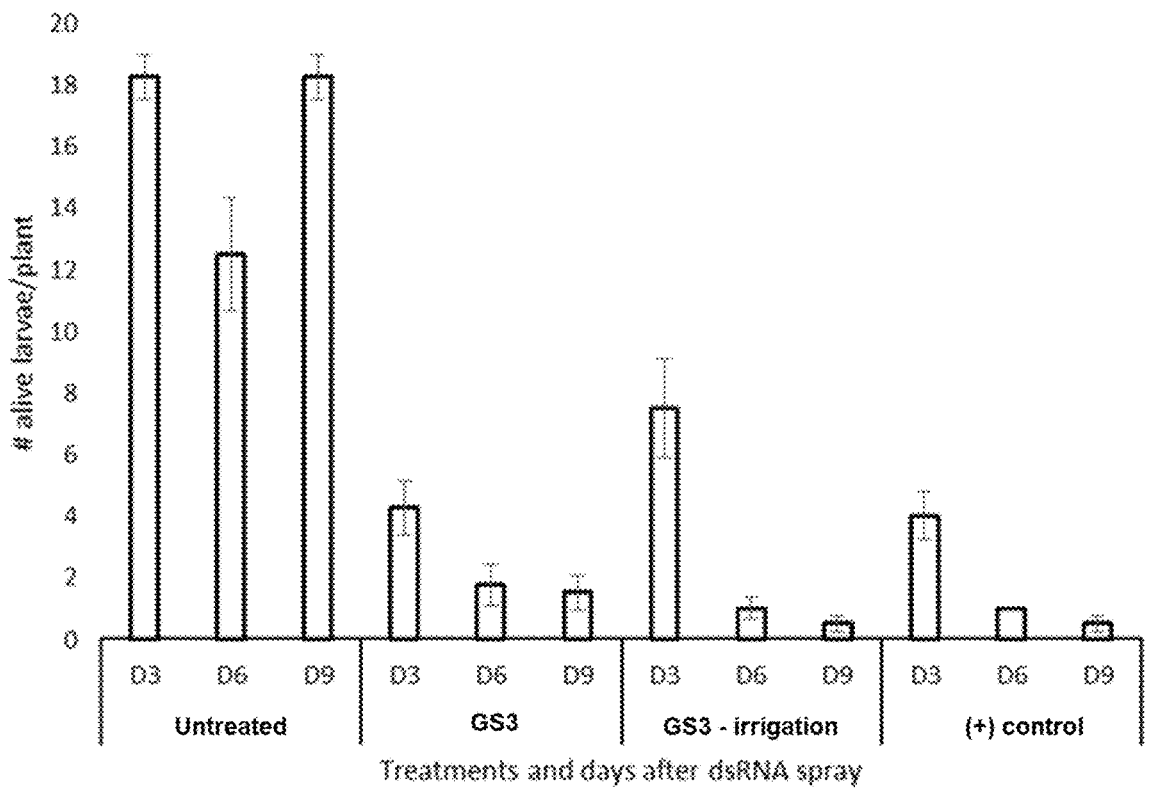
FIGS. 3A-3B include graphs showing the number of live CPB larvae per plant (FIG. 3A) and percent plant defoliation (FIG. 3B) following leaf treatment with either an IAP RNAi composition of the present disclosure (GS3), an IAP RNAi composition followed by irrigation (approximately 500 ml of water per plant, simulating ½ inch of rain), a control composition (+control), or no treatment (untreated).
Figure 3B:
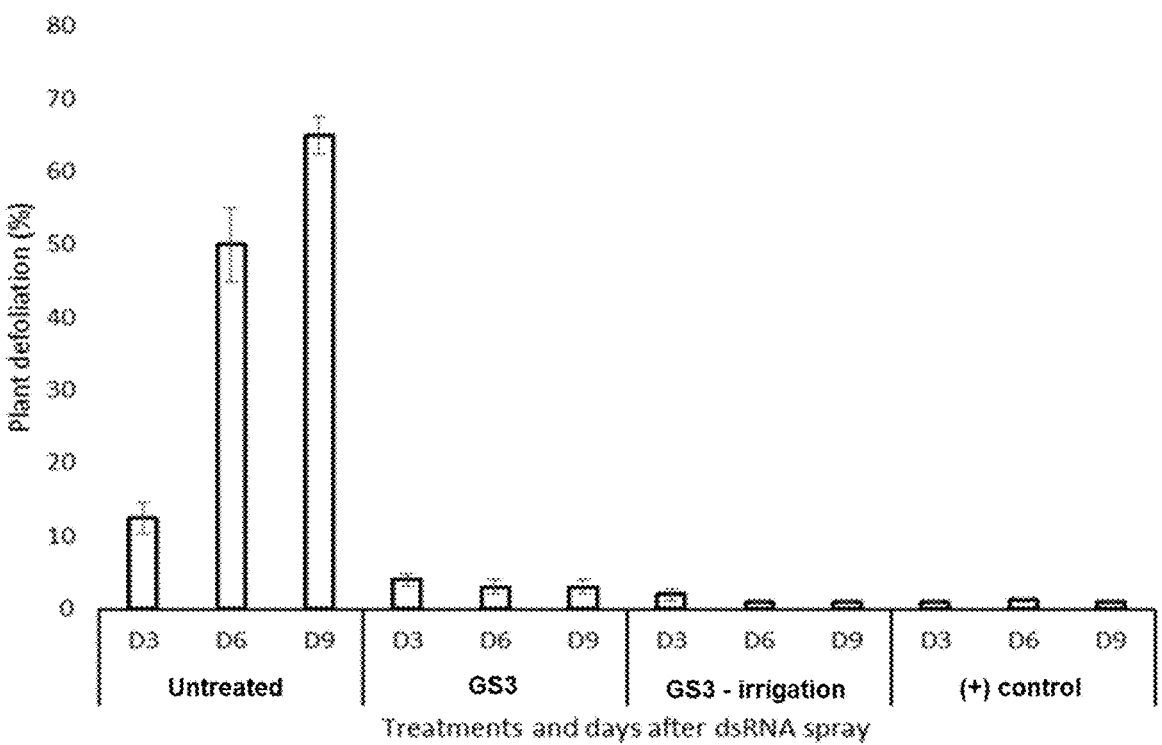
Figure 4:
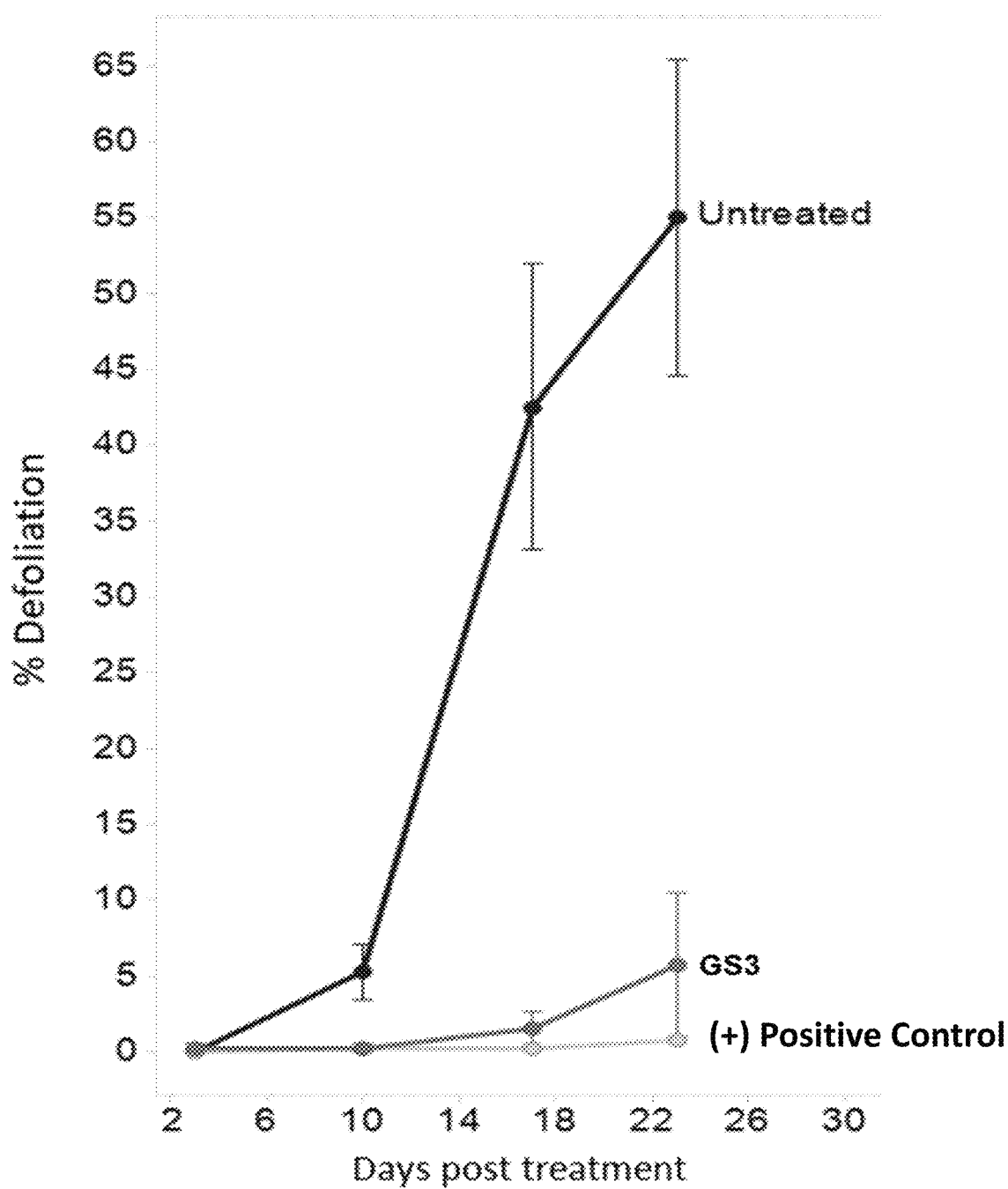
FIG. 4 includes a graph showing the percent plant defoliation following leaf treatment in field trials with an IAP RNAi composition of the present disclosure (GS3), a control composition (+control, e.g., CORAGEN®), and no treatment (untreated).

Example 2: Application of IAP RNAi Composition to Plants Controls Colorado Potato Beetles The composition comprising IAP RNAi polynucleotide (GS3) of Example 1 was tested for its effectiveness in controlling the numbers of Colorado potato beetles (CPBs) on a potato plant. Briefly, the GS3 composition (e.g., 0.06 g/L), a composition comprising CORAGEN® (+control; an agent known to kill CPBs), or no treatment (-control) was applied to the leaves of potato plants. The effect of irrigation (approximately 500 ml of water per plant, simulating ½ inch of rain), on GS3 composition efficacy was also tested. The number of CPB larvae per plant was decreased by about 90% in potato plants treated with GS3, regardless of irrigation, relative to untreated potato plants (FIG. 3A). The percent of potato plant defoliation was also decreased by about 90% when the plants were treated with GS3, regardless of irrigation, relative to untreated potato plants (FIG. 3B).

Exposure of CPBs to the IAP RNAi polynucleotide in the GS3 composition administered to potato plants decreased the numbers of live larvae per plant and plant defoliation by about 90% compared to CPBs exposed to potato plants that were untreated.

Example 3: IAP RNAi Compositions Spanning the Length of the IAP Gene are Effective at Controlling Colorado Potato Beetle (CPB) Infestation Four dsRNA molecules that collectively bind to the entire length of messenger RNA (mRNA) (SEQ ID NO: 19) encoded by a Coleopteran IAP gene (SEQ ID NO: 1) were evaluated for their effectiveness to control Colorado potato beetle (CPB) infestation. The dsRNA molecules used in this Example were: GS3, GS167, GS168, GS169, and the negative control molecule (GS4).

For each dsRNA, four leaves (~20 days old) were cut from an eggplant plant, coated with 0.5 of dsRNA, and dried for about 30 min. Each of the four leaves was placed into four different Petri dishes (100 mm×15 mm) on a moisture filter paper. For each petri dish, five 'second instar' CPB larvae were placed on top of each leaf and the dishes kept at room temperature. On Day 3 (after 72 hours) and Day 6 (after 144 hours), new dsRNA-treated leaves were placed into the Petri dishes. The total number of CPB insects was counted in each experiment on Days 3, 6, 7, 8, and 9. For purposes of determining mortality caused by each dsRNA, the initial count of living CPB insects was established on Day 2. Any CPB insects that were already dead on Day 2 were assumed to be dead because of handling conditions or initial insect health conditions. Each dsRNA experiment was duplicated using different batches of insects on different weeks, each comprising four different leaf Petri dishes).

Figure 5:
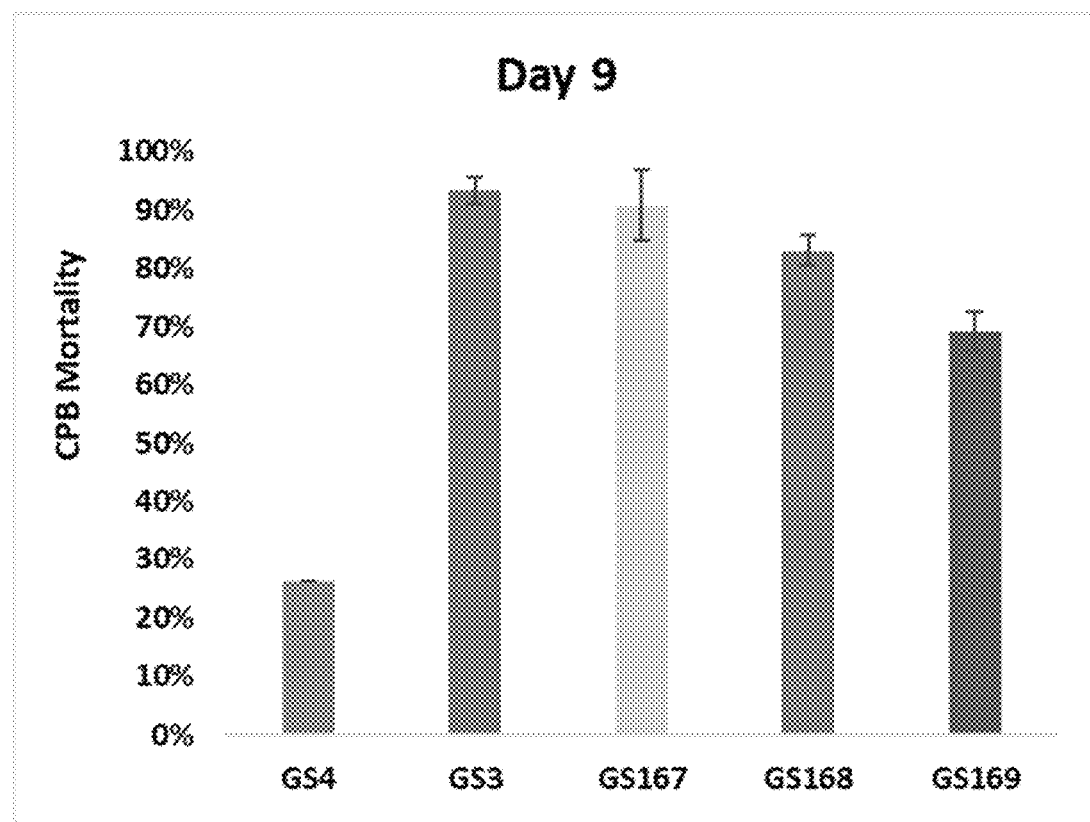
FIG. 5 includes a graph showing the percent mortality of Colorado potato beetles (CPBs) nine days after oral exposure to an RNAi composition that includes a double-stranded RNA (dsRNA) that targets an IAP mRNA encoded by a 5' terminal region of IAP DNA (GS167), an RNAi composition that includes a dsRNA that targets an IAP mRNA encoded by a central region of IAP DNA (GS168), an RNAi composition that includes a dsRNA that targets an IAP mRNA encoded by a 3' terminal region of IAP DNA (GS169), or a negative control RNAi composition (GS4) (n=2).
Figure 6A:
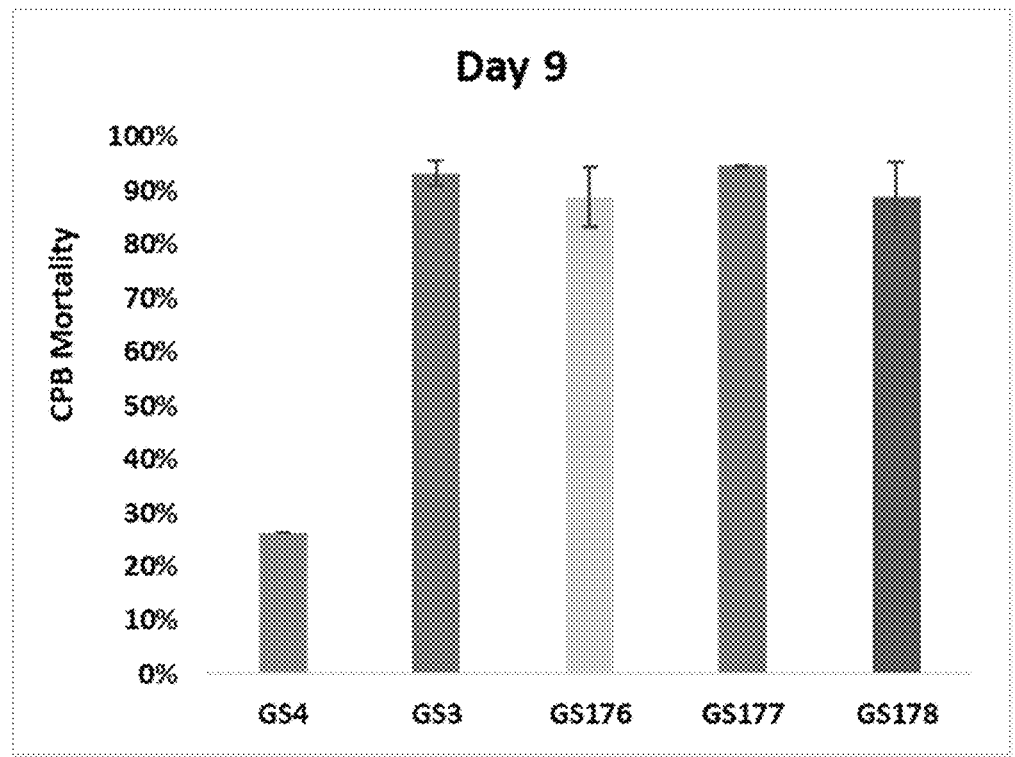
FIGS. 6A-6B include graphs showing the percent mortality of CPBs nine days after oral exposure to an RNAi composition that includes a dsRNA that targets IAP mRNA. The dsRNA varied in size, with GS3 having a length of 432-nucleotides, GS176 having a length of 200-nucleotides, GS177 having a length of 150-nucleotides, G178 having a length of 100-nucleotides (FIG. 6A), GS179 having a length of 74 nucleotides, with 50 complementary nucleotides, and GS193 having a length of 49 nucleotides with 25 complementary nucleotides (FIG. 6B). A negative control RNAi composition (GS4) was further evaluated.
Figure 6B:
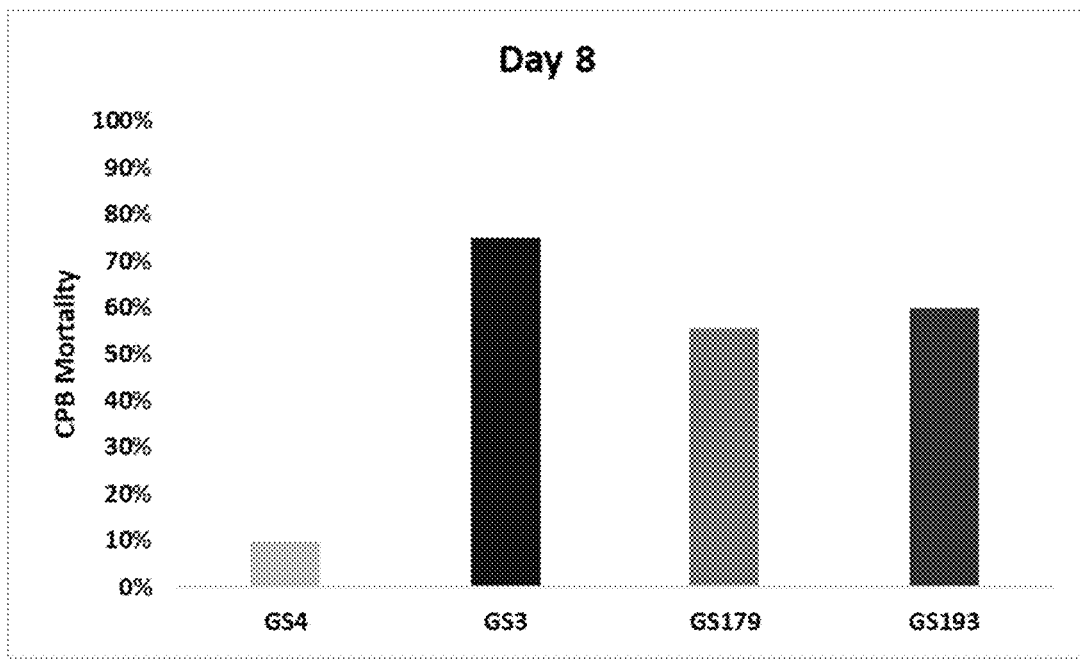
Figure 7:
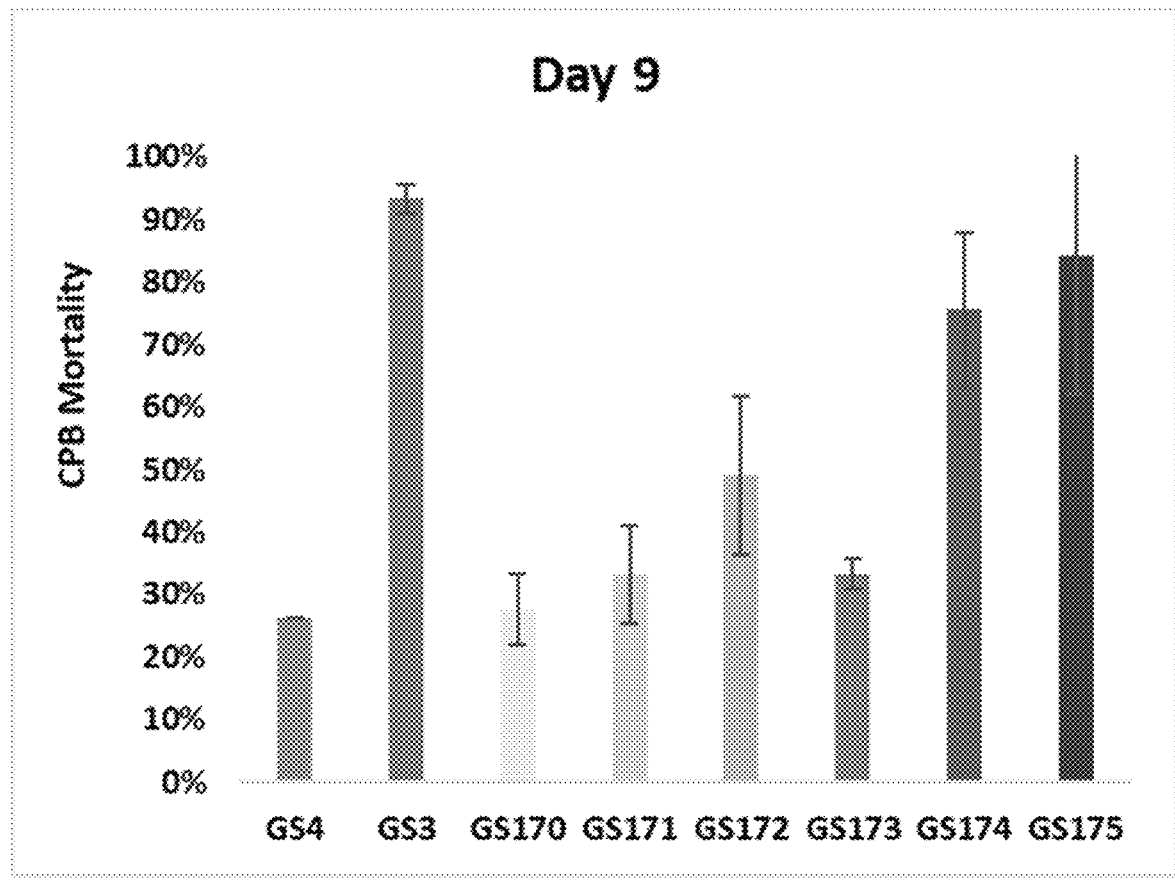
FIG. 7 includes a graph showing the percent mortality of CPBs nine days after oral exposure to an RNAi composition that includes a dsRNA that is 70% (GS170), 75% (GS171), 80% (GS172), 85% (GS173), 90% (GS174), or 95% (GS175) complementary to a IAP mRNA across a region having a length of 432-nucleotides (GS3). A negative control RNAi composition (GS4) was further evaluated.
Figure 8:
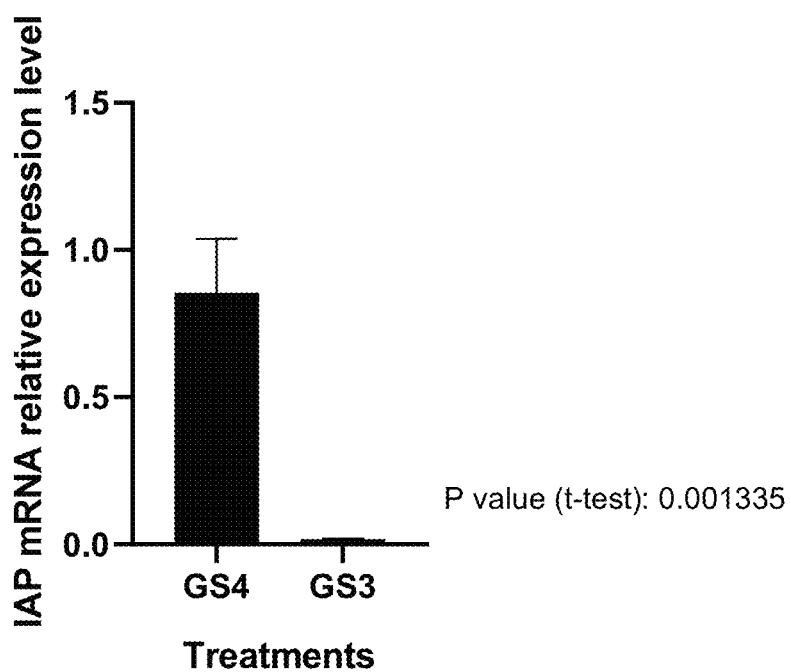
FIG. 8 includes a graph showing the IAP mRNA relative expression level of first instar CPB larvae fed on GS3 and GS4 at 0.1 μg/cm² for three days and collected after three days. The relative expression was normalized using the endogenous control RP4 gene and calculated using $2^{-ddCt}$ method.
Figure 9A:
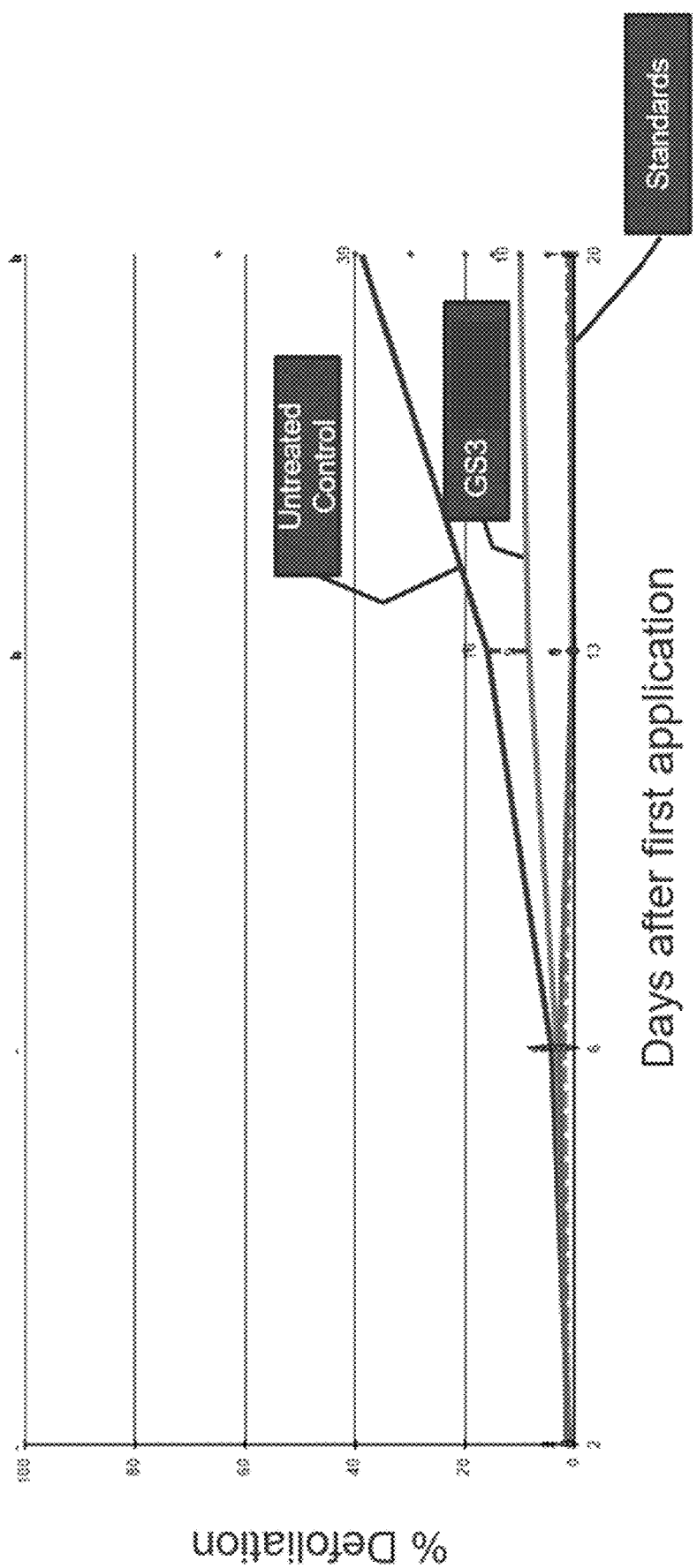
FIGS. 9A-9C include graphs showing the percent plant defoliation following leaf treatment in field trials with an IAP RNAi composition of the present disclosure (GS3), control positive compositions (standards, e.g., CORAGEN®, ENTRUST®, NOVODOR™), and no treatment (untreated control) over a twenty-one (21) day period.
Figure 9B:
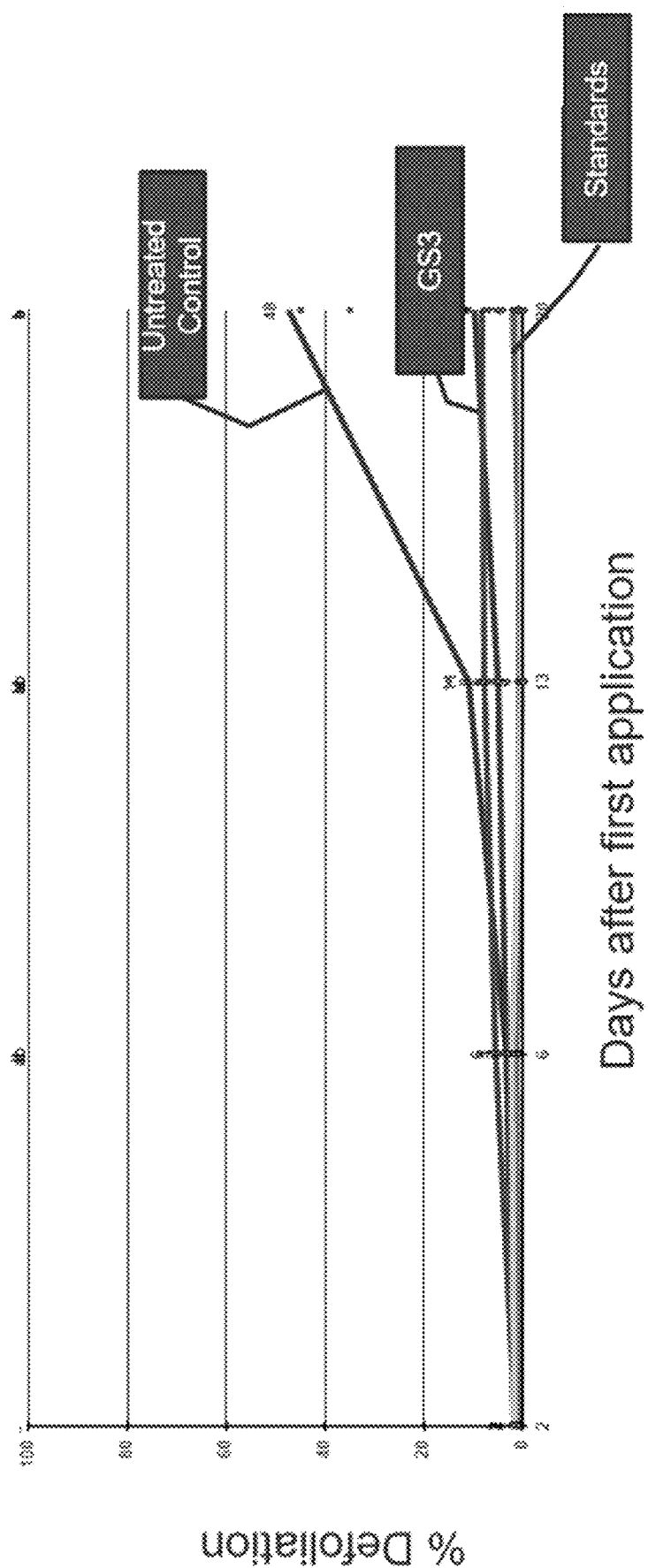
Figure 9C:
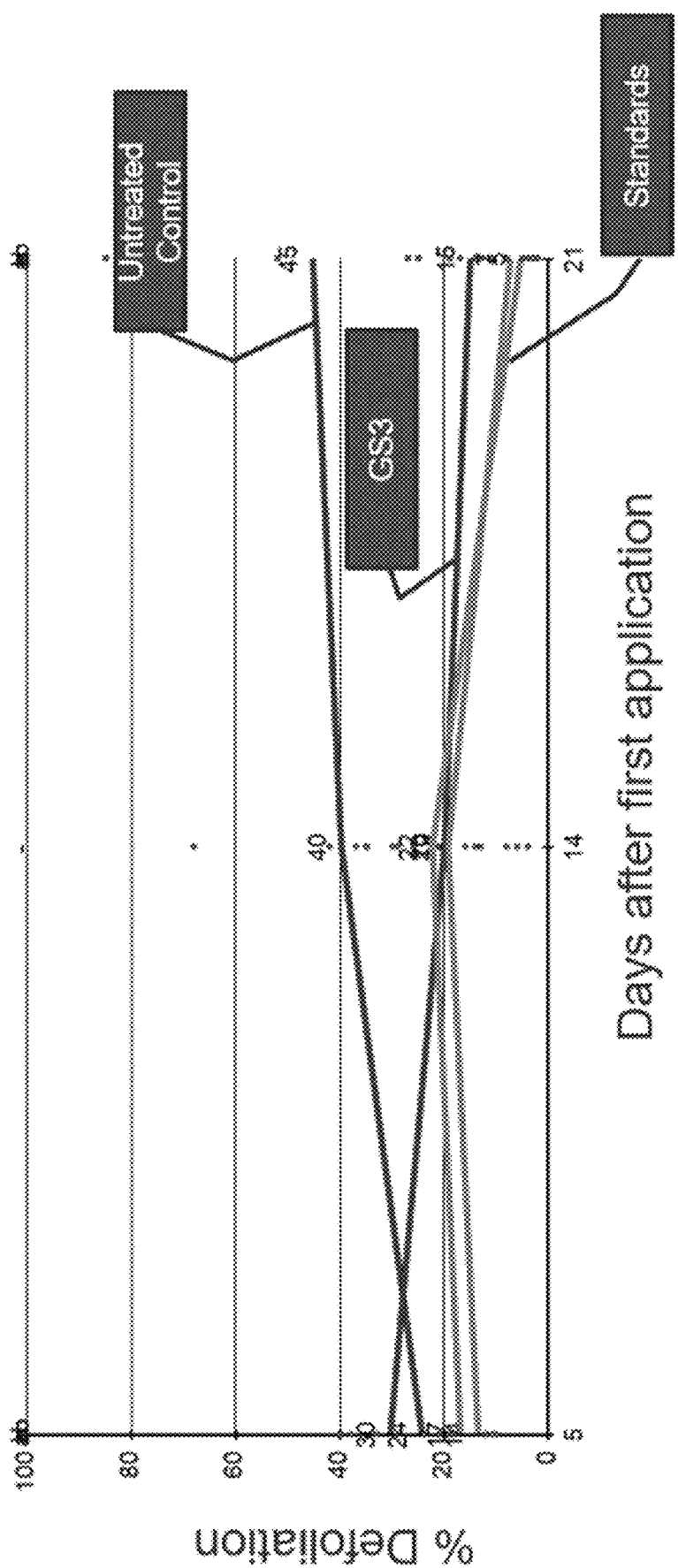

All of tested dsRNA molecules (GS3, GS167, GS168, and GS169) that bind to an mRNA encoded by a Coleopteran IAP gene caused significant time-dependent mortality in CPB insects (Tables 1-2). After nine days of exposure, GS3 caused an average 93% mortality in CPB insects; GS167 caused an average 91% mortality in CPB insects; GS168 caused an average 83% mortality in CPB insects; and GS168 caused an average 69% mortality in CPB insects. Conversely, the negative control (GS4) only caused an average 26% mortality (FIG. 5).

TABLE 2

Average mortality caused by dsRNA molecules that target length of IAP gene (combined replicates)

|  | # of Insects on Day 2 | Day 3 Mortality | Day 6 Mortality | Day 7 Mortality | Day 8 Mortality | Day 9 Mortality |
| --- | --- | --- | --- | --- | --- | --- |
| GS4 | #1: 19, #2: 19 | 0% | 11% | 18% | 21% | 26% |
| GS3 | #1: 12, #2: 20 | 20% | 73% | 85% | 89% | 93% |

TABLE 2-continued

Average mortality caused by dsRNA molecules
that target length of IAP gene (combined replicates)

|  | # of Insects on Day 2 | Day 3 Mortality | Day 6 Mortality | Day 7 Mortality | Day 8 Mortality | Day 9 Mortality |
|---|---|---|---|---|---|---|
| GS167 | #1: 15, #2: 20 | 13% | 76% | 76% | 81% | 91% |
| GS168 | #1: 16, #2: 20 | 14% | 69% | 75% | 78% | 83% |
| GS169 | #1: 14, #2: 18 | 9% | 47% | 53% | 56% | 69% |

Example 4: IAP RNAi Compositions of Minimal Length (49-200 Nucleotides) are Effective at Controlling Colorado Potato Beetles Five dsRNA molecules comprising sequences of minimal length (49-200 nucleotides) that bind to a messenger RNA (mRNA) (e.g., SEQ ID NO: 19) encoded by a Coleopteran IAP gene (e.g., SEQ ID NO: 1) were evaluated for their effectiveness to control Colorado potato beetles (CPBs). The evaluated dsRNA molecules were: GS176, GS177, GS178, GS179, GS180, GS3, and the negative control (GS4).

GS176, GS177, and GS178 were tested with GS4 and GS3 according to the procedure described in Example 3.

GS179 and GS193 were tested with GS4 and GS3 at a concentration of 0.027 using twelve eggplant leaves, each with a single 'second instar' CPB larvae. GS179 and GS180 comprised sequences of complementarity to IAP mRNA flanked by a T7 promoter and a restriction site.

All of tested dsRNA molecules comprising 100-200 nucleotides that bind to an mRNA encoded by a Coleopteran IAP gene (GS176, GS177, GS178) caused significant time-dependent mortality in CPB insects (Table 2). After nine days of exposure, the 200-nucleotide length dsRNA molecule (GS176) caused an average 89% mortality in CPB insects; the 150-nucleotide length dsRNA molecule (GS177) caused an average 95% mortality in CPB insects; and the 100-nucleotide length dsRNA molecule (GS178) caused an average 89% mortality in CPB insects. Each of these three dsRNA molecules functioned to control/kill CPB insects at similar levels as the 432-nucleotide length dsRNA molecule (GS3). Conversely, the negative control (GS4) only caused an average 26% mortality (FIG. 6A).

The dsRNA molecules comprising 49 nucleotides (GS179) and 74nucleotides (GS193), respectively, caused time-dependent mortality in CPB insects (Table 5). After eight days of exposure, the 49-nucleotide length dsRNA molecule (GS179) caused an average 56% mortality in CPB insects; and the 74-nucleotide length dsRNA molecule (GS180) caused an average 60% mortality in CPB insects. The negative control (GS4) caused an average 10% mortality (FIG. 6B).

TABLE 2

| Average mortality of two biological replicates caused by dsRNA molecules comprising 100-200 nucleotides that target IAP gene (combined replicates) | | | | | | | |
|---|---|---|---|---|---|---|---|
| | dsRNA length (nucleotides) | # of Insects on Day 2 | Day 3 | Day 6 | Day 7 | Day 8 | Day 9 |
| GS4 | 524 | #1: 19, #2: 19 | 0% | 11% | 18% | 21% | 26% |
| GS3 | 432 | #1: 12, #2: 20 | 20% | 73% | 85% | 89% | 93% |
| GS176 | 200 | #1: 14, #2: 20 | 25% | 73% | 78% | 85% | 89% |
| GS177 | 150 | #1: 18, #2: 19 | 25% | 62% | 81% | 83% | 95% |
| GS193 | 100 | #1: 15, #2: 19 | 13% | 68% | 83% | 85% | 89% |

TABLE 3

| Mortality caused by dsRNA molecules comprising 25-50 nucleotides that complementary bind to the target IAP mRNA gene | | | | | | |
|---|---|---|---|---|---|---|
| | dsRNA length (nucleotides) | # of Insects on Day 2 | Day 3 Mortality | Day 6 Mortality | Day 7 Mortality | Day 8 Mortality |
| GS4 | 524 | 10 | 0% | 0% | 10% | 10% |
| GS3 | 432 | 12 | 8% | 58% | 67% | 75% |
| GS179 | 50 | 9 | 0% | 44% | 56% | 56% |
| GS193 | 25 | 10 | 0% | 30% | 40% | 60% |

Example 5: IAP RNAi Compositions Comprising a Sequence that has 90% Complementarity to an IAP mRNA are Effective at Controlling Colorado Potato Beetles The 432-nucleotide dsRNA (GS3) that binds to a messenger RNA (mRNA) encoded by a Coleopteran IAP gene was mutated to evaluate the ability of dsRNA molecules comprising mismatches to control/kill CPB insects. The evaluated dsRNA molecules were dsRNA: (1) having 70% sequence identity to GS3 (GS170); (2) having 75% sequence identity to GS3 (GS171); (3) having 80% sequence identity to GS3 (GS172); (4) having 85% sequence identity to GS3 (GS173); (5) having 90% sequence identity to GS3 (GS174); and having 95% sequence identity to GS3 (GS175). The sequence of GS170 is 70% complementary to an mRNA encoded by an IAP gene; GS171 is 75% complementary to an mRNA encoded by an IAP gene; GS172 is 80% complementary to an mRNA encoded by an IAP gene; GS173 is 85% complementary to an mRNA encoded by an IAP gene; GS174 is 90% complementary to an mRNA encoded by an IAP gene; and GS175 is 95% complementary to an mRNA encoded by an IAP gene.

All dsRNA molecules were tested with GS4 and GS3 according to the procedure described in Example 3.

GS174 and GS175, which are, respectively, 90% and 95% complementary to an mRNA encoded by an IAP gene, caused time-dependent mortality in CPB insects (Tables 6-7). After nine days of exposure, GS174 caused an average 75% mortality in CPB insects; and GS175 caused an average 84% mortality in CPB insects. Each of these dsRNA molecules functioned to control/kill CPB insects at similar levels as the dsRNA molecule that was 100% complementary to an mRNA encoded by an IAP gene (GS3) (FIG. 7).

TABLE 4

Average Mortality of two biological replicates caused by dsRNA molecules comprising sequences with variable complementarity to an mRNA encoded by an IAP gene (combined replicates)

| | Complementarity to IAP mRNA | # of Insects on Day 2 | Day 3 Mortality | Day 6 Mortality | Day 7 Mortality | Day 8 Mortality | Day 9 Mortality |
|---|---|---|---|---|---|---|---|
| GS4 | 524 | #1: 19, #2: 19 | 0% | 11% | 18% | 21% | 26% |
| GS3 | 100% | #1: 12, #2: 20 | 20% | 73% | 85% | 89% | 93% |
| GS170 | 70% | #1: 17, #2: 19 | 3% | 8% | 19% | 22% | 28% |
| GS171 | 75% | #1: 18, #2: 18 | 3% | 17% | 25% | 28% | 33% |
| GS172 | 80% | #1: 20, #2: 19 | 5% | 33% | 44% | 44% | 49% |
| GS173 | 85% | #1: 20, #2: 19 | 8% | 13% | 23% | 26% | 33% |
| GS174 | 90% | #1: 19, #2: 18 | 13% | 51% | 65% | 70% | 75% |
| GS175 | 95% | #1: 19, #2: 17 | 17% | 67% | 81% | 81% | 84% |

Example 6: An Example IAP RNAi Composition Controls Colorado Potato Beetles in Field Trials The 432-nucleotide dsRNA (GS3) that binds to a messenger RNA (mRNA) encoded by a Coleopteran IAP gene was evaluated for its ability to control CPB insects in three open-air field trials. Briefly, in each field trial, a composition comprising GS3 (2-4 grams/acre), one or more positive control composition(s) (standards) comprising CORAGEN® (73 grams/acre), ENTRUST® (88 grams/acre), and/or NOVODOR™ (161 M Bio En/ha), or no treatment (negative control) was applied to the leaves of potato or eggplant plants in an open field. Each RNAi composition (GS3) was applied to the leaves either in four applications on a five-day interval, or three applications on a seven-day interval. The standards were applied to the leaves in three applications on seven-day intervals (Days 0, 7, and 14). Percent defoliation of the potato leaves was assessed at 2, 6, 13 and 20 days after the first application, and percent defoliation of the eggplant leaves was assessed at 5, 14, and 21 days after the first application.

In field trial #1 (FIG. 9A), potato plants that were untreated were 39% defoliated at Day 20. Conversely, potato plants treated with GS3 were 10% defoliated at Day 20; plants treated with standards (e.g. CORAGEN® and ENTRUST®) were less than 5% defoliated at Day 20.

In field trial #2 (FIG. 9B), potato plants that were untreated were 48% defoliated at Day 20. Conversely, potato plants treated with GS3 were approximately 10% defoliated at Day 20; plants treated with standards (e.g. CORAGEN®, ENTRUST®, NOVODOR™) were less than 5% defoliated at Day 20.

In field trial #3 (FIG. 9C), eggplant plants that were untreated were 45% defoliated at Day 21. Conversely, eggplant plants treated with GS3 were 15% defoliated at Day 21 and plants treated with standards (e.g. CORAGEN® and ENTRUST®) were less than 10% defoliated at Day 21.

These data demonstrate that application of IAP RNAi compositions of the disclosure prevent defoliation of plants (e.g., potato or eggplant plants) when applied to the leaves of plants in open fields (e.g., fields of crops).

Additional Embodiments

Additional embodiments of the present disclosure are encompassed by the following numbered paragraphs.

1. A polynucleotide molecule targeting a Coleopteran Inhibitor of Apoptosis (IAP) gene, wherein the polynucleotide molecule is selected from the group consisting of:

a polynucleotide molecule that binds to and inhibits expression of a messenger RNA (mRNA) encoded by a deoxynucleic acid (DNA) comprising a sequence of SEQ ID NO: 1;

a polynucleotide molecule that binds to and inhibits expression of an mRNA comprising a sequence of SEQ ID NO: 19 or SEQ ID NO: 20;

a polynucleotide molecule that comprises a sequence having at least 80% identity to a sequence of SEQ ID NO: 21 or SEQ ID NO: 39; and a polynucleotide molecule that comprises a segment that comprises at least 18 contiguous nucleotides, wherein the segment has at least 90% identity to a segment of a sequence of SEQ ID NO: 21 or SEQ ID NO: 39.

2. The polynucleotide molecule of paragraph 1, wherein the polynucleotide molecule binds to a sequence of SEQ ID NO: 21.

3. The polynucleotide molecule of paragraph 1 or 2, wherein the polynucleotide molecule comprises a sequence that has at least 85%, at least 90%, at least 95%, or at least 98% identity to a sequence of SEQ ID NO: 21 or SEQ ID NO: 39.

4. The polynucleotide molecule of paragraph 1 or 2, wherein the polynucleotide molecule comprises a segment that comprises at least 18 contiguous nucleotides, wherein the segment shares at least 95% or at least 98% identity with a sequence of SEQ ID NO: 21 or SEQ ID NO: 39.

5. The polynucleotide molecule of paragraph 3 or 4, wherein the polynucleotide molecule comprises the sequence of SEQ ID NO: 21 or SEQ ID NO: 39.

6. The polynucleotide molecule of any one of paragraphs 1-5, wherein the polynucleotide molecule is a single-stranded RNA (ssRNA) molecule, optionally comprising the sequence of SEQ ID NO: 39 or a segment of SEQ ID NO: 39.

7. The polynucleotide molecule of paragraph 6, wherein the ssRNA molecule is selected from the group consisting of small interfering RNAs (siRNAs), short hairpin RNAs (shRNAs), microRNAs (miRNAs), and antisense RNAs.

8. The polynucleotide molecule of any one of paragraphs 1-5, wherein the polynucleotide molecule is a double-stranded RNA (dsRNA) molecule, optionally comprising the sequence of SEQ ID NO: 21 or a segment of SEQ ID NO: 21.

9. A polynucleotide that specifically inhibits expression of a Coleopteran Inhibitor of Apoptosis (IAP) gene, wherein the polynucleotide comprises a first strand comprising the sequence of any one of SEQ ID NO: 21 or 23-36.

10. A polynucleotide that specifically inhibits expression of a Coleopteran Inhibitor of Apoptosis (IAP) gene, wherein the polynucleotide comprises a strand comprising the sequence of any one of SEQ ID NO: 39 or 41-54.

11. The polynucleotide of paragraph 9, wherein the polynucleotide comprises a first strand consisting of the sequence of SEQ ID NO: 21, optionally further comprising a second strand consisting of the sequence of SEQ ID NO: 39.

12. The polynucleotide of paragraph 9, wherein the polynucleotide comprises a first strand consisting of the sequence of SEQ ID NO: 23, optionally further comprising a second strand consisting of the sequence of SEQ ID NO: 41.

13. The polynucleotide of paragraph 9, wherein the polynucleotide comprises a first strand consisting of the sequence of SEQ ID NO: 24, optionally further comprising a second strand consisting of the sequence of SEQ ID NO: 42.

14. The polynucleotide of paragraph 9, wherein the polynucleotide comprises a first strand consisting of the sequence of SEQ ID NO: 25, optionally further comprising a second strand consisting of the sequence of SEQ ID NO: 43.

15. The polynucleotide of paragraph 9, wherein the polynucleotide comprises a first strand consisting of the sequence of SEQ ID NO: 26, optionally further comprising a second strand consisting of the sequence of SEQ ID NO: 44.

16. The polynucleotide of paragraph 9, wherein the polynucleotide comprises a first strand consisting of the sequence of SEQ ID NO: 27, optionally further comprising a second strand consisting of the sequence of SEQ ID NO: 45.

17. The polynucleotide of paragraph 9, wherein the polynucleotide comprises a first strand consisting of the sequence of SEQ ID NO: 28, optionally further comprising a second strand consisting of the sequence of SEQ ID NO: 46.

18. The polynucleotide of paragraph 9, wherein the polynucleotide comprises a first strand consisting of the sequence of SEQ ID NO: 29, optionally further comprising a second strand consisting of the sequence of SEQ ID NO: 47.

19. The polynucleotide of paragraph 9, wherein the polynucleotide comprises a first strand consisting of the sequence of SEQ ID NO: 30, optionally further comprising a second strand consisting of the sequence of SEQ ID NO: 48.

20. The polynucleotide of paragraph 9, wherein the polynucleotide comprises a first strand consisting of the sequence of SEQ ID NO: 31, optionally further comprising a second strand consisting of the sequence of SEQ ID NO: 49.

21. The polynucleotide of paragraph 9, wherein the polynucleotide comprises a first strand consisting of the sequence of SEQ ID NO: 32, optionally further comprising a second strand consisting of the sequence of SEQ ID NO: 50.

22. The polynucleotide of paragraph 9, wherein the polynucleotide comprises a first strand consisting of the sequence of SEQ ID NO: 33, optionally further comprising a second strand consisting of the sequence of SEQ ID NO: 51.

23. The polynucleotide of paragraph 9, wherein the polynucleotide comprises a first strand consisting of the sequence of SEQ ID NO: 34, optionally further comprising a second strand consisting of the sequence of SEQ ID NO: 52.

24. The polynucleotide of paragraph 9, wherein the polynucleotide comprises a first strand consisting of the sequence of SEQ ID NO: 35, optionally further comprising a second strand consisting of the sequence of SEQ ID NO: 53.

25. The polynucleotide of paragraph 9, wherein the polynucleotide comprises a first strand consisting of the sequence of SEQ ID NO: 36, optionally further comprising a second strand consisting of the sequence of SEQ ID NO: 54.

26. A composition comprising the polynucleotide molecule of any one of paragraphs 1-25.

27. The composition of paragraph 26, wherein the composition further comprises an additive selected from the group consisting of insect feed, insect attractants, pheromones, proteins, carbohydrates, polymers, and pesticides.

28. A method for controlling Coleopteran infestation, the method comprising contacting a plant, ground, a Coleopteran insect, or a diet of a Coleopteran insect with the polynucleotide molecule of any one of paragraph 1-25, or the composition of paragraphs 26 or 27.

29. The method of paragraph 28, wherein the Coleopteran insect is of a species selected from the group consisting of: *Leptinotarsa* spp., *Phyllotreta* spp., *Cerotoma* spp., *Diabrotica* spp., *Tribolium* spp., *Anthonomus* spp. and *Alticini* spp.

30. The method of paragraph 28 or 29, wherein the Coleopteran insect is a *Leptinotarsa* spp. insect.

31. The method of paragraph 30, wherein the *Leptinotarsa* spp. insect is a Colorado potato beetle.

32. The method of any one of paragraph 28-31, wherein the plant is selected from the group consisting of Solanaceae plants, Brassicaceae plants, Poaceae plants, Cucurbitaceae plants, Fobaceae plants, Apiaceae plants, Amaranthaceae plants, and *Malvaceae* plants.

33. The method of any one of paragraph 28-32, wherein the method impairs growth, reproduction, and/or feeding of the Coleopteran insect.

34. The method of any one of paragraphs 28-32, wherein the method results in death of the Coleopteran insect.

35. A method for producing a polynucleotide for use in insect control, the method comprising:
(a) incubating in a reaction mixture cellular ribonucleic acid (RNA) and a ribonuclease and producing 5☐ nucleoside monophosphates (5☐ NMPs);
(b) eliminating the ribonuclease; and
(c) incubating in the reaction mixture, or in a second reaction mixture, the 5☐ NMPs, a polyphosphate kinase, a polyphosphate, a polymerase, and a deoxyribonucleic acid (DNA) template having at least 80% identity to SEQ ID NO: 1, or encoding an RNA sequence that comprises a segment that comprises at least 18 contiguous nucleotides, wherein the segment has at least 90% identity to a segment of a sequence of SEQ ID NO: 2, and producing the RNA of interest, optionally wherein the reaction mixture of step (c) further comprises a nucleoside kinase, a NMP kinase, and/or a NDP kinase.

36. The method of paragraph 35, wherein the cellular RNA comprises ribosomal RNA, messenger RNA, and/or transfer RNA.

37. The method of paragraph 35 or 36, wherein the polyphosphate kinase is selected from PPK1 family enzymes and PPK2 family enzymes, and optionally wherein the polyphosphate kinase comprises a Class III polyphosphate kinase 2 from *Deinococcus geothermalis*.

38. The method of any one of paragraph 35-37, wherein the polyphosphate comprises hexametaphosphate.

39. The method according to paragraph 35, wherein the DNA template is a promotor operably linked to a nucleotide sequence encoding a desired IAP-targeting RNA, and optionally, a transcriptional terminator.

40. The method according to paragraph 39, wherein the DNA template further comprises a second template comprising a promoter operably linked to the reverse complement of the nucleotide sequence encoding a desired IAP-targeting RNA, wherein the two individual RNA molecules anneal to form a dsRNA molecule.

41. The method according to paragraph 35, wherein the DNA template is a promoter operably linked to a nucleotide sequence encoding: (a) a desired IAP RNA, (b) one or more nucleotides of a loop region of an RNA transcript, (c) the reverse compliment of the nucleotide sequence encoding the desired IAP-targeting RNA and optionally, a transcriptional terminator.

42. The method according to paragraph 35 wherein the DNA template comprises:
a. a first promoter,
b. a nucleotide sequence encoding a desired IAP-targeting RNA,
c. a second promoter, and
d. optionally, one or more transcriptional terminators,
wherein the first and second promoters are operably linked to the nucleotide sequence encoding a desired IAP-targeting RNA and wherein the bidirectional transcription of the nucleotide sequence encoding the desired IAP-targeting RNA results in complementary RNA molecules which anneal to form the dsRNA molecule 43. The method of paragraph 35, wherein the ribonuclease, the polyphosphate kinase, the DNA template, and/or the polymerase is prepared from cells that express the ribonuclease, the polyphosphate kinase, the DNA template, and/or the polymerase.

44. The method of paragraph 35, wherein the reaction mixture of (a) comprises a cell lysate prepared from cells that express the ribonuclease, the polyphosphate kinase, the DNA template, and/or the polymerase.

45. The method of paragraph 35, wherein step (b) comprises eliminating the ribonuclease and native enzymatic activities in the cell lysate via temperature, pH, salt, detergent, alcohol, and/or chemical inhibitors.

46. The method of paragraph 35, wherein step (b) comprises eliminating native enzymatic activity of enzymes in the cell lysate via separation, precipitation, filtration, capture, and/or chromatography.

47. The method of paragraph 35, wherein step (b) comprises eliminating native enzymatic activity of enzymes in the cell lysate via genetic modification, enzyme secretion from a cell, and/or protease targeting.

48. The method of any one of paragraph 45-47, wherein the native enzymatic activities are selected from phosphatases, nucleases, proteases, deaminases, and hydrolases.

49. The method of any one of paragraph 45-48, wherein the polyphosphate kinase, and/or the polymerase can withstand elimination conditions.

50. The method of paragraph 35, wherein the polymerase comprises at least one RNA polymerase.

51. A double-stranded ribonucleic acid (dsRNA) comprising a sequence with at least 80% identity to the sequence of SEQ ID NO: 3.

52. The dsRNA of paragraph 51 comprising a sequence with at least 90% or at least 95% identity to the sequence of SEQ ID NO: 3.

53. The dsRNA of paragraph 51 comprising a sequence of SEQ ID NO: 3.

54. A composition comprising the dsRNA of any one of paragraph 51-53, optionally formulated at a concentration of 0.001 µg/cm2 to 10 µg/cm2.

55. The method of paragraph 28, wherein the contacting step comprises applying the polynucleotide to the surface of the plant, ground, Coleopteran insect, or diet of a Coleopteran insect at a concentration of at least 0.001 µg/cm2.

56. The method of paragraph 55, wherein the contacting step comprises applying the polynucleotide to the surface of the plant, ground, Coleopteran insect, or diet of a Coleopteran insect at a concentration of 0.001 µg/cm2 to 10 µg/cm2.

57. The method of paragraph 56, wherein the contacting step comprises applying the polynucleotide to the surface of the plant, ground, Coleopteran insect, or diet of a Coleopteran insect at a concentration of 0.001 μg/cm2 to 0.1 μg/cm2.

58. The method of any one of paragraphs 55-57, wherein percent mortality of Coleopteran insects increase to at least 30% following fewer than 10, fewer than 9, fewer than 8, fewer than 7, fewer than 6, or fewer than 5 days of exposure of the Coleopteran insects to the polynucleotide, relative to a control, optionally under untreated conditions.

59. The method of paragraph 58, wherein percent mortality of Coleopteran insects increase to at least 40% following fewer than 10, fewer than 9, fewer than 8, fewer than 7, or fewer than 6 days of exposure of the Coleopteran insects to the polynucleotide, relative to a control, optionally under untreated conditions.

60. The method of paragraph 59, wherein percent mortality of Coleopteran insects increase to at least 50% following fewer than 10, fewer than 9, fewer than 8, or fewer than 7 days of exposure of the Coleopteran insects to the polynucleotide, relative to a control, optionally under untreated conditions.

61. The method of paragraph 60, wherein percent mortality of Coleopteran insects increase to at least 60% or at least 70% following fewer than 10, fewer than 9, or fewer than 8 days of exposure of the Coleopteran insects to the polynucleotide, relative to a control, optionally under untreated conditions.

62. The method of paragraph 60, wherein percent mortality of Coleopteran insects increase to at least 90% following fewer than 10 days or fewer than 9 days of exposure of the Coleopteran insects to the polynucleotide, relative to a control, optionally under untreated conditions.

63. The method of any one of paragraphs 55-62, wherein leaf disc consumption decrease to less than 20% following fewer than 10, fewer than 9, fewer than 8, fewer than 7, fewer than 6, or fewer than 5 days of exposure of Coleopteran insects to the polynucleotide, relative to a control, optionally under untreated conditions.

64. The method of paragraph 63, wherein leaf disc consumption decrease to less than 10% following fewer than 10% following fewer than 10, fewer than 9, fewer than 8, fewer than 7, fewer than 6, or fewer than 5 days of exposure of Coleopteran insects to the polynucleotide, relative to a control, optionally under untreated conditions.

65. The method of any one of paragraphs 55-64, wherein percent plant defoliation decreases to less than 10% following fewer than 10, fewer than 9, fewer than 8, fewer than 7, fewer than 6, fewer than 5, or fewer than 4 days of exposure of Coleopteran insects to the polynucleotide, relative to a control, optionally under untreated conditions.

66. The method of any one of paragraphs 55-65, wherein percent plant defoliation remains less than 10% following at least 10, at least 15, or at least 20 days following exposure of Coleopteran insects to the polynucleotide, relative to a control, optionally under untreated conditions.

TABLE 8

| | | Sequences, 5'→3' | |
|---|---|---|---|
| Description | Length (bp) | Sequence | SEQ ID NO: |
| | | DNA | |
| TAP | 1564 | CTAATGCATTGCGTTGTTCAGATACAAACGTACGTGCA GTTCAGTTCAGTTCAGTTCTCGTATCGCTAGTTTGTCG GAGCAATTGGTTCACTTGGTATTTGGGGCGATTTTAAC GTGTTTTTTACGAAGGATCTTATAAAAATCATGCAGTG TTACAGCATCATATTTTTTGGTACTGAGAAGGCATGAA AATGAATCAAACATTTCCCACAATCAGCAGTTACTCTG ATCAGACAGACAATAACCCCAAACATAAAAGTTTTTTT GAAGTAAACGTCAACAATTCCGCATTGGAGGCGAGAC TGAGAACATTTGACAATTGGCCAAGCACACAACTATC CAAGGAAGCGCTCGCGTCTGCCGGTTTTGAATACACTG GACAAGATGACATTGTTTTGTGTCGTTTCTGTAAGATA GAAGGATACAATTGGGTATCTGGAGATGATCCAATGG CAGACCATCGAGAATGGAGTCCTGACTGTCCTTTTATT AGAACTGTAGAGAACGGCAGGTCTGGGAGTAATAGAA ACGCAGATACTTGTGGACTGTACGGCATAGAGGTTCTT CCAAATTCCCTCCCGGAGGACAGGAGATCCATTGATTT GCAACAGTTGGGAATCCACAAAGGAAGTGGACCACAC AACCAGGATAAAATAACGGTAAATAGTCGACTAGCAA CGTTCGAAAACTGGCCCAAGTCCATCAAGCAGAGACC CGTTGATTTGGCAGAAGCGGGATTTTATTATACCGGTG TGGGAGACCAGACACTTTGTTTCTACTGTGGTGGTGGT CTAAAAGACTGGGAAGAATCTGACGAACCTTGGGAAC AACACGCCCTTTGGTTCAGCAAGTGTGTTTTTCTAAAT TTGAAAAAAGGTAAAGACTTTGTCGAAAAGGTCAAAC AGAGGGCAGACCCTCTCTTGTCGCTCCCCGGAACAAG TCAAGACAAGACCAAAGAGCTAGAAGAACCTAAAGA GCCCTGCAGTAGGACTCCAGAAAAGGCTGAAAAGACT ACTGAAACGGAAGCAACAGAGAAGACTTTGTGTAAAA TCTGTTATAAAAACGAACTTGGTGTTGTATTCTTGCCT TGTGGACATGTTGTTGCTTGTGTAGATTGTGCTTCTGCT TTGAAAACTTGTGCTGTCTGTAGGAAACCTTTGGAAGC GACAGTTCGAGCATTTCTCTCATAATTTTTCCATTCTTT AATTTTCGTTTCTCAGATCTAGTCAATTTGAATTTGATT CTTGAAGGTTTATTAAAAGTTTTGTCAAAATTATTC TTTTCTTGTTTTAGGATTAGAAGTAAATCTATTTTTATA CAATCTGAGTACAAATTCCACATACTTTTTTAGTTATA AGTTTGAAGCGCTTATGAAACATACTTTTAGTTCATTA | 1 |

TABLE 8-continued

Sequences, 5'→3'

| Description | Length (bp) | Sequence | SEQ ID NO: |
|---|---|---|---|
| | | ATGACTGCAAACCATATCTTTCGTACACTAATACTTAT<br>TAGTTATCAAGCTCTCGTGAGTGGAACTTCCTTATTAG<br>AACATTTTATTATAAAACTGACACAGAGATATATCTGT<br>ATGTTTGTGTGTATGTTCACTAAGTATGCTAATAATAT<br>AATAATTTATGAAAAA | |
| TAP | 1453 | CTAATGCATTGCGTTGTTCAGATACAAACGTACGTGCA<br>GTTCAGTTCAGTTCAGTTCTCGTATCGCTAGTTGGCAT<br>GAAAATGAATCAAACATTTCCCACAATCAGCAGTTAC<br>TCTGATCAGACAGACAATAACCCCAAACATAAAAGTT<br>TTTTTGAAGTAAACGTCAACAATTCCGCATTGGAGGCG<br>AGACTGAGAACATTTGACAATTGGCCAAGCACACAAC<br>TATCCAAGGAAGCGCTCGCGTCTGCCGGTTTTGAATAC<br>ACTGGACAAGATGACATTGTTTTGTGTCGTTTCTGTAA<br>GATAGAAGGATACAATTGGGTATCTGGAGATGATCCA<br>ATGGCAGACCATCGAGAATGGAGTCCTGACTGTCCTTT<br>TATTAGAACTGTAGAGAACGGCAGGTCTGGGAGTAAT<br>AGAAACGCAGATACTTGTGGACTGTACGGCATAGAGG<br>TTCTTCCAAATTCCCTCCCGGAGGACAGGAGATCCATT<br>GATTTGCAACAGTTGGGAATCCACAAAGGAAGTGGAC<br>CACACAACCAGGATAAAATAACGGTAAATAGTCGACT<br>AGCAACGTTCGAAAACTGGCCCAAGTCCATCAAGCAG<br>AGACCCGTTGATTTGGCAGAAGCGGGATTTTATTATAC<br>CGGTGTGGGAGACCAGACACTTTGTTTCTACTGTGGTG<br>GTGGTCTAAAAGACTGGGAAGAATCTGACGAACCTTG<br>GGAACAACACGCCCTTTGGTTCAGCAAGTGTGTTTTTC<br>TAAATTTGAAAAAAGGTAAAGACTTTGTCGAAAAGGT<br>CAAACAGAGGGCAGACCCTCTCTTGTCGCTCCCCGGA<br>ACAAGTCAAGACAAGACCAAAGAGCTAGAAGAACCT<br>AAAGAGCCCTGCAGTAGGACTCCAGAAAAGGCTGAAA<br>AGACTACTGAAACGGAAGCAACAGAGAAGACTTTGTG<br>TAAAATCTGTTATAAAAACGAACTTGGTGTTGTATTCT<br>TGCCTTGTGGACATGTTGTTGCTTGTGTAGATTGTGCTT<br>CTGCTTTGAAAACTTGTGCTGTCTGTAGGAAACCTTTG<br>GAAGCGACAGTTCGAGCATTTCTCTCATAATTTTTCCA<br>TTCTTTAATTTTCGTTTCTCAGATCTAGTCAATTTGAAT<br>TTGATTCTTGAAGGTTTATTAAAAAGTTTTGTCAAAAA<br>TTATTCTTTTCTTGTTTTAGGATTAGAAGTAAATCTATT<br>TTTTATACAATCTGAGTACAAATTCCACATACTTTTTTA<br>GTTATAAGTTTGAAGCGCTTATGAAACATACTTTTAGT<br>TCATTAATGACTGCAAACCATATCTTTCGTACACTAAT<br>ACTTATTAGTTATCAAGCTCTCGTGAGTGGAACTTCCT<br>TATTAGAACATTTTATTATAAAACTGACACAGAGATAT<br>ATCTGTATGTTTGTGTGTATGTTCACTAAGTATGCTAA<br>TAATATAATAATTTATGAAAAA | 2 |
| GS3 | 432 bp | GGTGTGGGAGACCAGACACTTTGTTTCTACTGTGGTGG<br>TGGTCTAAAAGACTGGGAAGAATCTGACGAACCTTGG<br>GAACAACACGCCCTTTGGTTCAGCAAGTGTGTTTTTCT<br>AAATTTGAAAAAAGGTAAAGACTTTGTCGAAAAGGTC<br>AAACAGAGGGCAGACCCTCTCTTGTCGCTCCCCGGAA<br>CAAGTCAAGACAAGACCAAAGAGCTAGAAGAACCTA<br>AAGAGCCCTGCAGTAGGACTCCAGAAAAGGCTGAAAA<br>GACTACTGAAACGGAAGCAACAGAGAAGACTTTGTGT<br>AAAATCTGTTATAAAAACGAACTTGGTGTTGTATTCTT<br>GCCTTGTGGACATGTTGTTGCTTGTGTAGATTGTGCTT<br>CTGCTTTGAAAACTTGTGCTGTCTGTAGGAAACCTTTG<br>GAAGCGACAGTTCGAGCATTT | 3 |
| GS4 (negative control) | 524 bp | ATGGTGAGCAAGGGCGAGGAGCTGTTCACCGGGGTGG<br>TGCCCATCCTGGTCGAGCTGGACGGCGACGTAAACGG<br>CCACAAGTTCAGCGTGTCCGGCGAGGGCGAGGGCGAT<br>GCCACCTACGGCAAGCTGACCCTGAAGTTCATCTGCAC<br>CACCGGCAAGCTGCCCGTGCCCTGGCCCACCCTCGTGA<br>CCACCCTGACCTACGGCGTGCAGTGCTTCAGCCGCTAC<br>CCCGACCACATGAAGCAGCACGACTTCTTCAAGTCCG<br>CCATGCCCGAAGGCTACGTCCAGGAGCGCACCATCTT<br>CTTCAAGGACGACGGCAACTACAAGACCCGCGCCGAG<br>GTGAAGTTCGAGGGCGACACCCTGGTGAACCGCATCG<br>AGCTGAAGGGCATCGACTTCAAGGAGGACGGCAACAT<br>CCTGGGGCACAAGCTGGAGTACAACTACAACAGCCAC<br>AACGTCTATATCATGGCCGACAAGCAGAAGAACGGCA<br>TCAAGGTGAACTTCAAGATCCGCCACAACATCGAGGA<br>CGG | 4 |

TABLE 8-continued

Sequences, 5'→3'

| Description | Length (bp) | Sequence | SEQ ID NO: |
|---|---|---|---|
| GS167 dsRNA target 5' region | 521 bp | CTAATGCATTGCGTTGTTCAGATACAAACGTACGTGCA GTTCAGTTCAGTTCAGTTCTCGTATCGCTAGTTTGTCG GAGCAATTGGTTCACTTGGTATTTGGGGCGATTTTAAC GTGTTTTTTACGAAGGATCTTATAAAAATCATGCAGTG TTACAGCATCATATTTTTTGGTACTGAGAAGGCATGAA AATGAATCAAACATTTCCCACAATCAGCAGTTACTCTG ATCAGACAGACAATAACCCCAAACATAAAAGTTTTTTT GAAGTAAACGTCAACAATTCCGCATTGGAGGCGAGAC TGAAACATTTGACAATTGGCCAAGCACACAACTATC CAAGGAAGCGCTCGCGTCTGCCGGTTTTGAATACACTG GACAAGATGACATTGTTTTGTGTCGTTTCTGTAAGATA GAAGGATACAATTGGGTATCTGGAGATGATCCAATGG CAGACCATCGAGAATGGAGTCCTGACTGTCCTTTTATT AGAACTGTAGAGAACGGCAGGTCTGGGAGT | 5 |
| GS168 dsRNA target central region | 522 bp | AATAGAAACGCAGATACTTGTGGACTGTACGGCATAG AGGTTCTTCCAAATTCCCTCCCGGAGGACAGGAGATCC ATTGATTTGCAACAGTTGGGAATCCACAAAGGAAGTG GACCACACAACCAGGATAAAATAACGGTAAATAGTCG ACTAGCAACGTTCGAAAACTGGCCCAAGTCCATCAAG CAGAGACCCGTTGATTTGGCAGAAGCGGGATTTTATTA TACCGGTGTGGGAGACCAGACACTTTGTTTCTACTGTG GTGGTGGTCTAAAAGACTGGGAAGAATCTGACGAACC TTGGGAACAACACGCCCTTTGGTTCAGCAAGTGTGTTT TTCTAAATTTGAAAAAAGGTAAAGACTTTGTCGAAAA GGTCAAACAGAGGGCAGACCCTCTCTTGTCGCTCCCCG GAACAAGTCAAGACAAGACCAAAGAGCTAGAAGAAC CTAAAGAGCCCTGCAGTAGGACTCCAGAAAAGGCTGA AAAGACTACTGAAACGGAAGCAACAGAGAAGACTTTG | 6 |
| GS169 dsRNA target 3' region | 521 bp | TGTAAAATCTGTTATAAAAACGAACTGGTGTTGTATT CTTGCCTTGTGGACATGTTGTTGCTTGTGTAGATTGTG CTTCTGCTTTGAAAACTTGTCTGTCTGTAGGAAACCT TTGGAAGCGACAGTTCGAGCATTTCTCTCATAATTTTT CCATTCTTTAATTTTCGTTTCTCAGATCTAGTCAATTTG AATTTGATTCTTGAAGGTTTATTAAAAAGTTTTGTCAA AAATTATTCTTTTCTTGTTTTAGGATTAGAAGTAAATCT ATTTTTTATACAATCTGAGTACAAATTCCACATACTTTTT TAGTTTATAAGTTTGAAGCGCTTATGAAACATACTTTTA GTTCATTAATGACTGCAAACCATATCTTTCGTACACTA ATACTTATTAGTTATCAAGCTCTCGTGAGTGGAACTTC CTTATTAGAACATTTTATTATAAAACTGACACAGAGAT ATATCTGTATGTTTGTGTATGTTCACTAAGTATGCT AATAATATAATAATTTATGAAAAA | 7 |
| GS170 dsRNA target 70% identity to GS3 | 432 bp | GATGAGTGACTGCAGAATCTTTGTTTCCGCTGAGGTTA TTGGCTTGAACACTAGGAAAGAGGTTATGAACCTTGG TAACTACACACCATTTGATGCAGCAAGCGTGATCTTCT AAATTAGTTAGCAATGAAAGCCTTTGTCTAAGGGGTG AACCAGCGTGCCGAGCCTCTCTAGCCCCTCTCTGACAC AAGTCAAAACATGATCATTGGGCTTGTAGAGCCTCGA GAGGTCTGCAGTAGAACACCAGACCAGGCTGGAAAGT CTCCTGAAACAGATCCACCAGAGGAGACGTAGTTGAA AATCCGTTATAGAATCGAACTTCGCGTTGTACCACGGC TTTATAGGCAACCAGTTACTTGTCTAGATTGTGCTTCA GCTACTAGAAATTGTGCTGAAAGGAGGAAACCACTGC AAGGGCTGGAACGGGGATTA | 8 |
| GS171 dsRNA target 75% identity to GS3 | 432 bp | AGTGTTTTAAAAACGCCCCTTTTTGGCTACTGTAGTTG TAGTTTCAAAAACTGTGAAGAATCGGACGATCATTGG GAACAACACGCGCTTTCGTTCAGCAAGTGGACTTCTAG AACTTTGAAAAAGGTAATGACACAGTTGAGGAGGTC AAACTGAGGGCACACGCTCTCTTGTCGCAGCCGGGAA CAAGACAAGACATGACCAATAAGATAGAAGGACATAC AGGCTCATTGAGTAGGGCTCGAGAAAAAGGTCAAAG ACTACTGATACGGAACCCCCACAGCACACATTGTCTAC TATCTGACCTAAGATCTGACCTGGTGTTATATTCTTGA CCTGTGGACCTGTTGTGGCTTGCCTAGATTGAGCTACT GACATGAAAATATCTGATGTCTGTAGGAAGCATACGG AAGCGACGGCATGCGCATTT | 9 |
| GS172 dsRNA target 80% identity | 432 bp | GTTGTGGGAGACCAGTCTATGTGGTGCAACTATACTGG TGGTCATAAAAACTGGGACATATCAGACGTACCTCGG GTAGAACCCGCGCTTGGGTTCAGGAAGTGTGTTTTGCT AAAAAATGATATAAGCTCAAGACTTTGTCGAAAACGAC | 10 |

TABLE 8-continued

| Description | Length (bp) | Sequence | SEQ ID NO: |
|---|---|---|---|
| to GS3 | | AACCAGAGGGAAGAACATCTCTTGTCGCTCTCCGAAA<br>CAACTCAAAACAAGACCAAAAAGATAGAGGTATCGGA<br>AGAGCCCAGCCAGTAGGAGCCTCGAACAGGCTGAAGAG<br>ACTACTAAGAGGGACGCTACAGAGCACACTTTGACTA<br>AGATCTGTTAAAAAGACGAGCTTGGTTTAGTTTTCTTA<br>CCTGGTTGACTTGTTGTTGCCTGTCGAAATTGTGCTTCT<br>GCTTTGAAAACTTGTGCTGTCTGTAGGCAACCTTTGGA<br>ATCGACAGTTAGCGCATTC | |
| GS173 dsRNA target 85% identity to GS3 | 432 bp | GGTGTAGGAGACCAGACACTCTGTTTCTACTGAGGTGC<br>TCGTCTAGGAGACCGTGTAGAATCTAACGAACCTTGG<br>GAACAACACGCCCTTTGTTTCAGCCAGTGTGATTTTCA<br>AAATGTGAAATAAGGTTAAGACTTTGTCGGCAAGGTC<br>AAACAGAGGCCAGACCATCTCTTGACGCGCCCCGTAA<br>CAAGTCAAGAAAATACCAACGAGCTACAAGAACATAA<br>AGAGCGCTGCAGTAGGACTCCGGAAAAGGTTGAGAAG<br>ACTACTGAAAGGGAAGCAAGAGGTAAGGCTATGTGTT<br>AATTCTTTTATAAAGACTTTCTTGGTGTCGTATATTTGC<br>CTTGTGGCCATGTTGTTGCTCGTGTAGGTTGTTCTTCTG<br>CTTAAGCAACTTGTGCTGTATGTAGCAAACTTTTGCCA<br>GCGGCAGTTCGAGCATTT | 11 |
| GS174 dsRNA target 90% identity to GS3 | 432 bp | GGTGTGGGAGAGCAGACACTTCGTTTCTACAGTGGTG<br>GCGGTCTAAAAGACTGGGAAGAATCTGACGAGCCTTG<br>CGAACAACAGGCACTTGGGTTCAGCAAGTTTGCTTTTC<br>TGAATTTGAAAAAATGTTAAGACCTTGTCGGAAAGGT<br>CAAACAGAGGCCAGACCCTCTCTTGTGGCACCCCTGA<br>ACAAGTCAAGACAAGACCACAGGCCGAGAAGAACCT<br>AAAGAGCCCTGCAGCAGGACTCCAGACAAGGCTGAAA<br>AGACTACTGCAACGGAAGCAGGAGAAAAGGCTTTGTG<br>TAAAATCTGTTCTAAAAACGAACTTGGAGTTGTATTCT<br>GGCCTTGTGGCCATGTTGTTGCGGGTGTCGATTGTGCG<br>TCTGCTTTGAATACTTGTGCTGTCCTTAGGAAACCTTT<br>GGAAGCGACAGTTCGAGCAATT | 12 |
| GS175 dsRNA target 95% identity to GS3 | 432 bp | GGTGTGGGAGACCAGACACTTTGTTTCTACTGTGATGG<br>TGGTCTAAAAGACTGGGAAAAATCTGACGAACCTTGG<br>GTACAACACGGCCTTTGGTTCAGCAAGTGTGTCTTTAT<br>AAATTTGAAAAAGGTAAAGACTTTGGCGAAAAGGTC<br>AAGCAGAGGGCAATCCCTCTCTTGTCGCACCCCGGAA<br>CAAGTCAAGACAAGACCAAAGAGCTAGACGAACCTAA<br>AGAGCCCTGCAGTAGGACTCCAGAAAAGGCTGAAAAG<br>ACTACTGAAACGGAAGCCACAGAGAAGACTTTGTGTA<br>AAATCTGTTATAAAAACCAACTTGATGTTGTTTTCTTG<br>CCATGTGGACATTTTGTTGCTTGTGGAGCTTGTGCTTCT<br>GCTTTGAAAACTTGTGCTGTCTGTAGGAAACCTTTGGA<br>AGCGACAGTTCGAGCATTC | 13 |
| GS176 dsRNA target Nucleotides (nt) 160-360 of GS3 | 200 bp | GCAGACCCTCTCTTGTCGCTCCCCGGAACAAGTCAAGA<br>CAAGACCAAAGAGCTAGAAGAACCTAAAGAGCCCTGC<br>AGTAGGACTCCAGAAAAGGCTGAAAAGACTACTGAAA<br>CGGAAGCAACAGAGAAGACTTTGTGTAAAATCTGTTA<br>TAAAAACGAACTTGGTGTTGTATTCTTGCCTTGTGGAC<br>ATGTTGTTGCTTG | 14 |
| GS177 dsRNA target nt 185-335 of GS3 | 150 bp | GAACAAGTCAAGACAAGACCAAAGAGCTAGAAGAAC<br>CTAAAGAGCCCTGCAGTAGGACTCCAGAAAAGGCTGA<br>AAAGACTACTGAAACGGAAGCAACAGAGAAGACTTTG<br>TGTAAAATCTGTTATAAAAACGAACTTGGTGTTGTATT<br>CT | 15 |
| GS178 dsRNA target nt 210-310 of GS3 | 100 bp | GCTAGAAGAACCTAAAGAGCCCTGCAGTAGGACTCCA<br>GAAAAGGCTGAAAAGACTACTGAAACGGAAGCAACA<br>GAGAAGACTTTGTGTAAAATCTGTTAT | 16 |
| GS179 dsRNA target nt 235-385 of GS3 | 50 bp/<br>74 bp* | AGTAGGACTCCAGAAAAGGCTGAAAAGACTACTGAAA<br>CGGAAGCAACAGA/<br>GGGAGAagatctAGTAGGACTCCAGAAAAGGCTGAAAAG<br>ACTACTGAAACGGAAGCAACAGAggtaccTCTCCC | 17 |

TABLE 8-continued

Sequences, 5'→3'

| Description | Length (bp) | Sequence | SEQ ID NO: |
|---|---|---|---|
| GS180 dsRNA target nt 247-272 of GS3 | 25 bp/ 49 bp* | GAAAAGGCTGAAAAGACTACTGAAA/ GGGAGAagatctGAAAAGGCTGAAAAGACTACTGAAAggt accTCTCCC | 18 |

RNA STRANDS

| | | | |
|---|---|---|---|
| TAP mRNA | 1564 | CUAAUGCAUUGCGUUGUUCAGAUACAAACGUACGUG CAGUUCAGUUCAGUUCAGUUCUCGUAUCGCUAGUUU GUCGGAGCAAUUGGUUCACUUGGUAUUUGGGGCGAU UUUAACGUGUUUUUUACGAAGGAUCUUAUAAAAAUC AUGCAGUGUUACAGCAUCAUAUUUUUUGGUACUGAG AAGGCAUGAAAAUGAAUCAAACAUUUCCCACAAUCA GCAGUUACUCUGAUCAGACAGACAAUAACCCCAAAC AUAAAAGUUUUUUGAAGUAAACGUCAACAAUUCCG CAUUGGAGGCGAGACUGAGAACAUUUGACAAUUGGC CAAGCACACAACUAUCCAAGGAAGCGCUCGCGUCUG CCGGUUUUGAAUACACUGGACAAGAUGACAUUGUUU UGUGUCGUUUCUGUAAGAUAGAAGGAUACAAUUGGG UAUCUGGAGAUGAUCCAAUGGCAGACCAUCGAGAAU GGAGUCCUGACUGUCCUUUUAUUAGAACUGUAGAGA ACGGCAGGUCUGGGAGUAAUAGAAACGCAGAUACUU GUGGACUGUACGGCAUAGAGGUUCUUCCAAAUUCCC UCCCGGAGGACAGGAGAUCCAUUGAUUUGCAACAGU UGGGAAUCCACAAAGGAAGUGGACCACACAACCAGG AUAAAAUAACGGUAAAUAGUCGACUAGCAACGUUCG AAAACUGGCCCAAGUCCAUCAAGCAGAGACCCGUUG AUUUGGCAGAAGCGGGAUUUUAUUAUACCGGUGUGG GAGACCAGACACUUUGUUUCUACUGUGGUGGUGGUC UAAAAGACUGGGAAGAAUCUGACGAACCUUGGGAAC AACACGCCCUUUGGUUCAGCAAGUGUGUUUUUCUAA AUUUGAAAAAAGGUAAAGACUUUGUCGAAAAGGUCA AACAGAGGGCAGACCCUCUCUUGUCGCUCCCCGGAA CAAGUCAAGACAAGACCAAAGAGCUAGAAGAACCUA AAGAGCCCUGCAGUAGGACUCCAGAAAAGGCUGAAA AGACUACUGAAACGGAAGCAACAGAGAAGACUUUGU GUAAAAUCUGUUAUAAAAACGAACUUGGUGUUGUAU UCUUGCCUUGUGGACAUGUUGUUGCUUGUGUAGAUU GUGCUUCUGCUUUGAAAACUUGUGCUGUCUGUAGGA AACCUUUGGAAGCGACAGUUCGAGCAUUUCUCUCAU AAUUUUCCAUUCUUUAAUUUUCGUUUCUCAGAUCU AGUCAAUUUGAAUUUGAUUCUUGAAGGUUUAUUAAA AAGUUUUGUCAAAAAUUAUUCUUUUCUUGUUUUAGG AUUAGAAGUAAAUCUAUUUUUAUACAAUCUGAGUAC AAAUUCCACAUACUUUUUUAGUUAUAAGUUUGAAGC GCUUAUGAAACAUACUUUUAGUUCAUUAAUGACUGC AAACCAUAUCUUUCGUACACUAAUACUUAUUAGUUA UCAAGCUCUCGUGAGUGGAACUUCCUUAUUAGAACA UUUUAUUAUAAAACUGACACAGAGAUAUAUCUGUAU GUUUGUGUGUAUGUUCACUAAGUAUGCUAAUAAUAU AAUAAUUUAUGAAAAA | 19 |
| TAP mRNA | 1453 | CUAAUGCAUUGCGUUGUUCAGAUACAAACGUACGUG CAGUUCAGUUCAGUUCAGUUCUCGUAUCGCUAGUUG GCAUGAAAAUGAAUCAAACAUUUCCCACAAUCAGCA GUUACUCUGAUCAGACAGACAAUAACCCCAAACAUA AAGUUUUUUGAAGUAAACGUCAACAAUUCCGCAU UGGAGGCGAGACUGAGAACAUUUGACAAUUGGCCAA GCACACAACUAUCCAAGGAAGCGCUCGCGUCUGCCG GUUUUGAAUACACUGGACAAGAUGACAUUGUUUUGU GUCGUUUCUGUAAGAUAGAAGGAUACAAUUGGGUAU CUGGAGAUGAUCCAAUGGCAGACCAUCGAGAAUGGA GUCCUGACUGUCCUUUUAUUAGAACUGUAGAGAACG GCAGGUCUGGGAGUAAUAGAAACGCAGAUACUUGUG GACUGUACGGCAUAGAGGUUCUUCCAAAUUCCCUCC CGGAGGACAGGAGAUCCAUUGAUUUGCAACAGUUGG GAAUCCACAAAGGAAGUGGACCACACAACCAGGAUA AAAUAACGGUAAAUAGUCGACUAGCAACGUUCGAAA ACUGGCCCAAGUCCAUCAAGCAGAGACCCGUUGAUU UGGCAGAAGCGGGAUUUUAUUAUACCGGUGUGGGAG ACCAGACACUUUGUUUCUACUGUGGUGGUGGUCUAA AAGACUGGGAAGAAUCUGACGAACCUUGGGAACAAC ACGCCCUUUGGUUCAGCAAGUGUGUUUUUCUAAAUU UGAAAAAAGGUAAAGACUUUGUCGAAAAGGUCAAAC | 20 |

TABLE 8-continued

Sequences, 5'→3'

| Description | Length (bp) | Sequence | SEQ ID NO: |
|---|---|---|---|
| | | AGAGGGCAGACCCUCUCUUGUCGCUCCCCGGAACAA GUCAAGACAAGACCAAAGAGCUAGAAGAACCUAAAG AGCCCUGCAGUAGGACUCCAGAAAAGGCUGAAAAGA CUACUGAAACGGAAGCAACAGAGAAGACUUUGUGUA AAAUCUGUUAUAAAAACGAACUUGGUGUUGUAUUCU UGCCUUGUGGACAUGUUGUUGCUUGUGUAGAUUGUG CUUCUGCUUUGAAAACUUGUGCUGUCUGUAGGAAAC CUUUGGAAGCGACAGUUCGAGCAUUUCUCUCAUAAU UUUUCCAUUCUUUAAUUUUCGUUUCUCAGAUCUAGU CAAUUUGAAUUGAUUCUUGAAGGUUUAUUAAAAAG UUUUGUCAAAAAUUAUUCUUUUCUUGUUUUAGGAUU AGAAGUAAAUCUAUUUUUAUACAAUCUGAGUACAAA UUCCACAUACUUUUUUAGUUAUAAGUUUGAAGCGCU UAUGAAACAUACUUUUAGUUCAUUAAUGACUGCAAA CCAUAUCUUUCGUACACUAAUACUUAUUAGUUAUCA AGCUCUCGUGAGUGGAACUUCCUUAUUAGAACAUUU UAUUAUAAAACUGACACAGAGAUAUAUCUGUAUGUU UGUGUGUAUGUUCACUAAGUAUGCUAAUAAUAUAAU AAUUUAUGAAAAA | |
| GS3 | 432 bp | GGUGUGGGAGACCAGACACUUUGUUUCUACUGUGGU GGUGGUCUAAAAGACUGGGAAGAAUCUGACGAACCU UGGGAACAACACGCCCUUUGGUUCAGCAAGUGUGUU UUUCUAAAUUUGAAAAAAGGUAAAGACUUUGUCGAA AAGGUCAAACAGAGGGCAGACCCUCUCUUGUCGCUC CCCGGAACAAGUCAAGACAAGACCAAAGAGCUAGAA GAACCUAAAGAGCCCUGCAGUAGGACUCCAGAAAAG GCUGAAAAGACUACUGAAACGGAAGCAACAGAGAAG ACUUUGUGUAAAAUCUGUUAUAAAAACGAACUUGGU GUUGUAUUCUUGCCUUGUGGACAUGUUGUUGCUUGU GUAGAUUGUGCUUCUGCUUUGAAAACUUGUGCUGUC UGUAGGAAACCUUUGGAAGCGACAGUUCGAGCAUUU | 21 |
| GS4 (negative control) | 524 bp | AUGGUGAGCAAGGGCGAGGAGCUGUUCACCGGGGUG GUGCCCAUCCUGGUCGAGCUGGACGGCGACGUAAAC GGCCACAAGUUCAGCGUGUCCGGCGAGGGCGAGGGC GAUGCCACCUACGGCAAGCUGACCCUGAAGUUCAUC UGCACCACCGGCAAGCUGCCCGUGCCCUGGCCCACCC UCGUGACCACCCUGACCUACGGCGUGCAGUGCUUCA GCCGCUACCCCGACCACAUGAAGCAGCACGACUUCUU CAAGUCCGCCAUGCCCGAAGGCUACGUCCAGGAGCG CACCAUCUUCUUCAAGGACGACGGCAACUACAAGAC CCGCGCCGAGGUGAAGUUCGAGGGCGACACCCUGGU GAACCGCAUCGAGCUGAAGGGCAUCGACUUCAAGGA GGACGGCAACAUCCUGGGGCACAAGCUGGAGUACAA CUACAACAGCCACAACGUCUAUAUCAUGGCCGACAA GCAGAAGAACGGCAUCAAGGUGAACUUCAAGAUCCG CCACAACAUCGAGGACGG | 22 |
| GS167 dsRNA strand 5' region | 521 bp | CUAAUGCAUUGCGUUGUUCAGAUACAAACGUACGUG CAGUUCAGUUCAGUUCAGUUCUCGUAUCGCUAGUUU GUCGGAGCAAUUGGUUCACUUGGUAUUUGGGGCGAU UUUUAACGUGUUUUUUACGAAGGAUCUUAUAAAAAUC AUGCAGUGUUACAGCAUCAUAUUUUUUGGUACUGAG AAGGCAUGAAAAUGAAUCAAACAUUUCCCACAAUCA GCAGUUACUCUGAUCAGACAGACAAUAACCCCAAAC AUAAAAGUUUUUUUGAAGUAAACGUCAACAAUUCCG CAUUGGAGGCGAGACUGAGAACAUUUGACAAUUGGC CAAGCACACAACUAUCCAAGGAAGCGCUCGCGUCUG CCGGUUUUGAAUACACUGGACAAGAUGACAUUGUUU UGUGUCGUUUCUGUAAGAUAGAAGGAUACAAUUGGG UAUCUGGAGAUGAUCCAAUGGCAGACCAUCGAGAAU GGAGUCCUGACUGUCCUUUUAUUAGAACUGUAGAGA ACGGCAGGUCUGGGAGU | 23 |
| GS168 dsRNA strand central region | 522 bp | AAUAGAAACGCAGAUACUUGUGGACUGUACGGCAUA GAGGUUCUUCCAAAUUCCCUCCCGGAGGACAGGAGA UCCAUUGAUUUGCAACAGUUGGGAAUCCACAAAGGA AGUGGACCACACAACCAGGAUAAAAUAACGGUAAAU AGUCGACUAGCAACGUUCGAAAACUGGCCCAAGUCC AUCAAGCAGAGACCCGUUGAUUUGGCAGAAGCGGGA UUUUAUUAUACCGGUGUGGGAGACCAGACACUUUGU UUCUACUGUGGUGGUGGUCUAAAAGACUGGGAAGAA UCUGACGAACCUUGGGAACAACACGCCCUUUGGUUC AGCAAGUGUGUUUUUCUAAAUUUGAAAAAAGGUAAA | 24 |

TABLE 8-continued

Sequences, 5'→3'

| Description | Length (bp) | Sequence | SEQ ID NO: |
|---|---|---|---|
| | | GACUUUGUCGAAAAGGUCAAACAGAGGGCAGACCCU CUCUUGUCGCUCCCCGGAACAAGUCAAGACAAGACC AAAGAGCUAGAAGAACCUAAAGAGCCCUGCAGUAGG ACUCCAGAAAAGGCUGAAAAGACUACUGAAACGGAA GCAACAGAGAAGACUUUG | |
| GS169 dsRNA strand 3' region | 521 bp | UGUAAAAUCUGUUAUAAAAACGAACUUGGUGUUGUA UUCUUGCCUUGUGGACAUGUUGUUGCUUGUGUAGAU UGUGCUUCUGCUUUGAAAACUUGUGCUGUCUGUAGG AAACCUUUGGAAGCGACAGUUCGAGCAUUUCUCUCA UAAUUUUUCCAUUCUUUAAUUUUCGUUUCUCAGAUC UAGUCAAUUUGAAUUUGAUUCUUGAAGGUUUAUUAA AAAGUUUUGUCAAAAAUUAUUCUUUUCUUGUUUUAG GAUUAGAAGUAAAUCUAUUUUUAUACAAUCUGAGUA CAAAUUCCACAUACUUUUUUAGUUAUAAGUUUGAAG CGCUUAUGAAACAUACUUUUUAGUUCAUUAAUGACUG CAAACCAUAUCUUUCGUACACUAAUACUUAUUAGUU AUCAAGCUCUCGUGAGUGGAACUUCCUUAUUAGAAC AUUUUAUUAUAAAACUGACACAGAGAUAUAUCUGUA UGUUUGUGUGUAUGUUCACUAAGUAUGCUAAUAAUA UAAUAAUUUAUGAAAAA | 25 |
| GS170 dsRNA strand 70% identity to GS3 | 432 bp | GAUGAGUGACUGCAGAAUCUUUGUUUCCGCUGAGGU UGUUGGCUUGAACACUAGGAAAGAGGUUAUGAACCU UGGUAACUACACACCAUUUGAUGCAGCAAGCGUGAU CUUCUAAAUUAGUUAGCAAUGAAAGCCUUUGUCUAA GGGGUGAACCAGCGUGCCGAGCCUCUCUAGCCCCUC UCUGACACAAGUCAAAACAUGAUCAUUGGGCUUGUA GAGCCUCGAGAGGUCUGCAGUAGAACACCAGACCAG GCUGGAAAGUCUCCUGAAACAGAUCCACCAGAGGAG ACGUAGUUGAAAAAUCCGUUAUAGAAUCGAACUUCGC GUUGUACCACGGCUUUAUAGGCAACCAGUUACUUGU CUAGAUUGUGCUUCAGCUACUAGAAAAUUGUGCUGAA AGGAGGAAACCACUGCAAGGGCUGGAACGGGGAUUA | 26 |
| GS171 dsRNA strand 75% identity to GS3 | 432 bp | AGUGUUUUAAAAACGCCCCUUUUUGGCUACUGUAGU UGUAGUUUCAAAAACUGUGAAGAAUCGGACGAUCAU UGGGAACAACACGCGCUUUCGUUCAGCAAGUGGACU UCUAGAACUUUGAAAAAGGUAAUGACACAGUUGAG GAGGUCAAACUGAGGGCACACGCUCUCUUGUCGCAG CCGGGAACAAGACAAGACAUGACCAAUAAGAUAGAA GGACAUACAGGCUCAUUGAGUAGGGCUCGAGAAAAA GGUCAAAAGACUACUGAUACGGAACCCCCACAGCAC ACAUUGUCUACUAUCUGACCUAAGAUCUGACCUGGU GUUUAUAUUCUUGACCUGUGGACCUGUUGUGGCUUG CUAGAUUGAGCUACUGACAUGAAAAUAUCUGAUGUC UGUAGGAAGCAUACGGAAGCGACGGCAUGCGCAUUU | 27 |
| GS172 dsRNA strand 80% identity to GS3 | 432 bp | GUUGUGGGAGACCAGUCUAUGUGGUGCAACUAUACU GGUGGUCAUAAAAACUGGGACAUAUCAGACGUACCU CGGGUAGAACCCGCGCUUUGGGUUCAGGAAGUGUGUU UUGCUAAAAAUGAUAUAAGCUCAAGACUUUGUCGAA AACGACAACCAGAGGGAAGAACAUCUCUUGUCGCUC UCCGAAACAACUCAAAACAAGACCAAAAAGAUAGAG GUAUCGGAAGAGCCCAGCAGUAGGAGCCUCGAACAG GCUGAAGAGACUACUAAGAGGGACGCUACAGAGCAC ACUUUGACUAAGAUCUGUUAAAAAGACGAGCUUGGU UUAGUUUUCUUACCUGGUUGACUUGUUGUUGCCUGU CGAAAUUGUGCUUCUGCUUUGAAAACUUGUGCUGUC UGUAGGCAACCUUUGGAAUCGACAGUUAGCGCAUUC | 28 |
| GS173 dsRNA strand 85% identity to GS3 | 432 bp | GGUGUAGGAGACCAGACACUCUGUUUCUACUGAGGU GCUCGUCUAGGAGACCGUGUAGAAUCUAACGAACCU UGGGAACAACACGCCCUUUGUUUCAGCCAGUGUGAU UUUCAAAAUGUGAAAUAAGGUUAAGACUUUGUCGGC AAGGUCAAACAGAGGCCAGACCAUCUCUUGACGCGC CCCGUAACAAGUCAAGAAAAUACCAACGAGCUACAA GAACAUAAAGAGCGCUGCAGUAGGACUCCGGAAAAG GUUGAAGACUACUGAAAGGGAAGCAAGAGGUAAG GCUAUGUGUUAAUUCUUUUAUAAAGACUUUCUUGGU GUCGUAUAUUGCCUUGUGGCCAUGUUGUUGCUCGU GUAGGUUGUUCUUCUGCUUAAGCAACUUGUGCUGUA UGUAGCAAACUUUUGCCAGCGGCAGUUCGAGCAUUU | 29 |

TABLE 8-continued

Sequences, 5'→3'

| Description | Length (bp) | Sequence | SEQ ID NO: |
|---|---|---|---|
| GS174 dsRNA strand 90% identity to GS3 | 432 bp | GGUGUGGGAGAGCAGACACUUCGUUUCUACAGUGGUGGCGGUCUAAAAGACUGGGAAGAAUCUGACGAGCCUUGCGAACAACAGGCACUUGGGUUCAGCAAGUUUGCUUUUCUGAAUUUGAAAAAAUGUUAAGACCUUGUCGGAAAGGUCAAACAGAGGCCAGACCCUCUCUUGUGGCACCCCUGAACAAGUCAAGACAAGACCACAGGCCGAGAAGAACCUAAAGAGCCCUGCAGCAGGACUCCAGACAAGGCUGAAAAGACUACUGCAACGGAAGCAGGAGAAAAGGCUUUGUGUAAAAUCUGUUCUAAAAACGAACUUGGAGUUGUAUUCUGGCCUUGUGGCCAUGUUGUUGCGGGUGUCGAUUGUGCGUCUGCUUUGAAUACUUGUGCUGUCCUUAGGAAACCUUUGGAAGCGACAGUUCGAGCAAUU | 30 |
| GS175 dsRNA strand 95% identity to GS3 | 432 bp | GGUGUGGGAGACCAGACACUUUGUUUCUACUGUGAUGGUGGUCUAAAAGACUGGGAAAAAUCUGACGAACCUUGGGUACAACACGGCCUUUGGUUCAGCAAGUGUGUCUUUAUAAAUUUGAAAAAAGGUAAAGACUUUGGCGAAAAGGUCAAGCAGAGGGCAAUCCCUCUCUUGUCGCACCCCGGAACAAGUCAAGACAAGACCAAAGAGCUAGACGAACCUAAAGAGCCCUGCAGUAGGACUCCAGAAAAGGCUGAAAAGACUACUGAAACGGAAGCCACAGAGAAGACUUUGUGUAAAAUCUGUUAUAAAAACCAACUUGAUGUUGUUUUCUUGCCAUGUGGACAUUUUGUUGCUUGUGGAGCUUGUGCUUCUGCUUUGAAAACUUGUGCUGUCUGUAGGAAACCUUUGGAAGCGACAGUUCGAGCAUUC | 31 |
| GS176 dsRNA strand Nucleotides (nt) 160-360 of GS3 | 200 bp | GCAGACCCUCUCUUGUCGCUCCCCGGAACAAGUCAAGACAAGACCAAAGAGCUAGAAGAACCUAAAGAGCCCUGCAGUAGGACUCCAGAAAAGGCUGAAAAGACUACUGAAACGGAAGCAACAGAGAAGACUUUGUGUAAAAUCUGUUAUAAAAACGAACUUGGUGUUGUAUUCUUGCCUUGUGGACAUGUUGUUGCUUG | 32 |
| GS177 dsRNA strand nt 185-335 of GS3 | 150 bp | GAACAAGUCAAGCAAGACCAAAGAGCUAGAAGAACCUAAAGAGCCCUGCAGUAGGACUCCAGAAAAGGCUGAAAAGACUACUGAAACGGAAGCAACAGAGAAGACUUUGUGUAAAAUCUGUUAUAAAAACGAACUUGGUGUUGUAUUCU | 33 |
| GS178 dsRNA strand nt 210-310 of GS3 | 100 bp | GCUAGAAGAACCUAAAGAGCCCUGCAGUAGGACUCCAGAAAAGGCUGAAAAGACUACUGAAACGGAAGCAACAGAGAAGACUUUGUGUAAAAUCUGUUAU | 34 |
| GS179 dsRNA strand nt 235-385 of GS3 | 50 bp | AGUAGGACUCCAGAAAAGGCUGAAAAGACUACUGAAACGGAAGCAACAGA | 35 |
| GS180 dsRNA strand nt 247-272 of GS3 | 25 bp | GAAAAGGCUGAAAAGACUACUGAAA | 36 |
| REVERSE COMPLEMENT RNA STRANDS | | | |
| IAP mRNA reverse complement | 1564 | UUUUUCAUAAAUUAUUAUAUUAUUAGCAUACUUAGUGAACAUACACACAAACAUACAGAUAUAUCUCUGUGUCAGUUUUAUAAUAAAAUGUUCUAAUAAGGAAGUUCCACUCACGAGAGCUUGAUAACUAAUAAGUAUUAGUGUACGAAAGAUAUGGUUUGCAGUCAUUAAUGAACUAAAAGUAUGUUUCAUAAGCGCUUCAAACUUAUAACUAAAAAAGUAUGUGGAAUUUGUACUCAGAUUGUAUAAAAAUAGAUUUACUUCUAAUCCUAAAACAAGAAAAGAAUAAUUUUUGACAAAACUUUUUAAUAAACCUUCAAGAAUCAAAUUCAAAUUGACUAGAUCUGAGAAACGAAAAUUAAAGAAUGGAAAAAUUAUGAGAGAAAUGCUCGAACUGUCGCUUCCAAAGGUUUCCUACAGACAGCACAAGUUUUCAAAGCAGAAGCACAAUCUACACAAGCAACAACAUGUCCACAAGGCAAGAAUACAACACCAAGUUCGUUUUUAUAACAGAUUUUACACAAAGUCUUCUCUGUUGCUUCCGUUUCAGUAGUCUUUUCAGCCUUUUCUGGAGUCCUACUGCAGGGCUCUUUAGGUUCUUCUAGCUCUUUGGUCUUGUCUUGACUUGUUCCGGGGAGCGACAAGAGA | 37 |

TABLE 8-continued

Sequences, 5'→3'

| Description | Length (bp) | Sequence | SEQ ID NO: |
|---|---|---|---|
| | | GGGUCUGCCCUCUGUUUGACCUUUUCGACAAAGUCU UUACCUUUUUCAAAUUUAGAAAAACACACUUGCUG AACCAAAGGGCGUGUUGUUCCCAAGGUUCGUCAGAU UCUUCCCAGUCUUUUAGACCACCACCACAGUAGAAA CAAAGUGUCUGGUCUCCCACACCGGUAUAAUAAAAU CCCGCUUCUGCCAAAUCAACGGGUCUCUGCUUGAUG GACUUGGGCCAGUUUUCGAACGUUGCUAGUCGACUA UUUACCGUUAUUUUAUCCUGGUUGUGUGGUCCACUU CCUUUGUGGAUUCCCAACUGUUGCAAAUCAAUGGAU CUCCUGUCCUCCGGGAGGGAAUUUGGAAGAACCUCU AUGCCGUACAGUCCACAAGUAUCUGCGUUUCUAUUA CUCCCAGACCUGCCGUUCUCUACAGUUCUAAUAAAA GGACAGUCAGGACUCCAUUCUCGAUGGUCUGCCAUU GGAUCAUCUCCAGAUACCCAAUUGUAUCCUUCUAUC UUACAGAAACGACACAAAACAAUGUCAUCUUGUCCA GUGUAUUCAAAACCGGCAGACGCGAGCGCUUCCUUG GAUAGUUGUGUGCUUGGCCAAUUGUCAAAUGUUCUC AGUCUCGCCUCCAAUGCGGAAUUGUUGACGUUUACU UCAAAAAAACUUUUAUGUUUGGGGUUAUUGUCUGUC UGAUCAGAGUAACUGCUGAUUGUGGGAAAUGUUUGA UUCAUUUUCAUGCCUUCUCAGUACCAAAAAAUAUGA UGCUGUAACACUGCAUGAUUUUUAUAAGAUCCUUCG UAAAAAACACGUUAAAAUCGCCCCAAAUACCAAGUG AACCAAUUGCUCCGACAAACUAGCGAUACGAGAACU GAACUGAACUGAACUGCACGUACGUUUGUAUCUGAA CAACGCAAUGCAUUAG | |
| TAP mRNA reverse complement | 1453 | UUUUUCAUAAAUUAUUAUAUUAUUAGCAUACUUAGU GAACAUACACACAAACAUACAGAUAUAUCUCUGUGU CAGUUUUAUAAUAAAAUGUUCUAAUAAGGAAGUUCC ACUCACGAGAGCUUGAUAACUAAUAAGUAUUAGUGU ACGAAAGAUAUGGUUUGCAGUCAUUAAUGAACUAAA AGUAUGUUUCAUAAGCGCUUCAAACUUAUAACUAAA AAAGUAUGUGGAAUUUGUACUCAGAUUGUAUAAAAA UAGAUUUACUUCUAAUCCUAAAACAAGAAAAGAAUA AUUUUUGACAAAACUUUUUAAUAAACCUUCAAGAAU CAAAUUCAAAUUGACUAGAUCUGAGAAACGAAAAUU AAAGAAUGGAAAAAUUAUGAGAGAAAUGCUCGAACU GUCGCUUCCAAAGGUUUCCUACAGACAGCACAAGUU UUCAAAGCAGAAGCACAAUCUACACAAGCAACAACA UGUCCACAAGGCAAGAAUACAACACCAAGUUCGUUU UUAUAACAGAUUUUACACAAAGUCUUCUCUGUUGCU UCCGUUUCAGUAGUCUUUUCAGCCUUUUCUGGAGUC CUACUGCAGGGCUCUUUAGGUUCUUCUAGCUCUUUG GUCUUGUCUUGACUUGUUCCGGGGAGCGACAAGAGA GGGUCUGCCCUCUGUUUGACCUUUUCGACAAAGUCU UUACCUUUUUCAAAUUUAGAAAAACACACUUGCUG AACCAAAGGGCGUGUUGUUCCCAAGGUUCGUCAGAU UCUUCCCAGUCUUUUAGACCACCACCACAGUAGAAA CAAAGUGUCUGGUCUCCCACACCGGUAUAAUAAAAU CCCGCUUCUGCCAAAUCAACGGGUCUCUGCUUGAUG GACUUGGGCCAGUUUUCGAACGUUGCUAGUCGACUA UUUACCGUUAUUUUAUCCUGGUUGUGUGGUCCACUU CCUUUGUGGAUUCCCAACUGUUGCAAAUCAAUGGAU CUCCUGUCCUCCGGGAGGGAAUUUGGAAGAACCUCU AUGCCGUACAGUCCACAAGUAUCUGCGUUUCUAUUA CUCCCAGACCUGCCGUUCUCUACAGUUCUAAUAAAA GGACAGUCAGGACUCCAUUCUCGAUGGUCUGCCAUU GGAUCAUCUCCAGAUACCCAAUUGUAUCCUUCUAUC UUACAGAAACGACACAAAACAAUGUCAUCUUGUCCA GUGUAUUCAAAACCGGCAGACGCGAGCGCUUCCUUG GAUAGUUGUGUGCUUGGCCAAUUGUCAAAUGUUCUC AGUCUCGCCUCCAAUGCGGAAUUGUUGACGUUUACU UCAAAAAAACUUUUAUGUUUGGGGUUAUUGUCUGUC UGAUCAGAGUAACUGCUGAUUGUGGGAAAUGUUUGA UUCAUUUUCAUGCCUUCAACUAGCGAUACGAGAACUGAA CUGAACUGAACUGCACGUACGUUUGUAUCUGAACAA CGCAAUGCAUUAG | 38 |
| GS3 reverse complement | 432 bp | AAAUGCUCGAACUGUCGCUUCCAAAGGUUUCCUACA GACAGCACAAGUUUUCAAAGCAGAAGCACAAUCUAC ACAAGCAACAACAUGUCCACAAGGCAAGAAUACAAC ACCAAGUUCGUUUUUAUAACAGAUUUUACACAAAGU CUUCUCUGUUGCUUCCGUUUCAGUAGUCUUUUCAGC CUUUUCUGGAGUCCUACUGCAGGGCUCUUUAGGUUC | 39 |

TABLE 8-continued

Sequences, 5'→3'

| Description | Length (bp) | Sequence | SEQ ID NO: |
|---|---|---|---|
| | | UUCUAGCUCUUUGGUCUUGUCUUGACUUGUUCCGGG GAGCGACAAGAGAGGGUCUGCCCUCUGUUUGACCUU UUCGACAAAGUCUUUACCUUUUUUCAAAUUUAGAAA AACACACUUGCUGAACCAAAGGGCGUGUUGUUCCCA AGGUUCGUCAGAUUCUUCCCAGUCUUUUAGACCACC ACCACAGUAGAAACAAAGUGUCUGGUCUCCCACACC | |
| GS4 (negative control) reverse complement | 524 bp | CCGUCCUCGAUGUUGUGGCGGAUCUUGAAGUUCACC UUGAUGCCGUUCUUCUGCUUGUCGGCCAUGAUAUAG ACGUUGUGGCUGUUGUAGUUGUACUCCAGCUUGUGC CCCAGGAUGUUGCCGUCCUCCUUGAAGUCGAUGCCC UUCAGCUCGAUGCGGUUCACCAGGGUGUCGCCCUCG AACUUCACCUCGGCGCGGGUCUUGUAGUUGCCGUCG UCCUUGAAGAAGAUGGUGCGCUCCUGGACGUAGCCU UCGGGCAUGGCGGACUUGAAGAAGUCGUGCUGCUUC AUGUGGUCGGGGUAGCGGCUGAAGCACUGCACGCCG UAGGUCAGGGUGGUCACGAGGGUGGGCCAGGGCACG GGCAGCUUGCCGGUGGUGCAGAUGAACUUCAGGGUC AGCUUGCCGUAGGUGGCAUCGCCCUCGCCCUCGCCGG ACACGCUGAACUUGUGGCCGUUUACGUCGCCGUCCA GCUCGACCAGGAUGGGCACCACCCCGGUGAACAGCU CCUCGCCCUUGCUCACCAU | 40 |
| GS167 reverse complement 5' region | 521 bp | ACUCCCAGACCUGCCGUUCUCUACAGUUCUAAUAAA AGGACAGUCAGGACUCCAUUCUCGAUGGUCUGCCAU UGGAUCAUCUCCAGAUACCCAAUUGUAUCCUUCUAU CUUACAGAAACGACACAAAACAAUGUCAUCUUGUCC AGUGUAUUCAAAACCGGCAGACGCGAGCGCUUCCUU GGAUAGUUGUGUGCUUGGCCAAUUGUCAAAUGUUCU CAGUCUCGCCUCCAAUGCGGAAUUGUUGACGUUUAC UUCAAAAAAACUUUUAUGUUUGGGGUUAUUGUCUGU CUGAUCAGAGUAACUGCUGAUUGUGGGAAAUGUUUG AUUCAUUUUCAUGCCUUCUCAGUACCAAAAAAAUAUG AUGCUGUAACACUGCAUGAUUUUUAUAAGAUCCUUC GUAAAAAACACGUUAAAAAUCGCCCCAAAUACCAAGU GAACCAAUUGCUCCGACAAACUAGCGAUACGAGAAC UGAACUGAACUGAACUGCACGUACGUUUUGUAUCUGA ACAACGCAAUGCAUUAG | 41 |
| GS168 reverse complement central region | 522 bp | CAAAGUCUUCUCUGUUGCUUCCGUUUCAGUAGUCUU UUCAGCCUUUUCUGGAGUCCUACUGCAGGGCUCUUU AGGUUCUUCUAGCUCUUUGGUCUUGUCUUGACUUGU UCCGGGGAGCGACAAGAGAGGGUCUGCCCUCUGUUU GACCUUUUCGACAAAGUCUUUACCUUUUUUCAAAUU UAGAAAAACACACUUGCUGAACCAAAGGGCGUGUUG UUCCCAAGGUUCGUCAGAUUCUUCCCAGUCUUUUAG ACCACCACCACAGUAGAAACAAAGUGUCUGGUCUCC CACACCGGUAUAAUAAAAUCCCGCUUCUGCCAAAUC AACGGGUCUCUGCUUGAUGGACUUGGGCCAGUUUUC GAACGUUGCUAGUCGACUAUUUACCGUUAUUUUAUC CUGGUUGUGGUCCACUUCCUUUGUGGAUUCCCAA CUGUUGCAAAUCAAUGGAUCUCCUGUCCUCCGGGAG GGAAUUUGGAAGAACCUCUAUGCCGUACAGUCCACA AGUAUCUGCGUUUCUAUU | 42 |
| GS169 reverse complement 3' region | 521 bp | UUUUUCAUAAAUUAUUAUAUUAUUAGCAUACUUAGU GAACAUACACACAAACAUACAGAUAUAUCUCUGUGU CAGUUUUAUAAUAAAAUGUUCUAAUAAGGAAGUUCC ACUCACGAGAGCUUGAUAACUAAUAAGUAUUAGUGU ACGAAAGAUAUGGUUUUGCAGUCAUUAAUGAACUAAA AGUAUGUUUCAUAAGCGCUUCAAACUUAUAACUAAA AAAGUAUGUGGAAUUUGUACUCAGAUUGUAUAAAAA UAGAUUUACUUCUAAUCCUAAAACAAGAAAAGAAUA AUUUUUGACAAAACUUUUUAAUUAAACCUUCAAGAU CAAAUUCAAAUUGACUAGAUCUGAGAAACGAAAAUU AAAGAAUGGAAAAAUUAUGAGAGAAAAUGCUCGAACU GUCGCUUCCAAAGGUUUCCUACAGACAGCACAAGUU UUCAAAGCAGAAGCACAAUCUACACAAGCAACAACA UGUCCACAAGGCAAGAAUACAACACCAAGUUCGUUU UUAUAACAGAUUUUACA | 43 |
| GS170 reverse complement 70% | 432 bp | UAAUCCCCGUUCCAGCCCUUGCAGUGGUUUCCUCCU UUCAGCACAAUUUCUAGUAGCUGAAGCACAAUCUAG ACAAGUAACUGGUUGCCUAUAAAGCCGUGGUACAAC GCGAAGUUCGAUUCUAUAACGGAUUUUCAACUACGU | 44 |

TABLE 8-continued

Sequences, 5'→3'

| Description | Length (bp) | Sequence | SEQ ID NO: |
|---|---|---|---|
| complementarity to GS3 | | CUCCUCUGGUGGAUCUGUUUCAGGAGACUUUCCAGC CUGGUCUGGUGUUCUACUGCAGACCUCUCGAGGCUC UACAAGCCCAAUGAUCAUGUUUUGACUUGUGUCAGA GAGGGGCUAGAGAGGCUCGGCACGCUGGUUCACCCC UUAGACAAAGGCUUUCAUUGCUAACUAAUUUAGAAG AUCACGCUUGCUGCAUCAAAUGGUGUGUAGUUACCA AGGUUCAUAACCUCUUUCCUAGUGUUCAAGCCAACA ACCUCAGCGGAAACAAAGAUUCUGCAGUCACUCAUC | |
| GS171 reverse complement 75% complementarity to GS3 | 432 bp | AAAUGCGCAUGCCGUCGCUUCCGUAUGCUUCCUACA GACAUCAGAUAUUUUCAUGUCAGUAGCUCAAUCUAG GCAAGCCACAACAGGUCCACAGGUCAAGAAUAUAAC ACCAGGUCAGAUCUUAGGUCAGAUAGUAGACAAUGU GUGCUGUGGGGGUUCCGUAUCAGUAGUCUUUUGACC UUUUUCUCGAGCCCUACUCAAUGAGCCUGUAUGUCC UUCUAUCUUAUUGGGUCAUGUCUUGUCUUGUUCCCGG CUGCGACAAGAGAGCGUGUGCCCUCAGUUUGACCUC CUCAACUGUGUCAUUACCUUUUUUCAAAGUUCUAGA AGUCCACUUGCUGAACGAAAGCGCGUGUUGUUCCCA AUGAUCGUCCGAUUCUUCACAGUUUUGAAACUACA ACUACAGUAGCCAAAAAGGGGCGUUUUUAAAACACU | 45 |
| GS172 reverse complement 80% complementarity to GS3 | 432 bp | GAAUGCGCUAACUGUCGAUUCCAAAGGUUGCCUACA GACAGCACAAGUUUUCAAAGCAGAAGCACAAUUUCG ACAGGCAACAACAAGUCAACCAGGUAAGAAAACUAA ACCAAGCUCGUCUUUUUAACAGAUCUUAGUCAAAGU GUGCUCUGUAGCGUCCCUCUUAGUAGUCUCUUCAGC CUGUUCGAGGCUCCUACUGCUGGGCUCUUUCCGAUAC CUCUAUCUUUUUGGUCUUGUUUUGAGUUGUUUCGGA GAGCGACAAGAGAUGUUCUUCCCUCUGGUUGUCGUU UUCGACAAAGUCUUGAGCUUAUAUCAUUUUUAGCAA AACACACUUCCUGAACCCAAGCGCGGGUUCUACCCG AGGUACGUCUGAUAUGUCCCAGUUUUUAUGACCACC AGUAUAGUUGCACCACAUAGACUGGUCUCCCACAAC | 46 |
| GS173 reverse complement 85% complementarity to GS3 | 432 bp | AAAUGCUCGAACUGCCGCUGGCAAAAGUUUGCUACA UACAGCACAAGUUGCUUAAGCAGAAGAACAACCUAC ACGAGCAACAACAUGGCCACAAGGCAAAUAUACGAC ACCAAGAAAGUCUUUAUAAAAGAAUUAACACAUAGC CUUACCUCUUGCUUCCCUUUCAGUAGUCUUCUCAAC CUUUUCCGGAGUCCUACUGCAGCGCUCUUUAUGUUC UUGUAGCUCGUUGGUAUUUUCUUGACUUGUUACGGG GCGCGUCAAGAGAUGGUCUGGCCUCUGUUUGACCUU GCCGACAAAGUCUUAACCUUAUUUCACAUUUUGAAA AUCACACUGGCUGAAACAAAGGGCGUGUUGUUCCCA AGGUUCGUUAGAUUCUACACGGUCUCCUAGACGAGC ACCUCAGUAGAAACAGAGUGUCUGGUCUCCUACACC | 47 |
| GS174 reverse complement 90% complementarity to GS3 | 432 bp | AAUUGCUCGAACUGUCGCUUCCAAAGGUUUCCUAAG GACAGCACAAGUAUUCAAAGCAGACGCACAAUCGAC ACCCGCAACAACAUGGCCACAAGGCCAGAAUACAAC UCCAAGUUCGUUUUUAGAACAGAUUUUACACAAAGC CUUUUCUCCUGCUUCCGUUGCAGUAGUCUUUUCAGC CUUGUCUGGAGUCCUGCUGCAGGGCUCUUUAGGUUC UUCUCGGCCUGUGGUCUUGUCUUGACUUGUUCAGGG GUGCCACAAGAGAGGGUCUGGCCUCUGUUUGACCUU UCCGACAAGGUCUUAACAUUUUUUCAAAUUCAGAAA AGCAAACUUGCUGAACCCAAGUGCCUGUUGUUCGCA AGGCUCGUCAGAUUCUUCCCAGUCUUUUAGACCGCC ACCACUGUAGAAACGAAGUGUCUGCUCUCCCACACC | 48 |
| GS175 reverse complement 95% complementarity to GS3 | 432 bp | GAAUGCUCGAACUGUCGCUUCCAAAGGUUUCCUACA GACAGCACAAGUUUUCAAAGCAGAAGCACAAGCUCC ACAAGCAACAAAAUGUCCACAUGGCAAGAAAACAAC AUCAAGUUGGUUUUUAUAACAGAUUUUACACAAAGU CUUCUCUGUGGCUUCCGUUUCAGUAGUCUUUUCAGC CUUUUCUGGAGUCCUACUGCAGGGCUCUUUAGGUUC GUCUAGCUCUUUGGUCUUGUCUUGACUUGUUCCGGG GUGCGACAAGAGAGGGAUUGCCCUCUGCUUGACCUU UUCGCCAAAGUCUUUACCUUUUUUCAAAUUUAUAAA GACACACUUGCUGAACCCAAAGGCCGUGUUGUACCCA AGGUUCGUCAGAUUUUCCCAGCUUUUAGACCACC AUCACAGUAGAAACAAAGUGUCUGGUCUCCCACACC | 49 |

TABLE 8-continued

Sequences, 5'→3'

| Description | Length (bp) | Sequence | SEQ ID NO: |
|---|---|---|---|
| GS176 reverse complement Nucleotides (nt) 160-360 of GS3 | 200 bp | CAAGCAACAACAUGUCCACAAGGCAAGAAUACAACA CCAAGUUCGUUUUUAUAACAGAUUUUACACAAAGUC UUCUCUGUUGCUUCCGUUUCAGUAGUCUUUUCAGCC UUUUCUGGAGUCCUACUGCAGGGCUCUUUAGGUUCU UCUAGCUCUUUGGUCUUGUCUUGACUUGUUCCGGGG AGCGACAAGAGAGGGUCUGC | 50 |
| GS177 reverse complement nt 185-335 of GS3 | 150 bp | AGAAUACAACACCAAGUUCGUUUUUAUAACAGAUUU UACACAAAGUCUUCUCUGUUGCUUCCGUUUCAGUAG UCUUUUCAGCCUUUUCUGGAGUCCUACUGCAGGGCU CUUUAGGUUCUUCUAGCUCUUUGGUCUUGUCUUGAC UUGUUC | 51 |
| GS178 reverse complement nt 210-310 of GS3 | 100 bp | AUAACAGAUUUUACACAAAGUCUUCUCUGUUGCUUC CGUUUCAGUAGUCUUUUCAGCCUUUUCUGGAGUCCU ACUGCAGGGCUCUUUAGGUUCUUCUAGC | 52 |
| GS 179 reverse complement nt 235-385 of GS3 | 50 bp | UCUGUUGCUUCCGUUUCAGUAGUCUUUUCAGCCUUU UCUGGAGUCCUACU | 53 |
| GS180 reverse complement nt 247-272 of GS3 | 25 bp | UUUCAGUAGUCUUUUCAGCCUUUUC | 54 |

*Both sequences are 24 bp longer than the actual target sequences due to part of the T7 promoter and a restriction site.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A double-stranded RNA (dsRNA) that inhibits expression of a Leptinotarsa *decemlineata* Inhibitor of Apoptosis (IAP) gene, wherein a first strand of the dsRNA comprises an RNA sequence that is at least 100 nucleotides in length and is 90% to 100% complementary to the RNA encoded by SEQ ID NO: 3.

2. The dsRNA of claim 1, wherein a second strand of the dsRNA is complementary to the first strand.

3. The dsRNA of claim 1, wherein the RNA sequence comprises the RNA sequence of SEQ ID NO: 21.

4. The dsRNA of claim 2, wherein the first strand of the dsRNA comprises an RNA sequence that is 95% to 100% complementary to the RNA mRNA or a encoded by SEQ ID NO: 3.

5. The dsRNA of claim 1, wherein the RNA has a length of 100 to 432 nucleotides.

6. The dsRNA of claim 1, wherein the first strand of the dsRNA comprises 18 to 21 contiguous nucleotides 90% to 100% complementary to the RNA encoded by SEQ ID NO: 3.

7. The dsRNA of claim 1, wherein the first strand comprises an RNA sequence that has 90% to 100% identity to the RNA sequence of SEQ ID NO: 39.

8. The dsRNA of claim 7, wherein the first strand comprises 18 to 21 contiguous nucleotides that have 90% to 100% identity to the RNA sequence of SEQ ID NO: 39.

9. The dsRNA of claim 1, wherein the first strand comprises an RNA sequence that has 100% identity to the RNA sequence of any one of SEQ ID NOs: 39 or 48-52.

10. A composition comprising the dsRNA of claim 1.

11. The composition of claim 10, wherein the composition further comprises at least one additive selected from the group consisting of: adjuvants, attractants, growth-regulating substances, insect feed, pheromones, proteins, carbohydrates, polymers, organic compounds, biologics, and pesticidal agents.

12. The composition of claim 10 formulated at a concentration of 0.001 µg/cm$^2$ to 10 µg/cm$^2$.

13. The composition of claim 10, wherein the composition is formulated as a liquid, a solution, a suspension, an emulsion, an emulsifiable concentrate, a concentrate solution, a low concentrate solution, an ultra-low volume concentrate solution, a water soluble concentrate solution, a bait, an invert emulsion, a flowable, an aerosol, a smoke, a fog, a flowable, a homogenous mixture, a non-homogenous mixture, a solid, a dust, a powder, a granule, a pellet, a capsule, a fumigant, an encapsulated formulation, or a micro-encapsulation formulation.

14. The composition of claim 10, wherein the composition is delivered as a spray, fog, seed treatment, drench, drip irrigation, in furrow, insect diet, or bait.

15. A deoxyribonucleic acid (DNA) encoding the RNA of claim 1.

16. A plant comprising the dsRNA of claim 1.

17. The plant of claim 16, wherein the plant is a Solanaceae plant, Brassicaceae plant, Poaceae plant, Cucurbitaceae plant, Fobaceae plant, Apiaceae plant, Amaranthaceae plant, or *Malvaceae* plant.

18. A method for controlling Coleopteran insect infestation, the method comprising delivering to a plant, ground, a Coleopteran insect, or a diet of a Coleopteran insect the dsRNA of claim 1.

19. The method of claim 18, wherein the dsRNA is delivered to a leaf, stem, seed, root, or soil of the plant.

20. The method of claim 18, wherein the plant is selected from the group consisting of Solanaceae plants, Brassicaceae plants, Poaceae plants, Cucurbitaceae plants, Fobaceae plants, Apiaceae plants, Amaranthaceae plants, and *Malvaceae* plants.

* * * * *